US011615864B2

(12) United States Patent
Salzman

(10) Patent No.: US 11,615,864 B2
(45) Date of Patent: Mar. 28, 2023

(54) ACCURATE AND SENSITIVE UNVEILING OF CHIMERIC BIOMOLECULE SEQUENCES AND APPLICATIONS THEREOF

(71) Applicant: The Board of Trustees of the Leland Stanford Junior University, Stanford, CA (US)

(72) Inventor: Julia Salzman, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 820 days.

(21) Appl. No.: 16/487,033

(22) PCT Filed: Feb. 20, 2018

(86) PCT No.: PCT/US2018/018844
§ 371 (c)(1),
(2) Date: Aug. 19, 2019

(87) PCT Pub. No.: WO2018/152542
PCT Pub. Date: Aug. 23, 2018

(65) Prior Publication Data
US 2020/0202980 A1    Jun. 25, 2020

Related U.S. Application Data

(60) Provisional application No. 62/460,708, filed on Feb. 17, 2017.

(51) Int. Cl.
*G16B 30/10* (2019.01)
*G06F 16/901* (2019.01)
(Continued)

(52) U.S. Cl.
CPC ......... *G16B 30/10* (2019.02); *G06F 16/9027* (2019.01); *G06F 30/20* (2020.01);
(Continued)

(58) Field of Classification Search
CPC ............................ G16B 30/10; G06F 16/9027
See application file for complete search history.

(56) References Cited

U.S. PATENT DOCUMENTS

2004/0110227 A1    6/2004  Levanon et al.
2011/0288832 A1*  11/2011  Pierce ................... G16B 30/00
                                                                    703/2

(Continued)

FOREIGN PATENT DOCUMENTS

WO    2018152542 A1    8/2018

OTHER PUBLICATIONS

International Preliminary Report on Patentability for International Application PCT/US2018/018844, dated Aug. 20, 2019, dated Aug. 29, 2019, 6 Pgs.

(Continued)

*Primary Examiner* — Yi Yang
(74) *Attorney, Agent, or Firm* — KPPB LLP

(57) ABSTRACT

Unveiling of chimeric biomolecule sequences and applications thereof are described. Generally, systems comprising statistical analysis are performed to unveil chimeric biomolecule sequences from sequencing data sets. Bloom filters and hierarchical bloom filter tree data structures can be constructed such that chimeric sequence unveiling systems are more efficient. Finally, chimeric sequences are used to develop research tools, diagnostics, and medicaments.

53 Claims, 29 Drawing Sheets
Specification includes a Sequence Listing.

(51) Int. Cl.
   *G16B 40/00* (2019.01)
   *G16B 5/20* (2019.01)
   *G06F 30/20* (2020.01)
   *G06F 111/10* (2020.01)

(52) U.S. Cl.
   CPC ............... *G16B 5/20* (2019.02); *G16B 40/00* (2019.02); *G06F 2111/10* (2020.01)

(56) References Cited

U.S. PATENT DOCUMENTS

| | | | | |
|---|---|---|---|---|
| 2012/0072123 | A1* | 3/2012 | Brown | G16B 20/50 702/19 |
| 2012/0208706 | A1* | 8/2012 | Downing | C12Q 1/6874 506/9 |
| 2014/0065620 | A1* | 3/2014 | Perez | C12Q 1/6886 435/6.12 |
| 2014/0235458 | A1* | 8/2014 | Houldsworth | C12Q 1/6886 506/9 |
| 2015/0370906 | A1* | 12/2015 | Hong | H04L 45/7453 707/754 |
| 2016/0292356 | A1 | 10/2016 | Kim et al. | |
| 2016/0306922 | A1* | 10/2016 | van Rooyen | G16B 50/30 |

OTHER PUBLICATIONS

International Search Report and Written Opinion for International Application No. PCT/US2018/018844, Search completed Jun. 6, 2018, dated Jun. 21, 2018, 19 Pgs.
Hsieh et al., "Statistical algorithms improve accuracy of gene fusion detection", In: Nucleic Acids Research, 2017, vol. 45, No. 13, 11 pgs.
Kumar et al., "Identifying Fusion Transcripts Using Next Generation Sequencing Advanced Review", In: Wiley Interdiscip Rev RNA. Nov. 2016, pp. 811-823.
Okonechnikov et al., "InFusion: Advancing Discovery of Fusion Genes and Chimeric Transcripts from Deep RNA-Sequencing Data", In: PLoS One. Dec. 1, 2016, 38 pgs.
Tu et al., "Systematic Characteristic Exploration of the Chimeras Generated in Multiple Displacement Amplification through Next Generation Sequencing Data Reanalysis", In: PLoS One. Oct. 6, 2015, 17 pgs.
Wu et al., "SOAPfusion: a robust and effective computational fusion discovery tool for RNA-seq reads", In: Bioinformatics. Dec. 2013. 42 pgs.
"Integrated genomic analyses of ovarian carcinoma", The Cancer Genome Atlas Research Network, Nature, vol. 474, Jun. 29, 2011, pp. 609-615.
Bacher et al., "Subclones with the t(9;22)/BCR-ABL1 rearrangement occur in AML and seem to cooperate with distinct genetic alterations", British Journal of Haematology, vol. 152, No. 6, Jan. 31, 2011, pp. 713-720.
Carneiro et al., "FGFR3-TACC3: A novel gene fusion in cervical cancer", Gynecologic Oncology Reports, vol. 13, Aug. 2015, pp. 53-56.
Carrara et al., "State of art fusion-finder algorithms are suitable to detect transcription-induced chimeras in normal tissues?", BMC Bioinformatics, vol. 14, No. S2, Apr. 22, 2013, 11 pgs.
Chase et al., "TFG, A Target Of Chromosome Translocations In Lymphoma And Soft Tissue Tumors, Fuses To GPR128 In Healthy Individuals", Haematologica, vol. 95, No. 1, Jan. 2010, pp. 20-26.
Chothia et al., "Canonical Structures for the Hypervariable Regions of Immunoglobulins", Journal of Molecular Biology, vol. 196, Issue 4, Aug. 20, 1987, pp. 901-917, https://doi.org/10.1016/0022-2836(87)90412-8.
Druker et al., "Efficacy and Safety of a Specific Inhibitor of the BCR-ABL Tyrosine Kinase in Chronic Myeloid Leukemia", The New England Journal of Medicine, vol. 344, No. 14, Apr. 5, 2001, pp. 1031-1037.
Eswaran et al., "RNA sequencing of cancer reveals novel splicing alterations", Scientific Reports, vol. 3, No. 1689, Apr. 22, 2013, 12 pgs.
Gozgit et al., "Ponatinib (AP24534), a Multitargeted Pan-FGFR Inhibitor with Activity in Multiple FGFR-Amplified or Mutated Cancer Models", Molecular Cancer Therapeutics, vol. 11, No. 3, Mar. 2012, pp. 690-699.
Halasi et al., "ROS inhibitor N-acetyl-L-cysteine antagonizes the activity of proteasome inhibitors", Biochemical Journal, vol. 454, No. 2, Aug. 9, 2013, pp. 201-208.
Hoeffding, "A Combinatorial Central Limit Theorem", Annals of Mathematical Statistics, vol. 22, No. 4, Dec. 1951, pp. 558-566.
Jia et al., "SOAPfuse: an algorithm for identifying fusion transcripts from paired-end RNA-Seq data", Genome Biology, vol. 14, No. R12, Feb. 14, 2013, 15 pgs.
Ju et al., "A transforming KIF5B and RET gene fusion in lung adenocarcinoma revealed from whole-genome and transcriptome sequencing", Genome Research, vol. 22, No. 3, Mar. 2012, pp. 436-445.
Kadoch et al., "Reversible Disruption of mSWI/SNF (BAF) Complexes by the SS18-SSX Oncogenic Fusion in Synovial Sarcoma", Cell, vol. 153, No. 1, Mar. 28, 2013, pp. 71-85.
Kohler et al., "Continuous cultures of fused cells secreting antibody of predefined specificity", Nature, Aug. 7, 1975, vol. 256, pp. 495-497.
Kumar et al., "Comparative assessment of methods for the fusion transcripts detection from RNA-Seq data", Scientific Reports, vol. 6, No. 21597, Feb. 10, 2016, 10 pgs.
Langmead et al., "Fast gapped-read alignment with Bowtie 2", Nature Methods, vol. 9, Mar. 4, 2012, pp. 357-359.
Latysheva et al., "Discovering and understanding oncogenic gene fusions through data intensive computational approaches", Nucleic Acids Research, vol. 44, No. 10, Apr. 21, 2016, pp. 4487-4503.
Lee et al., "ChimerDB 3.0: an enhanced database for fusion genes from cancer transcriptome and literature data mining", Nucleic Acids Research, vol. 45, No. D1, Nov. 28, 2016, pp. D784-D789.
Ley et al., "Genomic and Epigenomic Landscapes of Adult De Novo Acute Myeloid Leukemia", The Cancer Genome Atlas Research Network, The New England Journal of Medicine, vol. 368, No. 22, May 30, 2013, pp. 2059-2074.
Liu et al., "Comprehensive evaluation of fusion transcript detection algorithms and a meta-caller to combine top performing methods in paired-end RNA-seq data", Nucleic Acids Research, vol. 44, No. 5, Nov. 17, 2015, e47, 15 pgs.
Maher et al., "Transcriptome sequencing to detect gene fusions in cancer", Nature, vol. 458, No. 7234, Jan. 11, 2009, pp. 97-101.
Marcais et al., "A fast, lock-free approach for efficient parallel counting of occurrences of k-mers", Bioinformatics, vol. 27, No. 6, Mar. 15, 2011, pp. 764-770.
Martin, "Cutadapt Removes Adapter Sequences From High-Throughput Sequencing Reads", EMBnet.journal: Bioinformatics in Action, vol. 17, No. 1, Technical Notes, 2011, pp. 10-12.
McNerney et al., "CUX1 is a haploinsufficient tumor suppressor gene on chromosome 7 frequently inactivated in acute myeloid leukemia", Blood, vol. 121, No. 6, Feb. 7, 2013, pp. 975-983.
Ni et al., "Premature polyadenylation of MAGI3 produces a dominantly-acting oncogene in human breast cancer", eLife, vol. 5, May 20, 2016, e14730, 21 pgs.
Papaemmanuil et al., "Genomic Classification and Prognosis in Acute Myeloid Leukemia", The New England Journal of Medicine, vol. 374, No. 23, Jun. 9, 2016, pp. 2209-2221.
Raman et al., "Succinct indexable dictionaries with applications to encoding k-ary trees, prefix sums and multisets", ACM Transactions on Algorithms, vol. 3, No. 4, Nov. 2007, 25 pgs.
Riggi et al., "EWS-FLI1 Utilizes Divergent Chromatin Remodeling Mechanisms to Directly Activate or Repress Enhancer Elements in Ewing Sarcoma", Cancer Cell, vol. 26, No. 5, Nov. 10, 2014, pp. 668-681.
Sadis et al., "High-throughput, systematic analysis of paired-end next-generation sequencing data to characterize the gene fusion landscape in cancer", Compendia Bioscience, Life Technologies, Abstract No. 3173, 2013, 1 pg.

(56) References Cited

OTHER PUBLICATIONS

Shen et al., "Widespread establishment and regulatory impact of Alu exons in human genes", Proceedings of the National Academy of Sciences of the United States of America, vol. 108, No. 7, Feb. 15, 2011, pp. 2837-2842.

Singh et al., "Transforming Fusions of FGFR and TACC Genes in Human Glioblastoma", Science, vol. 337, No. 6099, Sep. 7, 2012, pp. 1231-1235.

Soda et al., "Identification of the transforming EML4-ALK fusion gene in non-small-cell lung cancer", Nature, vol. 448, Jul. 11, 2007, pp. 561-566.

Solomon et al., "Fast search of thousands of short-read sequencing experiments", Nature Biotechnology, vol. 34, No. 3, Feb. 8, 2016, pp. 300-302.

Solomon et al., "Large-Scale Search of Transcriptomic Read Sets with Sequence Bloom Trees", bioRxiv preprint doi: https://doi.org/10.1101/017087, Mar. 26, 2015, 30 pgs.

Stransky et al., "The landscape of kinase fusions in cancer", Nature Communications, vol. 5, No. 4846, Sep. 10, 2014, 10 pgs.

Szabo et al., "Statistically based splicing detection reveals neural enrichment and tissue-specific induction of circular RNA during human fetal development", Genome Biology, vol. 16, No. 126, Jun. 16, 2015, 26 pgs.

Tay et al., "Coding-Independent Regulation of the Tumor Suppressor PTEN by Competing Endogenous mRNAs", Cell, vol. 147, No. 2, Oct. 14, 2011, pp. 344-357.

Tomlins et al., "Recurrent Fusion of TMPRSS2 and ETS Transcription Factor Genes in Prostate Cancer", Science, vol. 310, No. 5748, Oct. 28, 2005, pp. 644-648.

Weisberg et al., "Inhibition of mutant FLT3 receptors in leukemia cells by the small molecule tyrosine kinase inhibitor PKC412", Cancer Cell, vol. 1, No. 5, Jun. 1, 2002, pp. 433-443.

Yoshihara et al., "The landscape and therapeutic relevance of cancer-associated transcript fusions", Oncogene, vol. 34, No. 37, Dec. 15, 2014, pp. 4845-4854.

\* cited by examiner

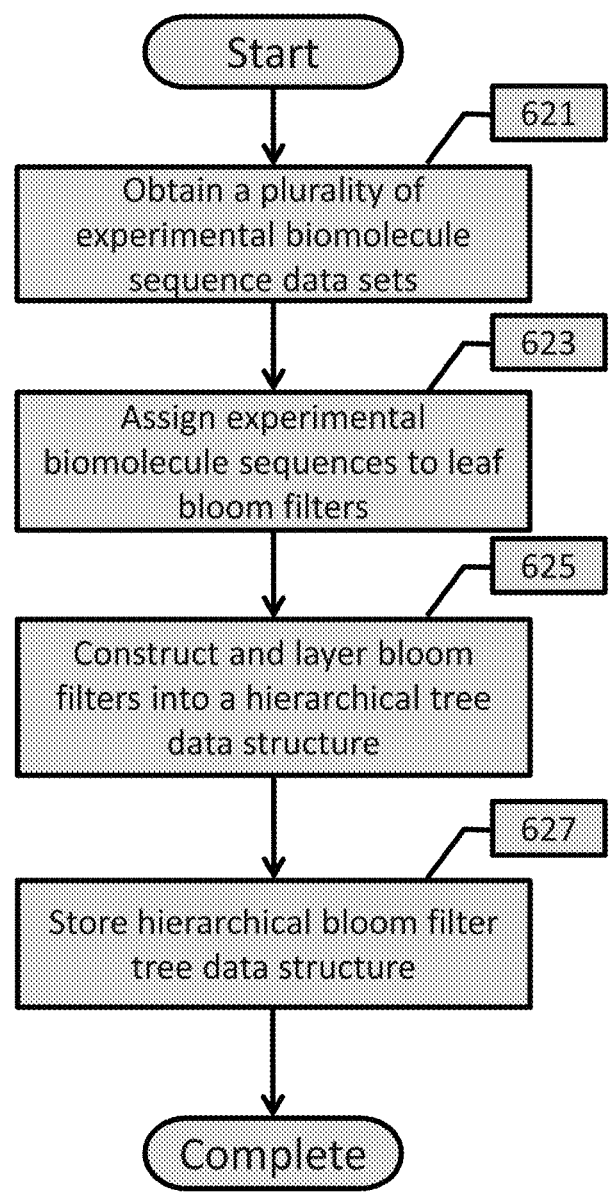

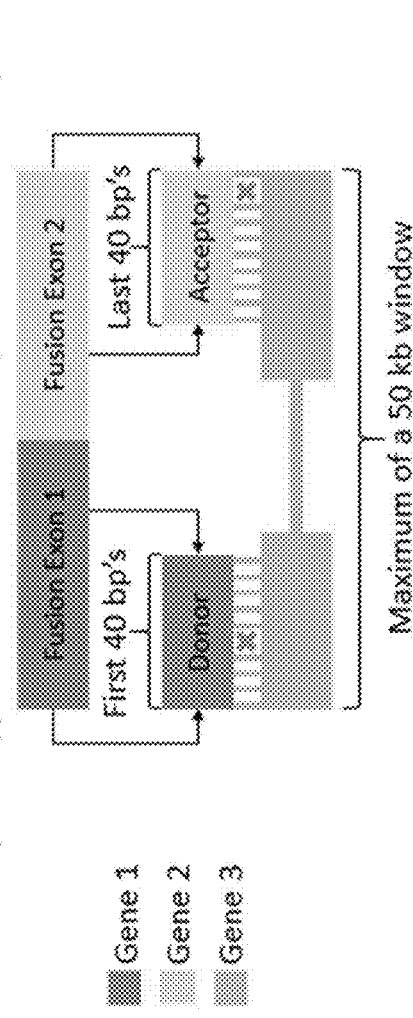
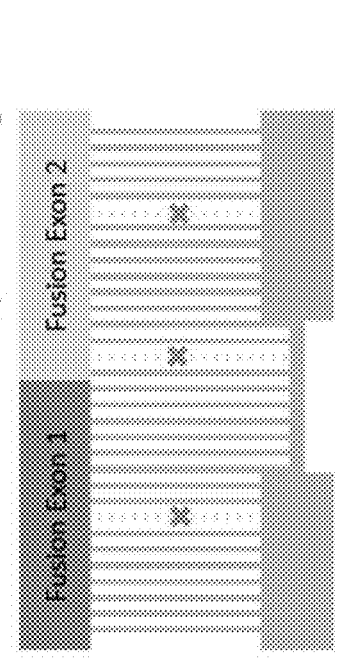
Fig. 12

Fig. 15

| Algorithm | True Positives (mixed set) | False Positives (mixed set) | Sensitivity (100%)* TP/(TP+FN) | PPV (100%)* TP/(TP+FP) | False Positives (Engstrom) | False Positives (fetal) | False Positives (normal breast) |
|---|---|---|---|---|---|---|---|
| Ericscript | | | 80% | 75.4% | | | |
| SOAPfuse | 35 | 35 | 74% | 69.8% | 7 | 6 | 5 |
| STAR-Fusion | | 6 | 84% | 87.5% | 0 | | 6 |
| MACHETE | 38 | 0 | 86% | 100% | 0 | 0 | 1 |

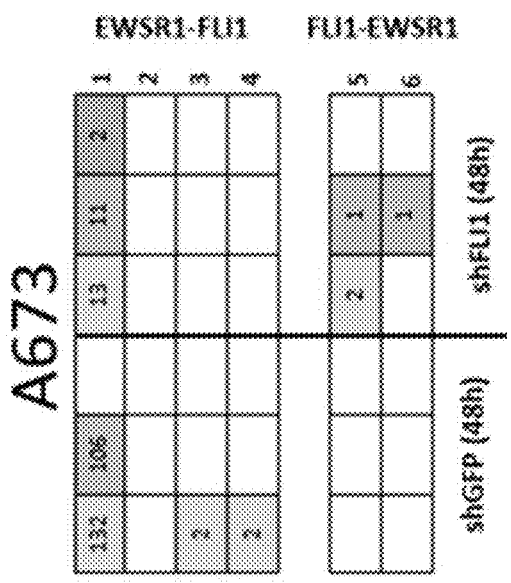
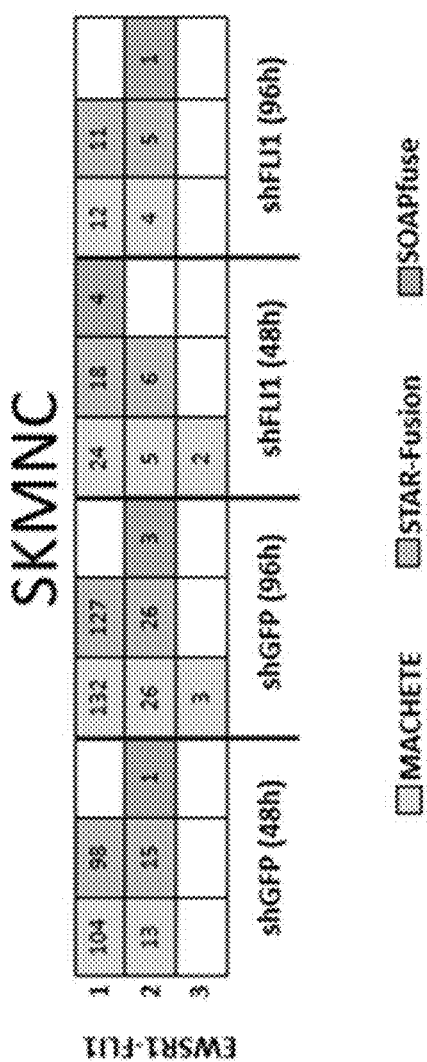
Fig. 19

AML fusions discovered precisely with sMACHETE, many FP with best competitor

SEQUENCE LISTING

<160> NUMBER OF SEQ ID NOS: 38

<210> SEQ ID NO 1
<211> LENGTH: 19
<212> TYPE: DNA
<213> ORGANISM: Artificial Sequence

```
<220> FEATURE:
<223> OTHER INFORMATION: in silico derived

<400> SEQUENCE: 1
aagtattttc aaagaattt                                                19

<210> SEQ ID NO 2
<211> LENGTH: 20
<212> TYPE: DNA
<213> ORGANISM: Artificial Sequence
<220> FEATURE:
<223> OTHER INFORMATION: in silico derived

<400> SEQUENCE: 2
ccatatttca actatataca                                               20

<210> SEQ ID NO 3
<211> LENGTH: 20
<212> TYPE: DNA
<213> ORGANISM: Artificial Sequence
<220> FEATURE:
<223> OTHER INFORMATION: in silico derived
<220> FEATURE:
<221> NAME/KEY: misc_feature
<222> LOCATION: (20)..(20)
<223> OTHER INFORMATION: n is a, c, g, or t

<400> SEQUENCE: 3
aagtattttc aaagaatttn                                               20

<210> SEQ ID NO 4
<211> LENGTH: 21
<212> TYPE: DNA
<213> ORGANISM: Artificial Sequence
<220> FEATURE:
<223> OTHER INFORMATION: in silico derived
<220> FEATURE:
<221> NAME/KEY: misc_feature
<222> LOCATION: (1)..(1)
<223> OTHER INFORMATION: n is a, c, g, or t

<400> SEQUENCE: 4
nccatatttc aactatatac a                                             21

<210> SEQ ID NO 5
<211> LENGTH: 18
<212> TYPE: DNA
<213> ORGANISM: Artificial Sequence
<220> FEATURE:
<223> OTHER INFORMATION: in silico derived

<400> SEQUENCE: 5
aagtattttc aaagaatt                                                 18

<210> SEQ ID NO 6
<211> LENGTH: 19
<212> TYPE: DNA
<213> ORGANISM: Artificial Sequence
<220> FEATURE:
<223> OTHER INFORMATION: in silico derived

<400> SEQUENCE: 6
catatttcaa ctatataca                                                19
```

```
<210> SEQ ID NO 7
<211> LENGTH: 21
<212> TYPE: DNA
<213> ORGANISM: Artificial Sequence
<220> FEATURE:
<223> OTHER INFORMATION: in silico derived
<220> FEATURE:
<221> NAME/KEY: misc_feature
<222> LOCATION: (20)..(21)
<223> OTHER INFORMATION: n is a, c, g, or t

<400> SEQUENCE: 7
aagtattttc aaagaatttn n                                              21

<210> SEQ ID NO 8
<211> LENGTH: 22
<212> TYPE: DNA
<213> ORGANISM: Artificial Sequence
<220> FEATURE:
<223> OTHER INFORMATION: in silico derived
<220> FEATURE:
<221> NAME/KEY: misc_feature
<222> LOCATION: (1)..(2)
<223> OTHER INFORMATION: n is a, c, g, or t

<400> SEQUENCE: 8
nnccatattt caactatata ca                                             22

<210> SEQ ID NO 9
<211> LENGTH: 17
<212> TYPE: DNA
<213> ORGANISM: Artificial Sequence
<220> FEATURE:
<223> OTHER INFORMATION: in silico derived

<400> SEQUENCE: 9
aagtattttc aaagaat                                                   17

<210> SEQ ID NO 10
<211> LENGTH: 18
<212> TYPE: DNA
<213> ORGANISM: Artificial Sequence
<220> FEATURE:
<223> OTHER INFORMATION: in silico derived

<400> SEQUENCE: 10
atatttcaac tatataca                                                  18

<210> SEQ ID NO 11
<211> LENGTH: 22
<212> TYPE: DNA
<213> ORGANISM: Artificial Sequence
<220> FEATURE:
<223> OTHER INFORMATION: in silico derived
<220> FEATURE:
<221> NAME/KEY: misc_feature
<222> LOCATION: (20)..(22)
<223> OTHER INFORMATION: n is a, c, g, or t

<400> SEQUENCE: 11
aagtattttc aaagaatttn nn                                             22

<210> SEQ ID NO 12
<211> LENGTH: 23
<212> TYPE: DNA
<213> ORGANISM: Artificial Sequence
```

```
<220> FEATURE:
<223> OTHER INFORMATION: in silico derived
<220> FEATURE:
<221> NAME/KEY: misc_feature
<222> LOCATION: (1)..(3)
<223> OTHER INFORMATION: n is a, c, g, or t

<400> SEQUENCE: 12
nnnccatatt tcaactatat aca                                              23

<210> SEQ ID NO 13
<211> LENGTH: 16
<212> TYPE: DNA
<213> ORGANISM: Artificial Sequence
<220> FEATURE:
<223> OTHER INFORMATION: in silico derived

<400> SEQUENCE: 13
aagtattttc aaagaa                                                      16

<210> SEQ ID NO 14
<211> LENGTH: 17
<212> TYPE: DNA
<213> ORGANISM: Artificial Sequence
<220> FEATURE:
<223> OTHER INFORMATION: in silico derived

<400> SEQUENCE: 14
tatttcaact atataca                                                     17

<210> SEQ ID NO 15
<211> LENGTH: 23
<212> TYPE: DNA
<213> ORGANISM: Artificial Sequence
<220> FEATURE:
<223> OTHER INFORMATION: in silico derived
<220> FEATURE:
<221> NAME/KEY: misc_feature
<222> LOCATION: (20)..(23)
<223> OTHER INFORMATION: n is a, c, g, or t

<400> SEQUENCE: 15
aagtattttc aaagaatttn nnn                                              23

<210> SEQ ID NO 16
<211> LENGTH: 24
<212> TYPE: DNA
<213> ORGANISM: Artificial Sequence
<220> FEATURE:
<223> OTHER INFORMATION: in silico derived
<220> FEATURE:
<221> NAME/KEY: misc_feature
<222> LOCATION: (1)..(4)
<223> OTHER INFORMATION: n is a, c, g, or t

<400> SEQUENCE: 16
nnnnccatat tcaactata taca                                              24

<210> SEQ ID NO 17
<211> LENGTH: 15
<212> TYPE: DNA
<213> ORGANISM: Artificial Sequence
<220> FEATURE:
<223> OTHER INFORMATION: in silico derived

<400> SEQUENCE: 17
aagtattttc aaaga                                                       15
```

```
<210> SEQ ID NO 18
<211> LENGTH: 16
<212> TYPE: DNA
<213> ORGANISM: Artificial Sequence
<220> FEATURE:
<223> OTHER INFORMATION: in silico derived

<400> SEQUENCE: 18
atttcaacta tataca                                                  16

<210> SEQ ID NO 19
<211> LENGTH: 24
<212> TYPE: DNA
<213> ORGANISM: Artificial Sequence
<220> FEATURE:
<223> OTHER INFORMATION: in silico derived
<220> FEATURE:
<221> NAME/KEY: misc_feature
<222> LOCATION: (20)..(24)
<223> OTHER INFORMATION: n is a, c, g, or t

<400> SEQUENCE: 19
aagtattttc aaagaatttn nnnn                                         24

<210> SEQ ID NO 20
<211> LENGTH: 25
<212> TYPE: DNA
<213> ORGANISM: Artificial Sequence
<220> FEATURE:
<223> OTHER INFORMATION: in silico derived
<220> FEATURE:
<221> NAME/KEY: misc_feature
<222> LOCATION: (1)..(5)
<223> OTHER INFORMATION: n is a, c, g, or t

<400> SEQUENCE: 20
nnnnnccata tttcaactat ataca                                        25

<210> SEQ ID NO 21
<211> LENGTH: 14
<212> TYPE: DNA
<213> ORGANISM: Artificial Sequence
<220> FEATURE:
<223> OTHER INFORMATION: in silico derived

<400> SEQUENCE: 21
aagtattttc aaag                                                    14

<210> SEQ ID NO 22
<211> LENGTH: 15
<212> TYPE: DNA
<213> ORGANISM: Artificial Sequence
<220> FEATURE:
<223> OTHER INFORMATION: in silico derived

<400> SEQUENCE: 22
tttcaactat ataca                                                   15

<210> SEQ ID NO 23
<211> LENGTH: 20
<212> TYPE: DNA
<213> ORGANISM: Homo sapiens

<400> SEQUENCE: 23
cacttcgtct ctggcaacaa                                              20
```

<210> SEQ ID NO 24
<211> LENGTH: 22
<212> TYPE: DNA
<213> ORGANISM: Homo sapiens

<400> SEQUENCE: 24
tgtgagcaca aagggagtag aa                                        22

<210> SEQ ID NO 25
<211> LENGTH: 261
<212> TYPE: DNA
<213> ORGANISM: Homo sapiens

<400> SEQUENCE: 25
cacttcgtct ctggcaacaa cgtcctggcc catcggtccc tgcccctttc tgaaggaggg    60
cccccactaa ggatcgccca gaggatgcgg ctggaggcaa cgcagctgga aggggttgcc   120
cgaaggatga cggcagcaca tggtctccta cagcgttcat tgtcaatgat ggggatgtcc   180
ccgatgggct gaaccttggg gcagtagtga gcgatgttga cacaggagta gtatttcttt   240
tctactccct tgtgctcac a                                             261

<210> SEQ ID NO 26
<211> LENGTH: 420
<212> TYPE: DNA
<213> ORGANISM: Homo sapiens

<400> SEQUENCE: 26
cacttcgtct ctggcaacaa cgtcctggcc catcggtccc tgcccctttc tgaaggaggg    60
cccccactaa ggatcgccca gaggatgcgg ctggaggcaa cgcagctgga aggggttgcc   120
cgaaggatga cggtggagac agattactgt ctgctgctgg ctctgccctg tggccgtgac   180
caagaggatg ttgtgagcca gaccgagtcc ctcaaggctg ccttcatcac ttacctgcag   240
gccaagcagg cggcagggat catcaacgtt cccaaccctg gctccaatca ggcagcacat   300
ggtctcctac agcgttcatt gtcaatgatg gggatgtccc cgatgggctg aaccttgggg   360
cagtagtgag cgatgttgag acaggagtag tatttctttt ctactccctt tgtgctcaca   420

<210> SEQ ID NO 27
<211> LENGTH: 20
<212> TYPE: DNA
<213> ORGANISM: Homo sapiens

<400> SEQUENCE: 27
tctgggtaca gctccctgag                                           20

<210> SEQ ID NO 28
<211> LENGTH: 20
<212> TYPE: DNA
<213> ORGANISM: Homo sapiens

<400> SEQUENCE: 28
caggggactc ctgacacttc                                           20

<210> SEQ ID NO 29
<211> LENGTH: 179
<212> TYPE: DNA
<213> ORGANISM: Homo sapiens

<400> SEQUENCE: 29
caggggactc ctgacacttc cccttcccca ccgaaccgcg tgtcggacga gcacacatac    60
agccgctcaa gccgcaggat gcgctatgcc tgcagctcct cagaggactg gcccccaccc   120
ttggacatca gctctgacgg ggacgtggat gccacggtgc tcagggagct gtacccaga    179

<210> SEQ ID NO 30
<211> LENGTH: 20
<212> TYPE: DNA
<213> ORGANISM: Homo sapiens

<400> SEQUENCE: 30
agcagtccat ccgtctcttg                                                20

<210> SEQ ID NO 31
<211> LENGTH: 20
<212> TYPE: DNA
<213> ORGANISM: Homo sapiens

<400> SEQUENCE: 31
tgatggctca gtttcccaca                                                20

<210> SEQ ID NO 32
<211> LENGTH: 161
<212> TYPE: DNA
<213> ORGANISM: Homo sapiens

<400> SEQUENCE: 32
tgatggctca gtttcccaca gctatgaatg accagcctgt gcgtggaggt ccggtatcag    60
gccactgacg gcacagtggg ctcctgggac gatggggact tcctgggaga tgagtctctt   120
caagaggaag agaaggacag ccaagagacg gatggactgc t                       161

<210> SEQ ID NO 33
<211> LENGTH: 20
<212> TYPE: DNA
<213> ORGANISM: Homo sapiens

<400> SEQUENCE: 33
aagcagagaa cgagagaggc                                                20

<210> SEQ ID NO 34
<211> LENGTH: 20
<212> TYPE: DNA
<213> ORGANISM: Homo sapiens

<400> SEQUENCE: 34
tgtccatcac tgaggagacc                                                20

<210> SEQ ID NO 35
<211> LENGTH: 181
<212> TYPE: DNA
<213> ORGANISM: Homo sapiens

<400> SEQUENCE: 35
cttctaacga tgacgatatt cgcgctctcg gtcacgctct cggtcacggt ctcggtcacg    60
atcccggtgc ctctctcgtt ctctgcttaa gaggtgacca agaatatggc ccaggtgacc   120
aaagccctgg acaaggccct gagcaccatg gacctgcaga aggtctcctc agtgatggac   180
a                                                                   181

```
<210> SEQ ID NO 36
<211> LENGTH: 26
<212> TYPE: DNA
<213> ORGANISM: Homo sapiens

<400> SEQUENCE: 36
atgccgccca aaccccccg aaaaac                                       26

<210> SEQ ID NO 37
<211> LENGTH: 23
<212> TYPE: DNA
<213> ORGANISM: Homo sapiens

<400> SEQUENCE: 37
ctcctcctag aataacacct gca                                         23

<210> SEQ ID NO 38
<211> LENGTH: 315
<212> TYPE: DNA
<213> ORGANISM: Homo sapiens

<400> SEQUENCE: 38
tgcaccatac caggcttcct tctttggcca ccggtaccac atcatctggg tccaatactc      60
catccacaga tgaaactttc tcccaagtta accaagctct ctctctgaca tgatctggta     120
tctttaattt ctgacataat gcagtaaaat caggttcttc tgtttcttca aactcaagcc     180
tgacgagagg caggtcctcc gggccgctgt cctgctctgg gtcctcctca ggaggggcg      240 gcggcggcgg tgccgggggt tccgcggcgg cagcggcggc ggtggcggcc gtttttcggg     300
gggttttggg cggca                                                     315
```

ACCURATE AND SENSITIVE UNVEILING OF CHIMERIC BIOMOLECULE SEQUENCES AND APPLICATIONS THEREOF

CROSS REFERENCE TO RELATED APPLICATIONS

This application is a national stage of PCT Patent Application No. PCT/US2018/018844, entitled "Accurate and Sensitive Unveiling of Chimeric Biomolecule Sequences and Applications Thereof" to Julia Salzman, filed Feb. 20, 2018, which claims priority to U.S. Provisional Application Ser. No. 62/460,708, filed Feb. 17, 2017, which is incorporated herein by reference in its entirety.

STATEMENT REGARDING FEDERALLY SPONSORED RESEARCH OR DEVELOPMENT

This invention was made with Government support under contracts CA168987 and GM116847 awarded by the National Institutes of Health. The Government has certain rights in the invention.

REFERENCE TO A SEQUENCE LISTING SUBMITTED ELECTRONICALLY VIA EFS-WEB

The instant application contains a Sequence Listing which has been filed electronically in ASCII format and is hereby incorporated by reference in its entirety. Said ASCII copy, created on Feb. 15, 2018, is named 04864 Seq File_ST25.txt and is 9,329 bytes in size.

FIELD OF THE INVENTION

The invention is generally directed to a various applications related to biological chimeras, and more specifically to methods and systems for unveiling chimeric biomolecule sequences and applications thereof.

BACKGROUND

Somatic mutations can arise within an animal cell, leading to neoplasia and tumorgenesis. Gene fusions are a characteristic somatic mutation that may result in chimeric genetic molecules. Here, chimeric genetic molecules are defined as biomolecules (e.g., DNA, RNA, protein) having sequences consisting of sequences from distinct loci that cannot be explained by read-through transcription of the reference genome. Chimeric RNA molecules could be linear or circular and arise from a variety of biochemical processes in the cell such as cis or trans-splicing (Li et al., Science, 321:1357-61, 2008, the disclosure of which is incorporated herein by reference in its entirety); they could arise from transcription from the reference genome (and be spliced into a circular RNA) or from a genomic rearrangement. The most well studied chimeric RNA type is fusion mRNA, spliced in cis from a genomic rearrangement specific to a mutation-bearing cell. However, any combination of rearrangement events at multiple levels of genetic expression could in principle give rise to a chimeric biomolecules.

Chimeric biomolecules are often found to exist within transformed cells or a neoplasm. In fact, many chimeric products have been found to be pathogenic in tumor formation and cancer. The discovery of oncogenic gene fusions, including BCR-ABL1 in chronic myelogenous leukemia (CML) and the FLT3 internal tandem duplication in acute myelogenous leukemia (AML), have provided critical insights into pathogenesis and led to important therapeutic advances (Weisberg et al., Cancer Cell 1:433-43, 2002; Druker et al., New Eng J Med 344(14):1031-37, 2011; the disclosures of which are incorporated herein by reference in their entirety). Recurrent gene fusions have also been identified in commonly occurring solid tumors (Tomlins et al., Science 310:644-48, 2005, the disclosure of which is incorporated herein by reference in its entirety) and the EML4-ALK family in lung cancer (Soda et al., Nature 448:561-66, 2007, the disclosure of which is incorporated herein by reference in its entirety).

Prior to the advent of next-generation sequencing, many fusions, including those mentioned above, were found using cytogenetics or candidate-based methodologies. Since that time, a variety of gene fusions have been discovered using DNA- and RNA-Seq (Singh et al., Science 337:1231-35, 2012; Ju et al., Genome Res 22:436-45, 2012; Carneiro et al., Gynecol Oncol Reports 13:53-56, 2015; the disclosures of which are incorporated herein by reference in their entirety). Next-generation sequencing focused fusions involving known oncogenes, has enabled discovery of fusions in a variety of other cancers that can be targeted with existing drugs, such as FGFR, ALK, and ROS family gene fusions (Halasi et al., Biochemistry 454:201-08, 2013; Stransky et al., Nat Commun 5:e5846, 2014; Gozgit et al., Mol Cancer Ther 11(3):690-99, 2012; the disclosures of which are incorporated herein by reference in their entirety).

SUMMARY OF THE INVENTION

Systems and methods are disclosed that use statistical methodologies, data structure construction, and efficient querying of data structures to unveil chimeric biomolecule sequences from various sequence data sets. Many embodiments of the invention incorporate a method for unveiling chimeric biomolecule sequences using a computing system. The method obtains a plurality of discordant biomolecule sequence read pairs each having a genetic distance between each read greater than a defined threshold. A discordant read pair signifies the possibility of a fusion junction of a chimeric biomolecule. The method also obtains a plurality of unaligned biomolecule reads that did not align to a reference sequence index as determined by an alignment score, each unaligned read having a paired read. The method also classifies each read pair having an unaligned read as 'consistent' if able to align to a fusion junction sequence in a fusion index and 'inconsistent' if only one read is able to align to a fusion junction sequence in the fusion index. The fusion index includes a plurality of discordant read pairs. The method also classifies each read pair having an unaligned read as 'artifactual' if able to align to an indel sequence in an indel index. The indel index includes a set of indel sequences for each fusion junction sequence of the fusion index. The method also fits a generalized linear model (GLM) for each read, including the 'consistent', 'inconsistent' and 'artifactual' read pairs, to estimate each read's probability that its alignment to a fusion junction sequence was due to an artifact. Each read's probability is predicted by alignment score, mapping quality, and the amount of junction overlap. The method also generates a cumulative probability score for each fusion junction sequence by aggregating each read's estimated probability. The method also assigns a junction score to each fusion junction by comparing the cumulative probability score for each fusion junction to a null junction score distribution. The method also assigns an empirical p value for each fusion junction by its junction score to an empirical p value null. The empirical p value reflects the likelihood that the fusion junction is an artifact. The method also produces a report of at least one fusion junction with its assigned empirical p value.

In more embodiments, the method, using the computing system, also obtains biomolecule sequence data having a plurality of paired sequence reads. The method also aligns each sequence read of the plurality of read pairs to at least one reference sequence index. Each read is classified as 'aligned' or 'unaligned'. A read pair have two aligned reads having a genetic distance between each read. The method also classifies the plurality of read pairs as discordant when the genetic distance between each read of a read pair is greater than the defined threshold. A discordant read pair signifies the possibility of a fusion junction of a chimeric biomolecule.

In further embodiments, the at least one reference sequence index includes an index including genomic DNA sequences.

In further more embodiments, the at least one reference sequence index includes an index including exon-exon junction sequences.

In even more embodiments, the biomolecule data is trimmed and processed.

In even further embodiments, the biomolecule sequence data includes paired-end sequencing data.

In even further more embodiments, the biomolecule sequence data includes split-read sequencing data.

In yet even further more embodiments, the biomolecule sequence data is derived de novo, derived from a public or private database, or generated in silico.

In still yet even further more embodiments, the biomolecule sequence data includes DNA from at least a partial genome.

In still yet even further more embodiments, the biomolecule sequence data includes RNA from at least a partial transcriptome.

In still yet even further more embodiments, the method, using the computing system, also identifies and removes fusion junctions that are homologous to known splicing events.

In still yet even further more embodiments, the known splicing events are derived from a publically available reference genome having junction indices.

In still yet even further more embodiments, the method, using the computing system, also identifies and removes fusion junctions that are homologous to cryptic splicing events.

In still yet even further more embodiments, the cryptic splicing events are removed when the 5' and 3' ends of each fusion are within a defined genetic distance.

In still yet even further more embodiments, the defined genetic distance is selected from the group consisting of 10 kilobases (kb), 25 kb, 50 kb, and 100 kb.

In still yet even further more embodiments, the defined threshold is selected from the group consisting of, 25 kb, 50 kb, 100 kb and 200 kb.

In still yet even further more embodiments, the alignment score is calculated by Bowtie2.

In still yet even further more embodiments, the method, using the computing system, also builds the fusion index including the plurality of fusion junction sequences derived from the plurality of discordant read pairs. Each of the plurality of fusion junction sequences are an exon-exon boundary of two discordant exons identified by the discordant read pairs. Each of the plurality of fusion junction sequences signifies a candidate chimeric biomolecule.

In still yet even further more embodiments, the method, using the computing system, also builds the indel index including the set of indel sequences for each fusion junction sequence of the fusion index. Each set of indel sequences includes a plurality of 5' junction sequences having at least one insertion at the junction breakpoint, a plurality of 3' junction sequences having at least one insertion at the junction breakpoint, a plurality of 5' junction sequences having at least one deletion at the junction breakpoint, and a plurality 3' junction sequences having at least one insertion at the junction breakpoint.

In still yet even further more embodiments, the GLM is fitted using the command:

x=glm(is.pos~overlap+lenAdjScore+qual+lenAdjScoreR2+qualR2, data=readPredictions, family=binomial(link="logit"), weights=readPredictions[,cur_weight])

Where is.pos is 1 for "consistent" reads and 0 for "inconsisten" reads, overlap is a minimum number of nucleotides that flank each side of the junction breakpoint, qualR2 are mapping qualities, and lenAdjScoreR2 is an adjusted alignment score.

In still yet even further more embodiments, the null junction score is constructed for each value of the number of reads aligning to the fusion by randomly sampling from the empirical distribution of probability that a read is an artifact for all reads in the obtained sequencing reads.

In still yet even further more embodiments, the null junction score is constructed for each value of the number of reads aligning to the fusion junction using the Hoeffding combinatorial central limit theorem.

In still yet even further more embodiments, the empirical p value for each fusion junction is estimated by referring its junction to an empirical distribution of junction scores of mappable fusion junctions.

In still yet even further more embodiments, the report includes the junction score of the at least one fusion junction.

In still yet even further more embodiments, the method, using the computing system, also generates at least one bloom filter query incorporating at least one fusion junction The method also applies the at least one bloom filter query to a hierarchical bloom filter tree data structure.

In still yet even further more embodiments, the method, using the computing system, also constructs the hierarchical bloom filter tree data structure.

In still yet even further more embodiments, the biomolecule sequence data is derived from a large database.

In still yet even further more embodiments, the large database is The Cancer Genome Atlas (TCGA).

In still yet even further more embodiments, the report is used to prioritize a candidate chimeric biomolecule for further development of one of research tools, diagnostics, or medicaments.

In still yet even further more embodiments, the report is used to select a candidate chimeric biomolecule to be used as a template to create a synthetic nucleic acid polymer that includes the sequence of the candidate chimeric biomolecule.

In still yet even further more embodiments, the report is used to select a candidate chimeric biomolecule to be used as a template to create a synthetic nucleic acid polymer that includes the complementary sequence of the candidate chimeric biomolecule.

In still yet even further more embodiments, the report is used to select a candidate chimeric biomolecule to be used as a template to create an expression vector to express the candidate chimeric biomolecule in a suitable expression system.

In still yet even further more embodiments, the report is used to select a candidate chimeric biomolecule to develop a biomarker to detect the candidate chimeric biomolecule.

In still yet even further more embodiments, the biomarker is used to diagnose a biological sample In still yet even further more embodiments, the report is used to select a candidate chimeric biomolecule to develop a drug screening platform utilizing to genetically modified cells that incorporate the candidate chimeric biomolecule.

In still yet even further more embodiments, the report is used to select a candidate chimeric biomolecule to develop an antigen-binding molecule with high specificity, preference and affinity for the candidate chimeric biomolecule.

In still yet even further more embodiments, the antigen-binding molecule is a polyclonal antibody.

In still yet even further more embodiments, the antigen-binding molecule is a monoclonal antibody.

Many embodiments are directed to method to query a hierarchical bloom tree data structure utilizing candidate chimeric biomolecule sequences using a computing system. The method obtains a hierarchical bloom filter tree data structure incorporating a number of compressed bloom filters. The bloom filters are organized within the bloom tree data structure in a hierarchical manner beginning with a root bloom filter, continuing with a plurality of intermediate bloom filters, and ending with a plurality of leaf bloom filters. Each leaf includes an experimental set of sequence data. Each intermediate bloom filter and the root bloom filter is a parent bloom filter associated with a binary node of the hierarchical bloom filter tree data structure such that each parent bloom filter has two downstream child bloom filters. Each bloom filter includes a set of k-mers such that each parent bloom filter incorporates the subset of k-mers of each of its children bloom filters and the root bloom filter incorporates the entire collection of k-mers. The method also obtains at least one biomolecule sequence query that includes at least one candidate chimeric biomolecule sequence. The method also breaks each of the at least one biomolecule sequence queries into a set of k-mers. The method also applies the at least one biomolecule sequence query to the hierarchical bloom filter tree data structure starting with the root bloom filter. The k-mers of the at least one biomolecule sequence query are queried at each parent node by determining whether the k-mers of the at least one biomolecule sequence query are present in the parent node associated bloom filter. A positive match between the k-mers of the at least one biomolecule sequence query and the k-mers of the parent node associated bloom filter results in a query of the two downstream child bloom filters. No match between the k-mers of the at least one biomolecule sequence query and the k-mers of the parent node associated bloom filter results in pruning the two downstream children bloom filters and their progeny. The method also detects the at least one candidate chimeric biomolecule sequence in at least one experimental set of sequence data. A positive match between the k-mers of the at least one biomolecule sequence query and the k-mers of a particular leaf provides that the at least one candidate chimeric biomolecule sequence of the associated with the at least one biomolecule sequence query exists within the experimental set of sequence data associated with the particular leaf. The method also produces a report indicating the detection of the at least one candidate chimeric biomolecule sequence in the at least one experimental set of sequence data.

In more embodiments, each bloom filter includes a bit vector having a length and a set of hash functions that map the k-mers to bits in the bit vector.

In further embodiments, the k-mers are a length selected from 17, 18, 19, 20, 21, 22, 23, 24, or 25 nucleotides.

In further more embodiments, at least one experimental set of sequence data is derived from a sequencing experiment on a neoplasm.

In even more embodiments, the sequencing experiment on the neoplasm is derived from The Cancer Genome Atlas (TCGA).

In even further embodiments, the positive match between the k-mers of the at least one biomolecule sequence query and the k-mers of the parent node associated bloom filter is determined by a k-mer threshold.

In even further more embodiments, the k-mer threshold is uniform for all nodes in the hierarchical bloom filter tree data structure.

In yet even further more embodiments, the hierarchical bloom filter tree data structure is obtained by constructing, using the computing system, the hierarchical bloom filter tree data structure.

In still yet even further more embodiments at least one candidate chimeric biomolecule sequence is unveiled by using the computing system to obtaining a plurality of discordant biomolecule sequence read pairs each having a genetic distance between each read greater than a defined threshold. A discordant read pair signifies the possibility of a fusion junction of a chimeric biomolecule. The computing system also obtains a plurality of unaligned biomolecule reads that did not align to a reference sequence index as determined by an alignment score, each unaligned read having a paired read. The computing system also classifies each read pair having an unaligned read as 'consistent' if able to align to a fusion junction sequence in a fusion index and 'inconsistent' if only one read is able to align to a fusion junction sequence in the fusion index. The fusion index comprises a plurality of discordant read pairs. The computing system also classifies each read pair having an unaligned read as 'artifactual' if able to align to an indel sequence in an indel index. The indel index comprises a set of indel sequences for each fusion junction sequence of the fusion index. The computing system also fits a generalized linear model (GLM) for each read, including the 'consistent', 'inconsistent' and 'artifactual' read pairs, to estimate each read's probability that its alignment to a fusion junction sequence was due to an artifact. Each read's probability is predicted by alignment score, mapping quality, and the amount of junction overlap. The computing system also generates a cumulative probability score for each fusion junction sequence by aggregating each read's estimated probability. The computing system also assigns a junction score to each fusion junction by comparing the cumulative probability score for each fusion junction to a null junction score distribution. The computing system also assigns an empirical p value for each fusion junction by its junction score to an empirical p value null. The empirical p value reflects the likelihood that the fusion junction is an artifact. The computing system also produces a report of at least one fusion junction with its assigned empirical p value.

Many embodiments are directed to a method for constructing a hierarchical bloom tree data structure using a computing system. The method obtains a plurality of experimental biomolecule sequence data sets having a plurality of sequence reads. The method also breaks each of the plurality of experimental biomolecule sequence data sets into k-mers. The method also assigns the k-mers of each of the plurality of experimental biomolecule sequence data sets into leaf bloom filters. The method also constructs and layers parental bloom filters to create the hierarchical bloom tree data structure having a root node, a plurality of intermediate nodes, and a plurality of leafs. The bloom filters are organized within the bloom tree data structure in a hierarchical manner beginning with a root bloom filter, continuing with a plurality of intermediate bloom filters, and ending with a plurality of leaf bloom filters. Each leaf includes an experimental set of sequence data. Each intermediate bloom filter and the root bloom filter is a parent bloom filter associated with a binary node of the hierarchical bloom filter tree data structure such that each parent bloom filter has two downstream child bloom filters. Each bloom filter includes a set of k-mers such that each parent bloom filter incorporates the subset of k-mers of each of its children bloom filters and the root bloom filter incorporates the entire collection of k-mers. The method also stores the hierarchical bloom tree data structure in a memory.

In more embodiments, each bloom filter comprises a bit vector having a length and a set of hash functions that map the k-mers to bits in the bit vector.

In further embodiments, the k-mers are a length selected from 17, 18, 19, 20, 21, 22, 23, 24, or 25 nucleotides.

In further more embodiments, at least one of the plurality of experimental sets of sequence data is derived from a sequencing experiment on a neoplasm.

In even more embodiments, the sequencing experiment on the neoplasm is derived from The Cancer Genome Atlas (TCGA).

In even further embodiments, the hierarchical bloom tree data structure is used to detect a candidate chimeric biomolecule sequence the plurality of experimental sets of sequence data.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 6B illustrates a process for constructing a hierarchical tree data structure in accordance with an embodiment of the invention.

FIG. 12 illustrates an example of mappable chimeric sequence reads in accordance with various embodiments of the invention.

FIG. 15 illustrates a chart detailing chimeric sequence unveiling sensitivity and accuracy of various methodologies generated in accordance with a number of embodiments of the invention.

FIG. 19 illustrates charts detailing chimeric sequence unveiling sensitivity and accuracy of various methodologies generated in accordance with a number of embodiments of the invention.

DETAILED DESCRIPTION

Figure 1:
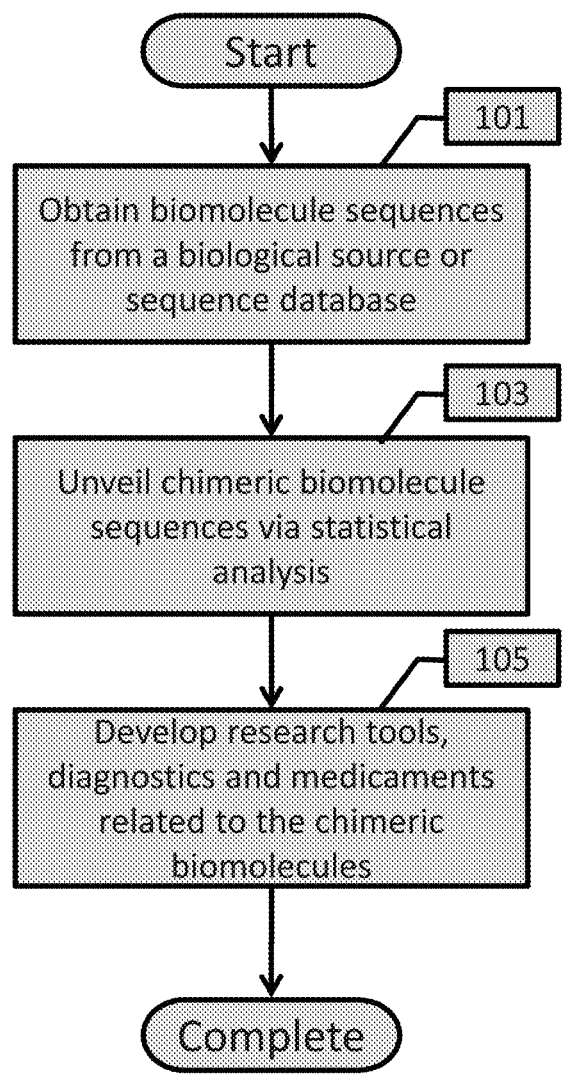
FIG. 1 illustrates a process for unveiling chimeric biomolecule sequences and developing research tools, diagnostics and medicaments in accordance with an embodiment of the invention.

Turning now to the drawings and data, a number of processes for biomarker discovery that can be utilized in diagnostic and medicament development in accordance with various embodiments of the invention are illustrated. In several embodiments, a process encompasses computational unveiling of novel chimeras existing within a particular genome or expressed within a given transcriptome. These hidden chimeras may be undiscoverable by heuristic, ad hoc methodologies. Various embodiments of the current invention, however, are capable of discovering chimeras using an unbiased, a priori methodology. Once unveiled, chimeric biomolecules can be synthesized and used in a variety of applications, especially for the use of diagnostics and medicaments.

Historically, chimeric genetic elements were found using cytogenetics or candidate-based methodologies. With the advent of next-generation sequencing, chimeras could be revealed within the sequencing results of a cellular genome, transcriptome, or proteome. Analysis of this data, however, has been inadequate and often resulted in inaccurate or insensitive discovery of chimeras due to human-guided filtering and heuristic approaches to cull these chimeras. This format of analysis is problematic because it will result in systematic false positives and lack of sensitivity can result in true positives being left veiled. Due to the inadequate analysis, it is likely chimeric biomolecules expressed in several human cancers remain veiled.

For this reason, there is a pressing need for robust methods to unveil chimeric genetic elements with low false positive rates. Chimera detection methods with high false positive rates are unfit for use in clinical sequencing applications, as time and resources may make it impractical to manually scrutinize a list of gene fusion candidates and/or perform secondary validations. Further, in clinical samples, it may be impractical or impossible to perform secondary tests of predictions due to limited amount of chimeric biomolecule source.

A robust method of chimera discovery with a low false positive rate can also be used to mine thousands of publicly available biomolecule sequence datasets from tumor samples (e.g., RNA-seq datasets). These datasets may harbor veiled oncogenes, drug targets and/or gene fusions, including oncogenes that promote cancer progression.

Methods and embodiments of the invention described herein are capable of overcoming the problems associated with typical approaches to chimera detection. One such embodiment is a method entitled MACHETE (Mismatched Alignment CHimEra Tracking Engine), which is a novel, sensitive and highly specific method to detect fusion biomolecules from genetic data. In some embodiments, MACHETE is used to detect chimeric RNAs at annotated exon-exon boundaries from RNA-Seq data. This method significantly extends on a previous computational framework developed to detect circular and linear RNA splicing, which is described in Szabo et al., (*Genome Biol* 16:126, 2015, the disclosure of which, including the description of the KNIFE process, is incorporated herein by reference in its entirety). As described below, many embodiments of the invention, including MACHETE, incorporate novel computational and statistical methodologies. For example, various embodiments leverage statistical modeling to prioritize chimeric biomolecules. In numerous embodiments, false positives are removed while retaining the ability to identify true positives. In several cases, the methods described herein can unveil chimeras missed by other methods common in the field. Accordingly, a number of embodiments of the invention utilize an unbiased, a priori method to mine already available datasets and unveil previously undiscoverable chimeras.

In several embodiments, an empirical p-value allows for the prioritization of chimeric sequences for clinical and research validation. This is an innovation absent in previous methods, which only prioritize potentially oncogenic events by read count, lacking statistical interpretation.

In many embodiments, methods to unveil chimeric sequences are scalable. For example, MACHETE is scalable (sMACHETE) when combined with short sequence data structures (e.g., Sequence Bloom Trees; for more, see Solomon and Kingsford bioRxiv 017087 (doi: https://doi.org/10.1101/017087); and Solomon and Kingsford, *Nat Biotechnol.*, 34:300-02, 2016; 2016, the disclosures of which are incorporated herein by reference in its entirety). The combined approach enables screening of extremely large datasets. MACHETE is sensitive and highly specific, but would take too long to run across large data sets, such as The Cancer Genome Atlas (TCGA). sMACHETE is a direct extension of MACHETE that implements sequence-read reducing filters (e.g., bloom filters) and additional modeling to maintain accuracy but improve performance. It should be understood that text-data reading filters, such as globally search a regular expression and print (grep) can be incorporated in addition to, or in replace of, the sequence-read reducing filters. As can readily be appreciated, any of a variety of filters can be utilized as appropriate to the requirements of a given application.

An unbiased method to unveil chimeric biomolecules holds significant promise in the field of cancer research and clinical development. Chimeric DNA, RNA and chimeric proteins are great candidates for development of biomarkers, diagnostics, druggable targets, and neoantigens. Chimeric proteins can be specific drug targets and are the basis for some of the most effective cancer therapies available today. Other chimeric molecules can function by inactivating a tumor suppressor (McNerney et al., *Blood*, 121:975-83, 2013, the disclosure of which is incorporated herein by reference in its entirety), or providing dominant gains of functions at the RNA or protein level (Tay et al., *Cell*, 147:344-57, 2011, the disclosure of which is incorporated herein by reference in its entirety). While recurrence of gene fusions is a hallmark of a selective event during tumor initiation, and has been a historical proxy for a chimera driving a cancer, private or very rare chimeric genetic elements are beginning to be appreciated as functional drivers (Latysheva and Babu, *Nucleic Acids Research*, 44:4487-503, 2016; Ni and Kuperwasser, *eLife*, 5(May 2016); the disclosures of which are incorporated herein by reference in its entirety).

Chimeric biomolecules, including fusion messenger RNAs, have the potential to provide fundamental insights into and discovery of new functions for genes and biochemical pathways (Kadoch and Crabtree, *Cell*, 153: 71-85, 2013, the disclosure of which is incorporated herein by reference in its entirety). In clinical applications, chimeric, cancer-specific biomolecules can be among the most sensitive and specific biomarkers. Thus, the unveiling novel chimeric gene sequences from either genomic DNA or RNA transcripts could yield better diagnostics when detected in a patient biopsy. Processes and the development of research tools, diagnostics, and medicaments in accordance with various embodiments of the invention are discussed further below.

Chimeric Biomolecule Process Overview

An embodiment of a process to develop research tools, diagnostics, and medicaments is illustrated in FIG. 1. This embodiment is directed to unveiling chimeric genes and applies the knowledge garnered to applications related to the chimeras. For example, this pipeline can be used to develop research tools, diagnostics and medicaments related to chimeric molecules that exist in a disease state, such as, for example, cancer.

Process 100 can begin with obtaining (101) biomolecule sequences from a biological source or sequence database. In many embodiments, the biomolecule sequences to be obtained are RNA molecules, such as a transcriptome from a particular biological source. However, the biomolecule sequences could also be derived from DNA molecules or protein molecules, such as a genome or proteome. In many embodiments, biomolecule sequences are obtained de novo by extracting the molecules from a biological source and sequencing them. Alternatively, biomolecule sequences can be obtained from a publicly or privately available database. Many databases exist that store datasets of sequences from which a user can extract the data to perform analysis upon.

In many embodiments, a de novo source of biomolecules for sequencing is a biological source for which a user desires to unveil chimeric sequences, such as from an animal cell sample or a tissue biopsy. In particular embodiments, biomolecules to be acquired can be derived from biopsies of human patients associated with a phenotype or disease state, such as cancer, for example. In several embodiments, biomolecules are derived from biological sources utilized in research, such as in vitro tissue culture cell lines or research mouse models. In many cases, biomolecules are extracted, processed and sequenced according to methods commonly understood in the field.

Process 100 unveils (103) chimeric sequences that exist within obtained sequence datasets via statistical analysis that leverages artifactual data. For example, a priori, Bayesian, frequentist, or other appropriate statistical analysis can be performed. Chimeric sequences can be found within various sequence reads, and statistical analysis can be performed to determine whether these chimeric sequences are from bona fide chimeric biomolecules from its host source. Chimeric sequences can be reported and ascertained for further development.

Utilizing unveiled chimeric sequences, research tools, diagnostics, and medicaments can be developed (105). Chimeric nucleic acids and proteins can be synthesized and utilized in downstream applications. Many of these applications include further research on the unveiled chimeras. In addition, synthetic chimeras can serve to develop research and clinical tools to recognize the chimera in various applications. In a number of embodiments, a synthetic chimeric nucleic acid could be used to develop a hybridization assay to identify the existence of chimeric DNA or RNA molecules in a biological sample or medical biopsy. In many embodiments, a synthetic chimeric peptide chain could be utilized to develop an immunological assay to identify the existence of a chimeric protein in a biological sample or medical biopsy. In several embodiments, synthetic chimeric molecules are utilized to develop drugs and medications that key in on naturally occurring chimeras in a patient.

Chimeric biomolecules can be associated with several phenotypes and disease states. As such, process 100 can be employed to develop research tools, diagnostics and medicaments for many different types of diseases. In particular, chimeric RNA and protein molecules have a high occurrence in neoplastic phenotypes, such as those found in tumors and cancers. The relatively high abundance of chimeric molecules in neoplasms and cancers suggest that unveiling of novel chimeric sequences and developing downstream products would greatly enhance the research, diagnosis, and treatment of many cancers.

Chimeric Sequence Unveiling

Figure 2:
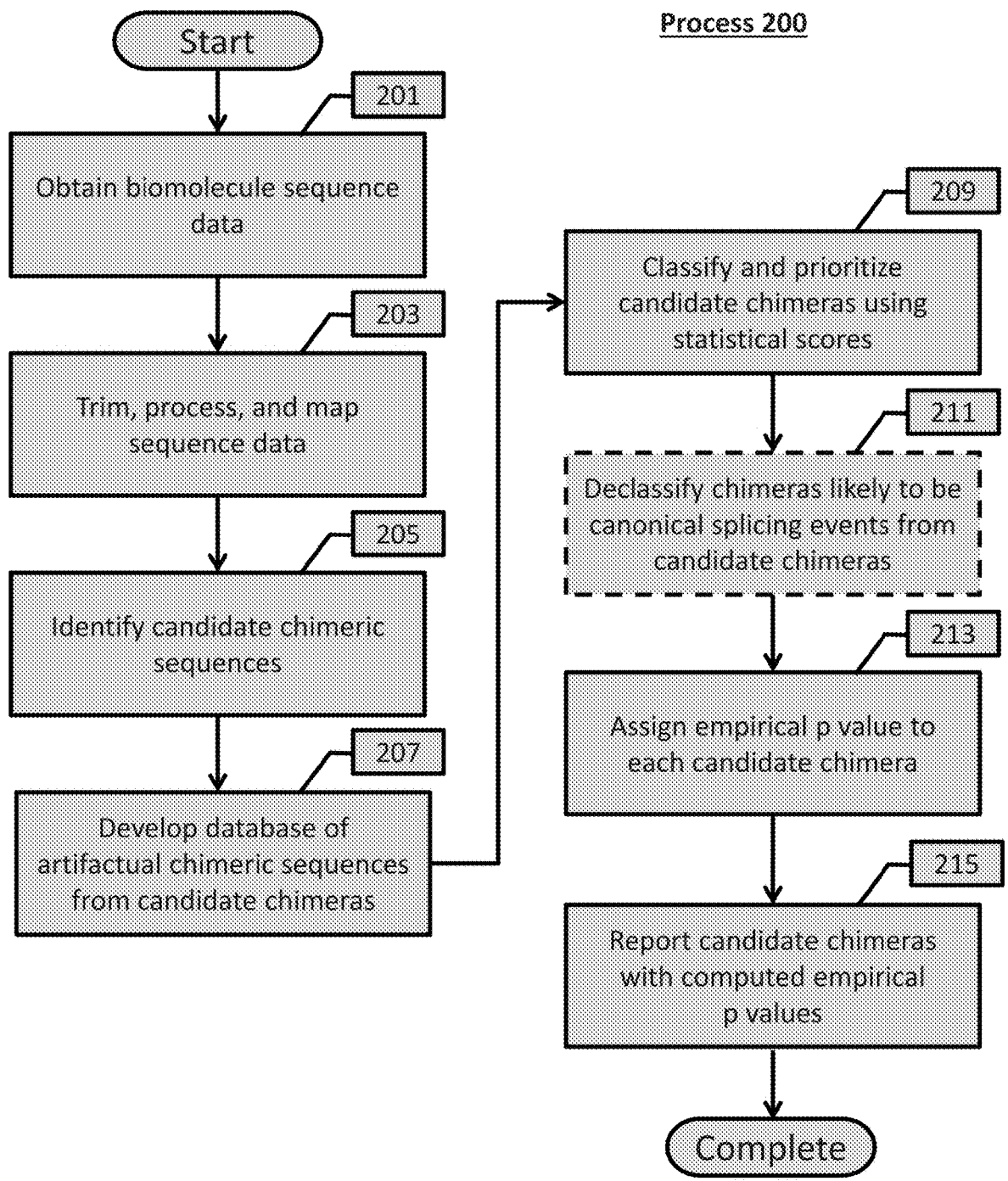
FIG. 2 illustrates a process for unveiling chimeric biomolecule sequences in accordance with an embodiment of the invention.

A process for unveiling chimeric sequences in accordance with an embodiment of the invention is shown in FIG. 2. Process 200 obtains (201) biomolecule sequence data. In several embodiments, this sequence data is derived from RNA that is derived from at least a partial transcriptome and sequenced in a next-generation sequencing platform, such as those manufactured by Illumina, Inc. of San Diego, Calif. In some embodiments, this sequence data is derived from DNA that is derived from at least a partial genome and sequenced in a next-generation sequencing platform. It should be understood, however, that sequence data could also be derived from proteins or peptides, such as from at least a partial proteome. For chimera unveiling applications described within, RNA sequencing provides a facile method to obtain sequence data, as it is typically abundant in a biological source, can be easily sequenced by known methods, readily available in numerous public and private databases, has intronic sequences already removed, and many exon reference databases exist for post-sequencing analysis. As can readily be appreciated, any of a variety of sequencing technologies can be utilized to obtain biomolecule sequence data as appropriate to the requirements of a given application.

The source of biomolecule sequence data can be derived de novo (i.e., from a biological source), from a public or private database, or generated in silico. Several methods are well known to derive biomolecule sequence data from biological sources. Generally, biomolecules are extracted from tissue, prepped to be sequenced, and then run on a sequencer. For example, RNA can be extracted from a human tissue source such as a biopsy, then prepped into a sequence library using standard techniques, and sequenced on a next-generation sequencing platform, such as those manufactured by Illumina. Likewise, biomolecule sequence data can be derived from an available database. For example, transcriptome data can be obtained from the National Center for Biotechnology Information (NCBI) Reference Sequence (RefSeq) or TCGA databases. In addition, sequences to be analyzed can be generated in silico, by any appropriate computational methods. It should be noted that the sequence data could be in any appropriate sequence read format, including (but not limited to) single or paired-end reads.

Process 200 trims, processes, and maps (203) biomolecule sequence data. Many methodologies are known to process sequence data, and any appropriate method can be used. For example, the sequence data can be trimmed from the publicly available TrimGalore (http://www.bioinformatics.babraham.ac.uk/projects/trim_galore/) or cutAdapt (https://code.google.com/p/cutadapt/) methods, which remove adapter sequences and trim poor-quality bases. Mapping can be performed with any appropriate annotated genome, such as, for example, UCSC's hg19 (http://support.illumina.com/sequencing/sequencing_software/igenome.html) and alignment tool, such as, for example, Bowtie2

(http://bowtie-bio.sourceforge.net/bowtie2/index.shtml). Processing of the data will be dependent on the user's goal, and thus is adaptable to the results desired. One possible example of a method to process data is Known and Novel IsoForm Explorer (KNIFE), which is fully detailed in Szabo, et al. (Szabo et al., cited supra). Although only a few methods of trimming, processing, and mapping sequence data are disclosed, it should be understood many more methods exist and would be covered by various embodiments of the invention.

Process 200 nominates (205) candidate chimeric biomolecule sequences. Chimeric sequences, as provided in this disclosure, are sequences consisting of sequences from distinct loci that cannot be explained by read-through transcription of the reference genome. These chimeras can include annotated and unannotated exon-exon junctions. Accordingly, these may arise from any rearrangement process, such as cis or trans-splicing, splicing into a circular RNA, or genomic rearrangement.

Candidate chimeric molecules can be nominated from discordant spanning reads of paired-end read data or split single reads (e.g., reads of only one end of a paired-end read). Discordant spanning reads arise when one end of the read maps to a first locus in the genome and the other end maps to a second distant locus in the genome. The distance in which the discordant read become a candidate chimeric molecule can be dependent on the definition provided by a user. In theory, a chimeric molecule could arise from a small deletion (e.g. 25 kb), especially in gene rich areas of the genome. On the other hand, some genes in the human genome have extremely large introns, with some exceeding 50 kb. Thus, an appropriate threshold can be dependent on the balance of excluding possible chimeras due or nominating some candidate chimeras that are linear canonical splicing events. Accordingly, the appropriate distance varies, and could be, for example, 25, 50, 100, or 200 kb. As can readily be appreciated, the specific distance used in a specific context is largely dependent upon the requirements of a given application.

Split single reads can also nominate candidate chimeric sequences. Split reads are reads in which one end of the read maps to one locus in the genome and the opposite end of the read maps to a distant locus. The precise definition of a read can vary and nomination of split reads as chimeric sequences can be dependent on predetermined requirements and/or user definitions. For example, the definition of a qualified alignment to the genome can vary and may be dependent on the read length. Ideally, the read would be long enough to confidently assign both ends of the read to two separate loci. The greater the length of the read alignment to the genome, the more likely the read is accurate. Accordingly, embodiments are directed to methods that utilize reads of appropriate length. In some of these embodiments, the read is at least 50 bases, with each fragment alignment having at least 25 bases. In several embodiments, the read is at least 70 bases, with fragments of at least 35 bases; or at least 100 bases, with fragments of at least 50 bases. In addition, the fragments in the split read can be of different sizes (e.g., 100 base read, and 30 and 70 base fragments). In more embodiments, identification of spice sites can help nominate and filter potential chimeric sequences.

Process 200 develops (207) an artifactual chimeric sequence database using a plurality of the candidate chimeras. In several embodiments, an artifactual chimeric sequence database is a collection of chimeras that arise from library preparation, not due to natural biological processes (i.e., genomic rearrangement, splicing mechanisms). Artifactual chimeras may arise from a variety of mechanisms during in vitro manipulation, including (but not limited to) mistakes in transcription or ligation to prepare cDNA libraries. For example, when RNA is reverse-transcribed into cDNA, the reverse transcriptase can initiate transcription on one RNA strand, dissociate, and associate with another RNA strand and continue transcription. This mistake likely results in cDNA molecule having two exonic sequences from disparate loci in the genome, and thus can be nominated as a candidate chimera. Alternatively, when DNA adapters are ligated to the ends of cDNA, a mistake can occur during the process that results in two cDNA ligating together, likely with exonic sequences from disparate loci. Artifactual chimeras due to in vitro library preparation can veil bona-fide, naturally occurring RNA chimeras, and thus, it is ideal to remove these artifacts.

In various embodiments, artifactual chimeras can be revealed by modeling the rate of chimeric artifact occurrence. For each candidate chimeric sequence, the likelihood that the candidate is an artifact can be modeled via a realistic simplifying assumption that a read that is generated in vitro is equally likely to have a spurious fusion breakpoint at any point along the transcript. Thus, the breakpoint is not biased to occur at or near a typical splice event (i.e., exon-exon junction). To model spurious breakpoints, an insertion-deletion (indel) chimeric database/index can be created. This database can include several generated indel chimeras for each candidate chimera. Although an indel database to model spurious breakpoints is described here to reveal artifactual chimeras, it should be understood that other adequate methods to reveal artifactual chimeras, such as those that arise during in vitro library preparation could also be covered by various embodiments of the invention.

Process 200 classifies and prioritizes (209) candidate chimeras using statistical scores. Various methodologies exist to classify and prioritize candidate chimeras. In many embodiments, candidate chimeras are classified based on their ability to align to various indices/databases. For example, reads that align to an indel index, resulting in an alignment score, can be classified based on priority rules. These alignments can determine whether a read is consistent or inconsistent with the chimeric junction to which it aligns. An inconsistent read is considered to be an anomaly.

Once classified, candidate chimeras can be prioritized using statistical scores that suggest their likelihood of being bona-fide chimeras or false positives. Prioritization, as described in many embodiments, does not necessarily rely on censoring approaches. Censoring, which is a common methodology in the field, can immediately exclude sequencing reads based on hard thresholds (e.g., alignment quality, nucleotide overhang). By contrast, processes in accordance with many embodiments of the invention rely on these typically excluded reads to create statistical probabilities. For example, these reads can be used to estimate the probability that each candidate fusion is an artifact. In several embodiments, the reads with poor alignment scores, mapping to constructed indel indices, and/or where mates map inconsistently (anomalies) are used to generate generalized linear models (GLM). The candidate chimeras can be fit on these GLMs to estimate the probability that the read's alignment was artifactual.

In a number of embodiments, the probabilities generated by the GLM for each read are aggregated to generate a cumulative score for each candidate. These cumulative scores can be compared to a null distribution, which can be constructed by an appropriate therefrom or model (e.g., Hoeffding combinatorial central limit therefrom). In many embodiments, a score values the likelihood of a true junction. It should be understood, however, that many methodologies exist to determine the likelihood of a true junction, such as, for example, cumulative distributive functions or aggregate predictive values.

Because some candidate chimeric sequences are likely linear canonical splicing events, process 200 declassifies (211) these sequences as putative chimeras. In several embodiments, bioinformatics prediction is used to identify candidate chimeras that are likely to be artifactual because these candidates are homologous to canonical splicing events. By mapping candidate chimeras to genome or other indices that have annotated splice junctions, candidates that are mappable can be removed. In addition, candidates can be removed if they map to unannotated splice junctions, but are likely bona-fide cryptic splicing events, as identified by key signals (e.g., canonical splice acceptor/donor sequence or genetic distance between exons). Removal of candidates based on canonical splicing events can be adjusted or even removed by the user, dependent on whether a conservative or liberal candidate chimera database is desired.

To reveal bona-fide chimeric sequences, process 200 assigns (213) an empirical p value to each candidate chimera. Embodiments are directed to using a statistical framework to generate an empirical p value for each candidate chimera, wherein the framework estimates the probability the candidate is an artifact based on an empirical null. This value is different from the junction score described above because it uses a more realistic null model, accounting for structure in the null distribution. To calculate an empirical p value, data that would be discarded by many other methodologies is used to model the null distribution. An empirical p value can be used to determine which fusions are reported and to prioritize candidates for follow-up study. Additionally, standard statistical analysis of p values can be applied to estimate a false discovery rate and can assist in determining the PPV, FP rates. In a number of embodiments, an empirical p value is utilized to prioritize a candidate chimera for further investigation.

Process 200 also outputs (215) a report listing a plurality of candidate chimeras with their respective assigned empirical p values. As is discussed further below, candidate chimeras can be used for experimental analyses and conclusions, diagnostics, and/or further experimentation.

While specific examples of processes for unveiling and signifying biomolecule chimeras are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for unveiling and signifying biomolecule chimeras appropriate to the requirements of a given application can be utilized in accordance with various embodiments of the invention.

It should be further noted that various embodiments of the invention improve upon previously described and customarily utilized methods. For example, the methods describing chimeric sequence unveiling enable identification of the following events not detected by other customarily utilized methods: (a) splicing between annotated exons on the same chromosome separated by more than a user-defined radius, most likely arising from tandem duplications or large deletions; (b) inversions, which are defined as transcripts containing annotated exons separated by the same user-defined radius or more on the same chromosome in discrepant transcriptional orientations; and (c) translocations, which are defined as transcripts containing annotated exons from two genes on different chromosomes in the reference genome. Throughout the present disclosure, hg19 and the UCSC GRCh37 gene annotations are used for reference, but it should be understood that the choice of genome build, annotation, and the user-defined radius for detecting events (a) or (b) are choices which can easily be modified by the user. While the following embodiments detail the discovery of chimeras using RNA sequence at exonic boundaries, many embodiments of the invention are also directed to unveiling chimeric sequences at un-annotated boundaries and for DNA sequences.

Figure 3:
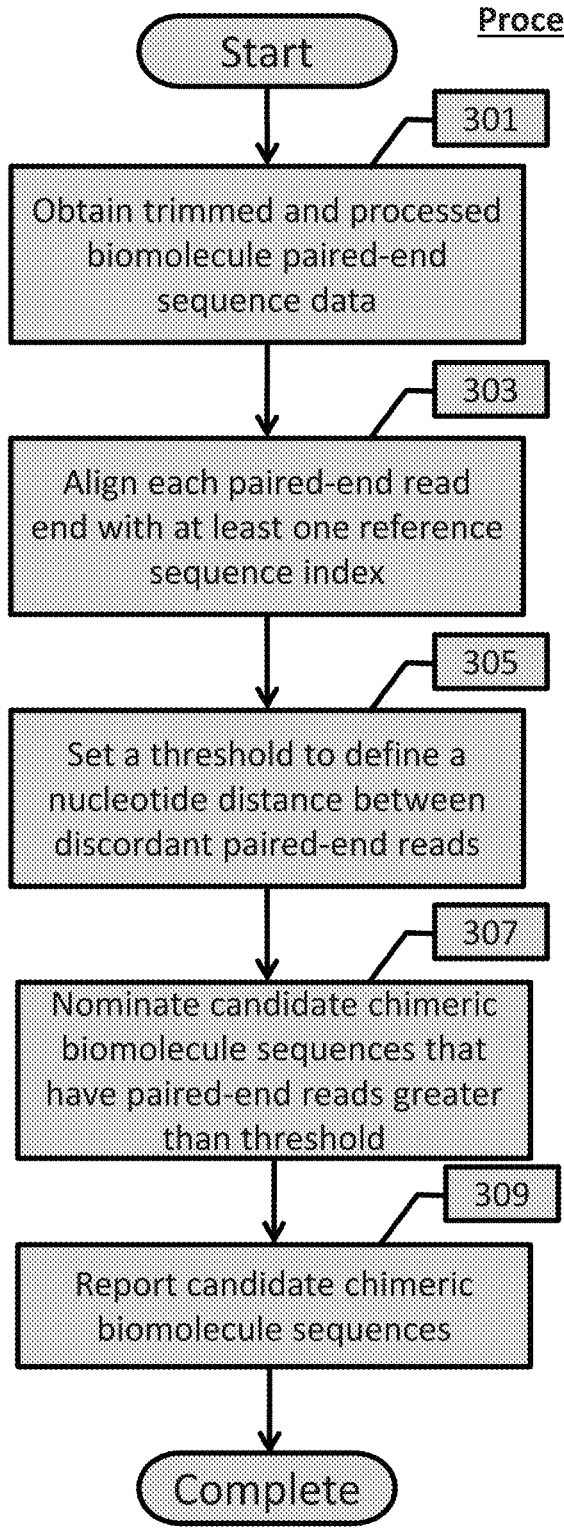
FIG. 3 illustrates a process for classifying paired sequence reads from paired-end sequence data as discordant in accordance with an embodiment of the invention.

Depicted in FIG. 3 is an embodiment of a process to nominate candidate chimeric biomolecule sequences from paired-end sequence data. Process 300 obtains (301) trimmed and processed biomolecule paired-end sequence data. The source of biomolecule sequence data can be derived de novo (i.e., from a biological source), from a public or private database, or generated in silico. Several methods are well known to derive biomolecule sequence data from biological sources. Generally, biomolecules are extracted from tissue, prepped to be sequenced, and then run on a sequencer to obtain paired-end sequencing data. For example, RNA can be extracted from a human tissue source such as a biopsy, then prepped into a sequence library using standard techniques, and sequenced on a next-generation sequencing platform, such as those manufactured by Illumina. Likewise, biomolecule sequence data can be derived from an available database having paired-end sequence data. For example, transcriptome data can be obtained from the National Center for Biotechnology Information (NCBI) Reference Sequence (RefSeq) or TCGA databases. In addition, sequences to be analyzed can be generated in silico, by any appropriate computational methods. The sequence data should be trimmed and processed to remove bad quality reads and any other reads having undesirable qualities.

Each paired-end read is aligned (303) with at least one reference sequence index. Any appropriate reference sequence index can be utilized, often depending on the application. Typical reference sequence indices include a genomic index and a linear exon-exon junction index. It should be understood that any index can be used in combination with another index and fall with in various embodiments of the invention.

A threshold is set (305) to define a nucleotide distance between discordant paired-end reads that would signify a putative chimeric biomolecule sequence. Discordant spanning reads arise when one end of the read maps to a first locus in the genome and the other end maps to a second distant locus in the genome. The distance in which the discordant read become a candidate chimeric molecule can be dependent on the definition provided by a user. In theory, a chimeric molecule could arise from a small deletion (e.g. 25 kb), especially in gene rich areas of the genome. On the other hand, some genes in the human genome have extremely large introns, with some exceeding 50 kb. Thus, an appropriate threshold can be dependent on the balance of excluding possible chimeras due or nominating some candidate chimeras that are linear canonical splicing events. Accordingly, the appropriate distance varies, and could be, for example, 25, 50, 100, or 200 kb. As can readily be appreciated, the specific distance used in a specific context is largely dependent upon the requirements of a given application. Based on this threshold, candidate chimeric biomolecules are nominated (307) when the paired-end reads are more distant than the threshold.

Process 300 also outputs (309) a report listing a plurality of candidate chimeric biomolecule sequences. As is discussed further below, candidate chimeric biomolecule sequences can be used for computational, statistical, and/or experimental analyses.

While specific examples of processes for nominating candidate chimeric biomolecule sequences from paired-end sequence data are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for nominating candidate chimeric biomolecule sequences from paired-end sequence data appropriate to the requirements of a given application can be utilized in accordance with various embodiments of the invention.

Figure 4:
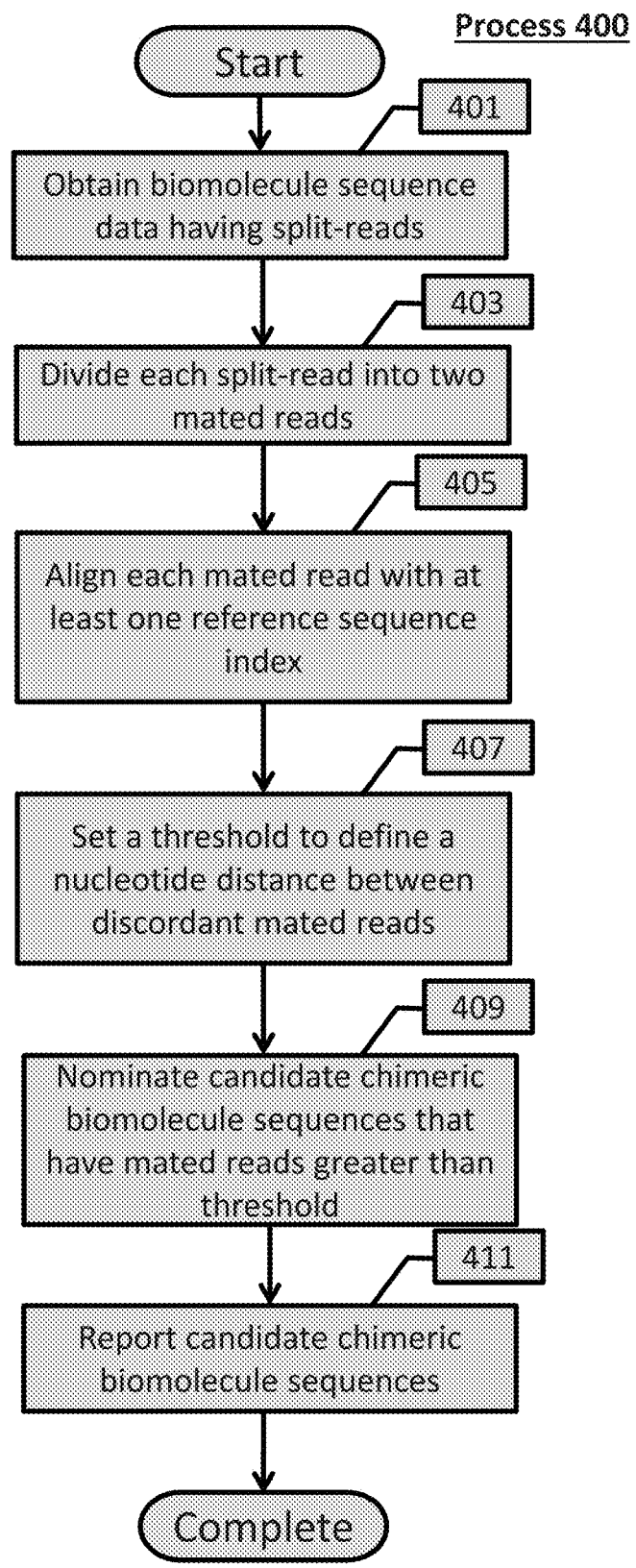
FIG. 4 illustrates a process for classifying paired sequence reads from split-read sequence data as discordant in accordance with an embodiment of the invention.

Depicted in FIG. 4 is an embodiment of a process to nominate candidate chimeric biomolecule sequence data having split-reads. Split reads are reads in which one end of the read maps to one locus in the genome and the opposite end of the read maps to a distant locus. The precise definition of a read can vary and nomination of split reads as chimeric sequences can be dependent on predetermined requirements and/or user definitions. For example, the definition of a qualified alignment to the genome can vary and may be dependent on the read length. Ideally, the read would be long enough to confidently assign both ends of the read to two separate loci. The greater the length of the read alignment to the genome, the more likely the read is accurate. Accordingly, embodiments are directed to methods that utilize reads of appropriate length. In some of these embodiments, the read is at least 50 bases, with each fragment alignment having at least 25 bases. In several embodiments, the read is at least 70 bases, with fragments of at least 35 bases; or at least 100 bases, with fragments of at least 50 bases. In addition, the fragments in the split read can be of different sizes (e.g., 100 base read, and 30 and 70 base fragments). In more embodiments, identification of spice sites can help nominate and filter potential chimeric sequences.

Process 400 obtains (401) trimmed and processed biomolecule sequence data having split-reads. The source of biomolecule sequence data can be derived de novo (i.e., from a biological source), from a public or private database, or generated in silico. Several methods are well known to derive biomolecule sequence data from biological sources. Generally, biomolecules are extracted from tissue, prepped to be sequenced, and then run on a sequencer to obtain paired-end sequencing data. For example, RNA can be extracted from a human tissue source such as a biopsy, then prepped into a sequence library using standard techniques, and sequenced on a next-generation sequencing platform, such as those manufactured by Illumina. Likewise, biomolecule sequence data can be derived from an available database having paired-end sequence data. For example, transcriptome data can be obtained from the National Center for Biotechnology Information (NCBI) Reference Sequence (RefSeq) or TCGA databases. In addition, sequences to be analyzed can be generated in silico, by any appropriate computational methods. The sequence data should be trimmed and processed to remove bad quality reads and any other reads having undesirable qualities.

Each split-read is divided (403) into two mated (i.e., paired) reads, where the division occurs at the location within the read that yields a 5' read and 3' read that each align to a discordant location of a reference sequence. Accordingly, each paired read is aligned (405) with at least one reference sequence index. Any appropriate reference sequence index can be utilized, often depending on the application. Typical reference sequence indices include a genomic index and a linear exon-exon junction index. It should be understood that any index can be used in combination with another index and fall within various embodiments of the invention.

A threshold can be set (407) to define a nucleotide distance between discordant split-reads that would signify a putative chimeric biomolecule sequence. Discordant spanning reads arise when one paired read maps to a first locus in the genome and the other paired read maps to a second distant locus in the genome. The distance in which the discordant reads become a candidate chimeric molecule can be dependent on the definition provided by a user. In theory, a chimeric molecule could arise from a small deletion (e.g. 25 kb), especially in gene rich areas of the genome. On the other hand, some genes in the human genome have extremely large introns, with some exceeding 50 kb. Thus, an appropriate threshold can be dependent on the balance of excluding possible chimeras due or nominating some candidate chimeras that are linear canonical splicing events. Accordingly, the appropriate distance varies, and could be, for example, 25, 50, 100, or 200 kb. As can readily be appreciated, the specific distance used in a specific context is largely dependent upon the requirements of a given application. Based on this threshold, candidate chimeric biomolecules are nominated (409) when the paired split-reads are more distant than the threshold.

Process 400 also outputs (411) a report listing a plurality of candidate chimeric biomolecule sequences. As is discussed further below, candidate chimeric biomolecule sequences can be used for further computational, statistical, and/or experimental analyses.

While specific examples of processes for nominating candidate chimeric biomolecule sequences from split-read sequence data are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for nominating candidate chimeric biomolecule sequences from split-read sequence data appropriate to the requirements of a given application can be utilized in accordance with various embodiments of the invention.

Figure 5:
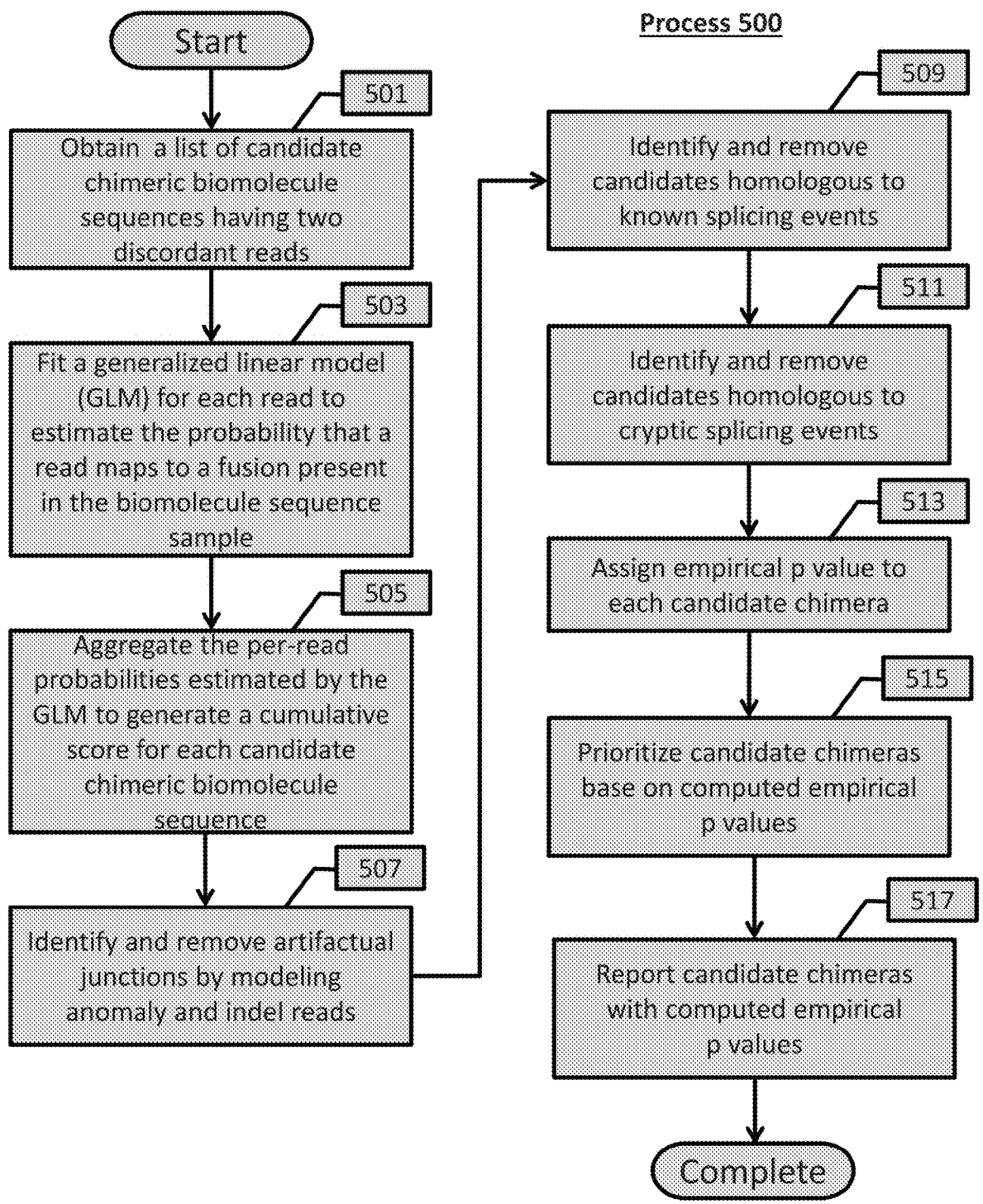
FIG. 5 illustrates a process for unveiling chimeric biomolecule sequences in accordance with an embodiment of the invention.

Depicted in FIG. 5 is an embodiment of a process to statistically prioritize candidate chimeras. Process 500 obtains (501) a list of candidate chimeric biomolecule sequences that have two discordant reads. The biomolecule sequences can be derived and processed by various methods as described herein or known in the art. Accordingly, biomolecule sequences can be derived de novo (i.e., from a biological source), from a public or private database, or generated in silico and sequenced in an appropriate manner. Paired-end reads or split-reads can be utilized in accordance with a number of embodiments. The biomolecule sequence reads should be processed and aligned to a reference sequence index to ensure the reads are discordant. In many instances, the discordant reads have a genetic distance greater than a defined threshold.

A generalized linear model (GLM) can be fit (503) for each read to estimate the probability that a read maps to a fusion present in the sample from which the biomolecule sequence was derived. In many embodiments, a generalized linear model will utilize predictors of alignment scores (e.g., bowtie2), mapping quality, and the amount of junction overlap (i.e., length reads 5' and 3' of junction). In several embodiments, a GLM is used to estimate the probability that a read's alignment to a putative fusion was due to an artifact. In various embodiments, a GLM discriminates between 'consistent', 'inconsistent' and 'artifactual' reads. Consistent reads are those for which one read is aligned across a fusion junction and the second paired read is at an appropriate linear distance. Inconsistent reads are those for which one read is aligned across a fusion junction and the second paired read is incompatible (i.e., an inappropriate distance from the junction). Artifactual reads are those for which one end aligns across an exon an insertion or deletion, suggesting that the junction was created as an artifact of library preparation. In particular embodiments, a GLM uses predictors from both reads, using the following command:

x=glm(is.pos~overlap+lenAdjScore+qual+len-
AdjScoreR2+qualR2, data=readPredictions,
family=binomial(link="logit"),
weights=readPredictions[,cur_weight])

where is.pos is 1 for "consistent" reads and 0 for "inconsistent" reads, overlap is a minimum number of nucleotides that flank each side of the junction breakpoint, qualR2 are mapping qualities, and lenAdjScoreR2 is an adjusted alignment score.

Probabilities for each read of each candidate chimeric biomolecule sequence are aggregated (505) to generate a cumulative score for each candidate. In many instances, a cumulative score is generated by comparing each estimated probability to a null junction score distribution. In some embodiments, a null junction score distribution is constructed for each value of N, the number of reads aligning to the fusion junction, by randomly sampling from the empirical distribution of a probability that a read is an artifact for all reads in the sequencing library when N is small. In other embodiments, a null distribution is constructed for each value of N, the number of reads aligning to the fusion junction using the Hoeffding combinatorial central limit theorem to estimate a distribution for large N (Hoeffding, *Ann Math Stat,* 22:558-66, 1951, the disclosure of which is incorporated herein by reference in its entirety). Comparing the cumulative score for each junction to the null distribution results in assignment of a junction value to each fusion junction, in accordance with numerous embodiments.

Artifactual junctions can be identified and removed (507) by modeling anomaly and indel reads with a GLM. In some instances, each read aligning to a fusion indel sequence can be assigned a probability that it is an artifact by a GLM. In many instances, anomaly reads are stratified according to whether they align to linear junctions classified as "good" or "bad" and are used to fit an anomaly GLM model. An anomaly GLM model can be used to assign each read a probability that it is an anomaly.

Candidate chimeric biomolecule sequences homologous to canonical splicing events can be identified and removed (509). Candidates can be mapped to a reference genome and junction indices. Sequences similar to the reference genome can be removed, removing false positive chimeras. Likewise, candidate chimeric biomolecule sequences homologous to cryptic splicing events are identified and removed (509). In many instances, candidates are removed if, when split, the 5' and 3' ends of paired reads map to the genome within a defined genetic distance (e.g., 10 kb, 25 kb, 50 kb, 100 kb).

An empirical p value is assigned (513) to each candidate chimeric biomolecule sequence such that the p value signifies the likelihood that the candidate is a bona fide chimeric sequence. In several embodiments, the determination of a p value utilizes data that would be discarded in other processes, such as data of mappable candidates. In some embodiments, an empirical p value for each fusion junction is estimated by referring its junction score to an empirical distribution of junction scores of mappable fusion junctions. In a number of embodiments, further statistical analysis can utilize empirical p values to estimate a false discovery rate. Empirical p values of each candidate can be used to prioritize (515) the candidates.

Process 500 can also output (517) a report listing a plurality of candidate chimeric biomolecule sequences and their computed empirical p values. As is discussed further below, candidate chimeric biomolecule sequences can be used for further research, medicinal development, and/or medical diagnostics.

While specific examples of processes for statistically prioritizing candidate chimeras are described above, one of ordinary skill in the art can appreciate that various steps of these processes can be performed in different orders and that certain steps may be optional according to some embodiments of the invention. As such, it should be clear that the various steps of the processes could be used as appropriate to the requirements of specific applications. Furthermore, any of a variety of processes for statistically prioritizing candidate chimeras appropriate to the requirements of a given application can be utilized in accordance with various embodiments of the invention.

Unveiling of Chimeras from Large Databases

Big datasets, such as The Cancer Genome Atlas (TCGA), are excellent resources of transcriptome and expression data to analyze. Large datasets are extremely difficult to parse through due to the enormous amount of data stored within it. Accordingly, processes to unveil chimeric sequences can benefit from a method that can improve performance and reduce the time required for analysis.

Running processes to discover chimeras in massive sequence datasets can present computational challenges. First, chimeric sequence unveiling processes using RNA-seq for detection are typically designed to be run on single samples in isolation, rather than 'borrowing strength' across samples, a standard statistical principle known to increase power. Thus, various unveiling processes produce results that do not control for multiple hypotheses testing of any specific chimera being an artifact across n samples. Standard false discovery rate control can of course be applied, but false discovery methods do not control for the fact that specific chimeras may be multiply tested by a process anywhere from 1 to n times. Secondly, running conventional chimera unveiling processes on hundreds or thousands of samples can be costly and time consuming, requiring tens of dollars per sample using cloud computing resources.

Figure 6A:
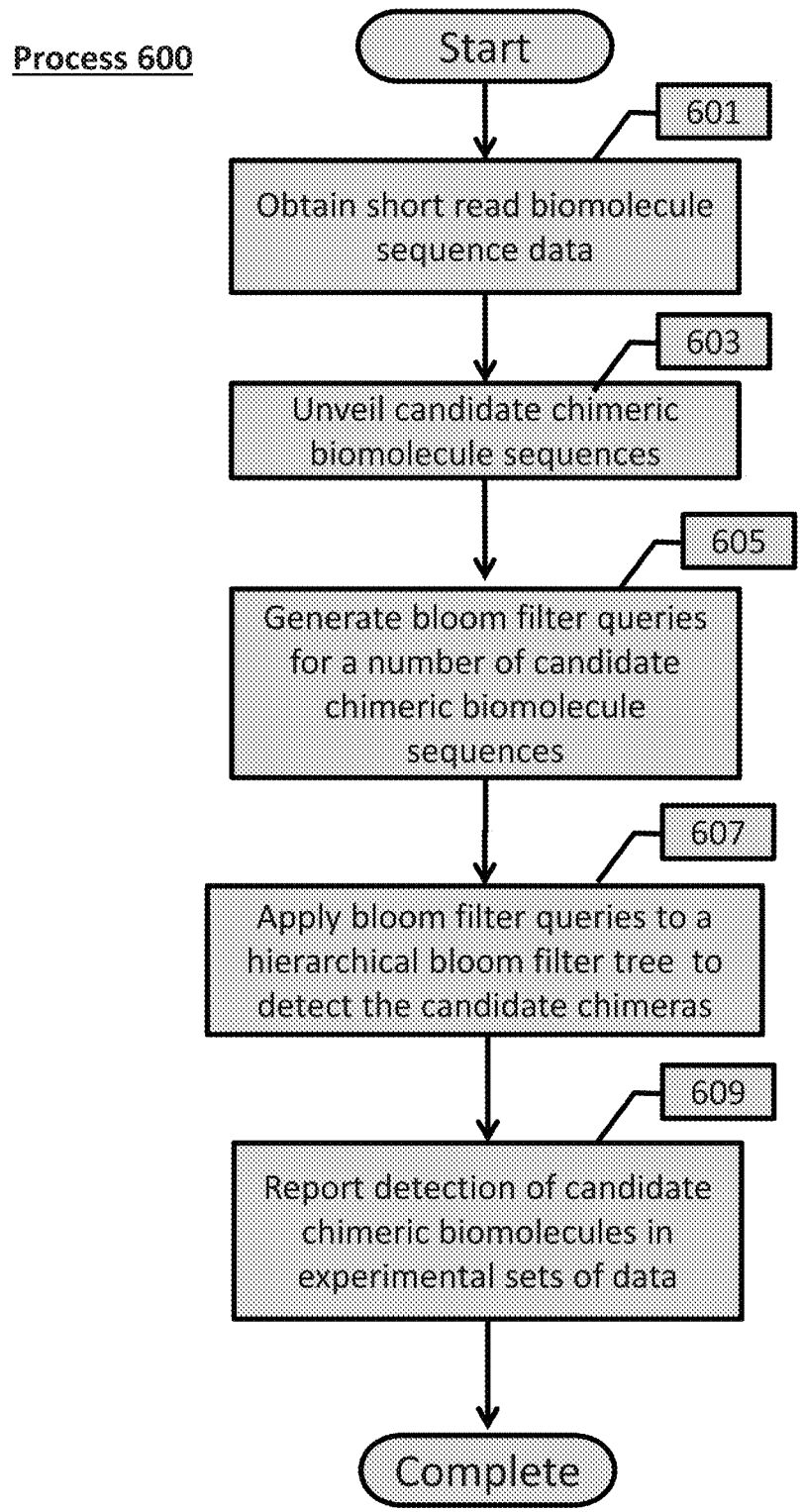
FIG. 6A illustrates a process for analyzing candidate chimeric biomolecule sequences in accordance with an embodiment of the invention.

As depicted in FIG. 6A, process 600 includes, in accordance with an embodiment, a two-component approach that takes a set of samples and applies a chimeric unveiling process and bloom filter query of sequence reads, which allows querying of thousands of samples quickly and cheaply. The impressive efficiency of bloom filters combined with processes for the empirical statistical evaluation of putative chimeric sequences (e.g., process 200) yields a process that greatly out performs chimera unveiling processes utilizing traditional methods.

To illustrate the potential benefit in efficiency, it typically takes about $25 and 15 to 20 hours to run a non-bloom filtered chimeric unveiling process for one sample gene. Processes that utilize bloom filters, on the other hand, have queries that cost only a few dollars and can be completed rapidly, in three hours for even the largest bloom filters (e.g., bloom filters for the gene BRCA). Queries for an average bloom filter can be completed in less than an hour using machines with 30 GB of RAM. It should be noted, however, it typically requires a one-time cost and time investment of 100 to 200 dollars and 10 to 24 hours to construct a hierarchal bloom filter tree data structure (depending on the number of files), but after this build, queries are cheap and efficient. Any appropriate data storage and computing machine can be used. For example, the exemplary embodiments section below describes the use of processes that were performed on the Seven Bridges Cancer Genomics Cloud (CGC). With proper statistical control, bloom filters can significantly enhance the efficiency and statistical precision of chimera detection. It should be further noted, however, that other filters such as grep can be used instead of bloom filters, but the use of the filters may not be as efficient.

Scalable process 600 can incorporate the use of a chimeric unveiling process, such as (but not limited to) process 200 described above with respect to FIG. 2. Accordingly, process 200 can be performed with biomolecule sequence reads derived from multiple samples from any appropriate database using any appropriate data storage platform. For example, samples can be retrieved from the TCGA database using the CGC platform, but the samples can be generally retrieved from any appropriate database using any appropriate platform. It should be noted that either discordant spanning reads or split reads can be used, but caution is often undertaken when using the split-read mode of process 200 because read lengths in a database may be varied by sample, with many datasets having inadequate read lengths for the split-read mode. An advantage of the use of the CGC platform is that it can allow other users to access both the workflows, data, and computational resources often required to run chimeric unveiling processes. In addition, docker containers with the tools are available and the workflows are described using Common Workflow Language (CWL). This allows other users to run the workflows in other computation environments with minor adjustments (e.g., altering some AWS-specific settings) using a CWL executor and can be extended to arbitrary datasets.

As shown in FIG. 6, process 600 detects candidate chimeric sequences in experimental sequencing sets of data. In many embodiments, process 600 is to be employed on large datasets. It should be noted, however, that although process 600 is designed for large datasets, it could be used on any size dataset, including datasets of a modest size. An advantage of process 600 is not only the ability to process large data sets, but also time efficiency, and thus evaluation of smaller datasets could also benefit from applying bloom filters as those described in process 600.

Process 600 obtains (601) biomolecule sequence data. In several embodiments, sequence data is transcriptome data derived from sequencing RNA in a next-generation sequencing platform, such as those manufactured by Illumina. It should be understood, however, that the sequence data could be derived from DNA or proteins, such as from a genome or proteome. The source of biomolecule sequence data can be derived de novo (i.e., from a biological source), from a public or private database, or generated in silico. Several methods are well known to derive biomolecule sequence data from these sources, and are described generally in various sections herein. Furthermore, it would be understood that any appropriate processing of the biomolecule sequence can be performed as understood in the art, such as trimming various sequences to remove inadequate sequence reads.

Process 600 unveils (603) chimeric genes from the sequence reads. Many processes exist for unveiling of chimeric biomolecule sequences, including various processes and embodiments described herein. The specific method chosen to unveil chimeras is typically dependent upon the requirements of a given application, and any appropriate method can be used in accordance with various embodiments.

Bloom filter queries are generated (605) for a number of candidate chimeric biomolecule sequences in process 600 for the purpose of parsing and pruning sequence reads from the sequence data. In many embodiments, a bloom filter query is a sequence containing candidate chimeric biomolecule sequences. In a number embodiments, a bloom filter query is a transcript. In several embodiments, a bloom filter query is derived, at least in part, from a process for unveiling candidate chimeric biomolecules. In a number of embodiments, a query is selected based on various criteria, including (but not limited to) mapping quality, sequence length, sequence composition, chimeric potential (e.g., distance between sequence reads), and anomalies present. It should be understood that a number a ways to generate bloom queries can be performed within various embodiments of the invention.

To efficiently analyze candidate chimeric sequences, the constructed bloom filter queries are applied (607) to a hierarchical bloom filter tree data structure to detect candidate chimeric sequences within an experimental data set. In numerous of embodiments, candidate chimeric sequences can be validated via hierarchical bloom filter tree data analysis. In many embodiments, the use of hierarchical bloom filter trees can reveal that candidate chimeric sequences exist in other sequencing experiments, further legitimizing their bona fide existence. Furthermore, the use of hierarchical bloom filter trees can also reveal that candidate chimeric sequences exist in other conditions, such as another disorder. For example, if the bloom filter queries are generated from a first neoplasm (e.g., breast cancer), candidate chimeras of the first neoplasm can be found in a hierarchical bloom filter tree constructed (at least in part) from a second neoplasm (e.g., ovarian cancer), promoting an understanding that the candidate chimera is very likely to be involved in both neoplasms. Likewise, the use of multiple hierarchical bloom filter trees constructed using different neoplasms can reveal candidate chimeric sequences common to a number of cancers.

In a number of embodiments, a hierarchical bloom filter tree is an indexing data structure to facilitate searching of short sequence reads having candidate chimeras. A hierarchical bloom filter tree includes a hierarchy of compressed bloom filters, each having a set of "k-mers" (i.e., short sequence reads have a length of k), established as indexing node. Each compressed bloom filter has a single filter which stores a set of universally unique identifiers. A query begins at a "root" node and extends downward through intermediate nodes until reaches a "leaf" bloom filter, in which a match between the query sequence and the bloom filter can be assessed. In many embodiments, a leaf bloom filter is an experimental set of sequencing data. In several embodiments, each bloom filter of an intermediate and root node (i.e., not a leaf) is a parent node having two children nodes. The k-mers of child's bloom filter is included within the parent's bloom filter. Accordingly, each parent's bloom filter includes a set k-mers that incorporates the subset of k-mers of each of its children.

In many embodiments, a biomolecule sequence query is first applied to the applied to a root bloom filter. If there is a positive match between kmers of a biomolecule sequence query and kmers of a parent, then the biomolecule sequence query is next applied to the two children of the parent. If there is a no match between kmers of a biomolecule sequence query and kmers of a parent, the tree is pruned at that node, such that the children bloom filters and the progeny are not queried. Pruning results in an efficient querry, as many nodes and their associated bloom filters will not be queried, saving computation time. The application of a biomolecule sequence query to parental nodes continues until it reaches a leaf or until all leaves are pruned. If there is a positive match between kmers of a biomolecule sequence query and kmers of a leaf, then the candidate chimeric biomolecule sequence associated with the sequence query is present in the experimental set of sequencing data associated with the leaf. Alternatively, if all leaves are pruned, the candidate chimeric biomolecule sequence associated with the sequence query is not present in any of the experimental sets of sequencing data.

Bloom filters to be constructed are dependent on the process objective and the efficiency desired. More filters with higher stringency will prune more sequence reads, which can increase the efficiency of the process. Increased efficiency, however, can come at the cost of pruning potentially desirable sequence reads. Thus, a determination is often made to obtain a balance of efficiency and depth appropriate to the requirements of a specific application. Non-exhaustive examples of bloom filter queries include filtering based on mapping quality, genetic distance definitions, and categorical filters. Once bloom filters are constructed, they can be used multiple times for multiple experiments and runs.

In numerous embodiments, a hierarchical bloom filter is built around a collection of bloom filters. Bloom filters are an efficient way to store a set of items from a universe U. Each filter consists of a bit vector of length m and a set of h hash functions $h_i$: U→[0, m) that map items to bits in the bit vector. Insertion of u∈U is performed by setting to 1 the bits specified by $h_i(u)$ for i=1, . . . , h. Querying for membership of u checks these same bits; if they are all 1, the filter is reported to contain u. Because of overlapping hash results, bloom filters have a one-sided error: they may report an item is present when it is not, however, this error can be adjusted with modification of m and h.

In several embodiments, a hierarchical bloom filter tree data structure is composed of binary bloom filters, many associated with a node, and in which the sequencing experiments are associated with leaves. Each node v of the tree contains a bloom filter that contains the set of k-mers present in any read in any experiment in the subtree rooted at v. A filter at any node v is the union of the filters of its children. A union of bloom filters b1 and b2 can be efficiently computed by simply taking the bitwise-OR of b1 and b2, resulting in more bits set to 1 in the nodes most towards the root.

Application of the bloom filters can increase the efficiency of a chimeric unveiling process. In this way, large datasets can be queried and analyzed. Furthermore, experiments can be run on multiple datasets, which then can be cross-analyzed. This allows for multiple hypotheses to be tested and correlations between and across different datasets to be analyzed. For example, correlations of chimeric genes between different cancer types can be ascertained using this method. As such, rare chimeric genes may be found that exist in multiple cancer types, despite a low prevalence in any single type of cancer.

Reports of detected candidate chimeric biomolecules in experimental sequencing sets of data can be created, stored, and/or presented (609). As is discussed further below, detected candidate chimeras can be used for experimental analyses and conclusions, diagnostics, and/or further experimentation.

While specific examples of processes for efficiently detecting candidate chimeric sequences in experimental sequencing sets of data are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for efficiently detecting biomolecule chimeras appropriate to the requirements of a given application can be utilized in accordance with various embodiments of the invention.

Construction of a Hierarchical Bloom Filter Tree Data Structure

A hierarchical bloom filter tree data structure can be built for a query in accordance with a number of embodiments. Depicted in FIG. 6B is a process to build and store a hierarchical bloom filter tree structure in accordance with an embodiment. As shown, process 620 obtains (621) a plurality of biomolecule sequence data sets. In several embodiments, sequence data is transcriptome data derived from sequencing RNA in a next-generation sequencing platform, such as those manufactured by Illumina, Inc., of San Diego, Calif. It should be understood, however, that the sequence data could be derived from DNA or proteins, such as from a genome or proteome. The source of biomolecule sequence data can be derived de novo (i.e., from a biological source), from a public or private database, or generated in silico. Several methods are well known to derive biomolecule sequence data from these sources, and are described generally in various sections herein. In many embodiments, several data sets are obtained, which may increase statistical power to accurately unveil chimeric molecules.

In a number of embodiments, a data set is a collection of sequencing data corresponding to a particular experiment. In many embodiments, a data set is a collection of sequencing data corresponding to a particular disorder or disease state, such as a sequencing data derived from a cohort of patients having the particular disorder or disease states. In several embodiments, a data set is a collection of sequencing data corresponding to a particular neoplasm, such as the various data sets available in the TCGA. It should be understood that the precise definition of a data set can vary depending on the application, and thus a multitude of embodiments can utilize numerous variations of various data sets.

Process 620 assigns (623) biomolecule sequences from data sets that have been broken into subsets k-mers to a plurality of leaf bloom filters. In many embodiments, bloom filters are assigned FASTA sequences. For example, sequences can be constructed using the Jellyfish k-mer counting library (Marçais and Kingsford Bioinformatics, 27(6):764-770, 2011, the disclosure of which is herein incorporated by reference) from short-read FASTA files by counting canonical k-mers (the lexicographically smaller k-mer between a k-mer and its reverse complement). An appropriate nucleotide length of k-mer is chosen (e.g., k=17, 18, 19, 20, 21, 22, 23, 24, 25, etc.).

To avoid counting k-mers that result from sequencing errors and to attempt to select k-mers from genes with reasonable coverage, in accordance with numerous embodiments, trees are built containing k-mers that occur greater than a file-dependent threshold. In many embodiments, a threshold count(si) is determined using a file size of experiment si as follows: count(si)=1 if si is 300 MB or less, count(si)=3 for files of size 300-500 MB, count(si)=10 for files of size 500 MB-1 GB, count(si)=20 for files between 1 GB and 3 GB, and count(si)=50 for files>3 GB or larger FASTA files.

Two important parameters should be set when constructing the bloom filters contained in a hierarchal tree data structure, including the bloom filter length (m) and the number of hash functions (h) used in the filter. The k-mer threshold θu should also be set for each node. In many embodiments, a uniform threshold θ=θu is used for all nodes u.

Process 620 constructs and layers (625) bloom filters into a hierarchal tree data structure. In many embodiments, a hierarchical bloom filter tree is an indexing data structure to facilitate searching of short sequence reads having candidate chimeras. A hierarchical bloom filter tree includes a hierarchy of compressed bloom filters, each having a set of "k-mers" (i.e., short sequence reads have a length of k), established as indexing node. Each compressed bloom filter has a single filter which stores a set of universally unique identifiers. Accordingly, several embodiments of a hierarchical bloom filter tree have a plurality of leaf bloom filters, each incorporating k-mers of an experimental data set. Each leaf has a binary parental intermediate node having a bloom filter incorporating the k-mers of its two downstream children. Each intermediate node has its own binary parental intermediate node having a bloom filter incorporating the k-mers of its two children. At the apex of a hierarchical bloom filter tree is a binary parental root node, having a bloom filter incorporating the entire collection of k-mers (i.e., all experimental sequencing data sets).

In some embodiments, a hierarchical bloom filter tree data structure is built by repeated insertion of sequencing experiments. In many embodiments, a sequencing experiment refers to a sequencing data set saved in a database. In several embodiments, a sequencing experiment refers to results of one prepared library. In numerous embodiments, a sequencing experiment refers to a full or partial set of sequencing data derived from a particular biological sample, such as a patient biopsy or research specimen. It should be understood, however, that any set of sequencing data can be used as an experiment and often depends on the purpose of the hierarchical bloom filter tree data structure to be built.

Given a (possibly empty) hierarchical bloom filter tree data structure T, a new sequencing experiment s can be inserted into T by first computing the bloom filter b(s) of the k-mers present in s and then walking from a root along a path to the leaves and inserting s near the bottom of T. When at node u, if u has a single child, a node representing s (and containing b(s)) is inserted as u's second child. If u has two children, b(s) is compared against the bloom filters b(left(u)) and b(right(u)) of the left left(u) and right right(u) children of u. The child with the more similar filter under the Hamming distance between the filters becomes the current node, and the process is repeated. If u has no children, u represents a sequencing experiment st. In this case, a new union node v is created as a child of u's parent. This new node has two children: u and a new node representing s.

As s is walked down a tree, filters at the nodes that are visited are unioned with b(s). This unioning process can be made fast (and trivially parallelized for large filters) since the union of two bloom filters can be computed by ORing together the bit vectors. This is particularly beneficial where GPU or vector computations can be used for these SIMD operations.

After a hierarchal bloom filter tree structure is built, in accordance with various embodiments, the filters (both leaf and internal) are compressed using a vector compression technique. For example, the RRR bit vector compression scheme (Raman, Raman, and Rao *ACM Trans. Algorithms* 3, 4, Article 43 (2007), (DOI=10.1145/1290672.1290680)) can be utilized.

A hierarchical bloom filter tree data structure stored (627) in an appropriate memory. As is discussed herein, hierarchical bloom filter trees can be used to further detect and analyze candidate chimeric biomolecule sequences.

While specific examples of processes for constructing a hierarchical bloom filter tree data structure are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for constructing a hierarchical bloom filter tree data structure appropriate to the requirements of a given application can be utilized in accordance with various embodiments of the invention.

Querying a Hierarchical Bloom Filter Tree Data Structure

Figure 6C:
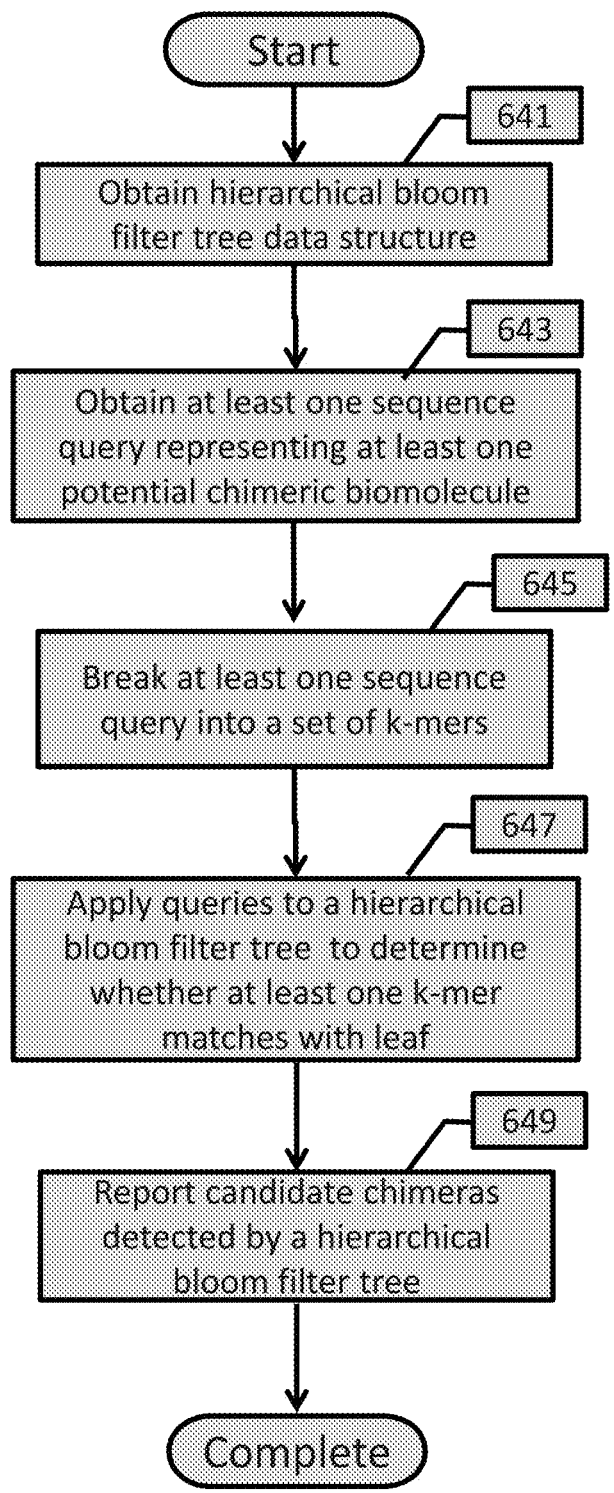
FIG. 6C illustrates a process for querying a hierarchical tree data structure in accordance with an embodiment of the invention.

A hierarchical bloom filter tree data structure can be queried to find chimeric biomolecule sequences in accordance with a number of embodiments. Depicted in FIG. 6C is a process to detect candidate chimeric sequences using a hierarchical bloom filter tree data structure. Process 640 obtains (641) a hierarchical bloom filter tree data structure. A hierarchical bloom filter tree data structure can be constructed, as described herein or by any other appropriate method, or obtained from another source. An appropriate hierarchical bloom filter tree data structure depends on the analysis to be performed. For example, to detect chimeric biomolecule sequences in a particular neoplasm (e.g., breast cancer), a hierarchical bloom filter tree data structure should be constructed using sequencing experiments (including stored database results) performed on the neoplasm. It should be understood that any appropriate constructed hierarchical bloom filter tree data structure can be used to find chimeric biomolecule sequences in accordance with a number of embodiments. Furthermore, a hierarchical bloom filter tree data structure can be constructed from multiple experiments over multiple conditions. For example, a pan-cancer hierarchical bloom filter tree data structure can be constructed using multiple experiments performed on multiple cancers.

Process 640 also obtains (643) at least one sequence query representing at least one potential chimeric biomolecule sequence. In many embodiments, a bloom filter query is a sequence containing multiple candidate chimeric biomolecule sequences. In several embodiments, a bloom filter query is derived, at least in part, from a process for unveiling candidate chimeric biomolecules. In a number of embodiments, a query is selected based on various criteria, including (but not limited to) mapping quality, sequence length, sequence composition, chimeric potential (e.g., distance between sequence reads), and anomalies present. In several embodiments, a collection of sequence queries are obtained to be analyzed as a batch. It should be understood that obtained sequence queries can be generated a number of ways within various embodiments of the invention.

Process 640 breaks (645) at least one sequence query into a set of k-mers and then applies (647) the query to a hierarchical bloom filter tree to detect a candidate chimeric biomolecule sequence in an experimental set of sequencing data. Given a query sequence q and a hierarchical bloom filter tree data structure T, sequencing data sets (at the leaves) that contain q can be found by breaking q into its constituent set of k-mers Kq and then flowing these k-mers over T starting from the root. At each node u, a bloom filter b(u) at that node is queried for each of the k-mers in Kq. If more than θu|Kq| kmers are reported to be present in b(u), the search proceeds to the two children of u, where θu is a node-specific cutoff between 0 and 1 governing the stringency required of the match. If fewer than that number of k-mers are present, a subtree rooted at u is not searched further (it is pruned).

When a search proceeds to the children, in accordance with a number of embodiments, the children are added to a queue for eventual processing. Even though there may be a large frontier of nodes that are currently active, the memory usage for querying is the trivial amount of memory needed to store the tree topology plus the memory needed to store the single current filter. If querying is parallelized in the natural way by having each thread pull an active frontier node off the single shared queue, the memory usage grows to a single filter per thread, although handling multiple threads simultaneously reading bloom filters from disk needs to be implemented with care to avoid 10 contention.

If several queries are to be made, they can be batched together so that a collection C={Kq1, . . . , Kqt} of queries starts at the root, and only queries for which |b(u) ∩Kqi|>θu|Kqi| are propagated to the children. When C becomes empty at a node, the subtree rooted at that node is pruned and not searched further. The main advantage of batching queries in this way is locality of memory references. If b(u) must be loaded from disk, it need be loaded only once per batch C rather than once per query. Batch queries can be parallelized in the same way as non-batched queries by storing with the nodes on the queue the indices of query sets that remain active at that node. Additionally, batch queries offer an alternative means of parallelization where the query collection C is split evenly among active threads that merge results for the final query results.

Candidate chimeras that are detected (649) in a hierarchical bloom filter tree are stored and/or reported. As is discussed herein, candidate chimeras can be used for experimental analyses and conclusions, diagnostics, and/or further experimentation.

While specific examples of processes for querying a hierarchical bloom filter tree data structure are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for querying a hierarchical bloom filter tree data structure appropriate to the requirements of a given application can be utilized in accordance with various embodiments of the invention.

Systems of Chimeric Sequence Unveiling

Figure 7:
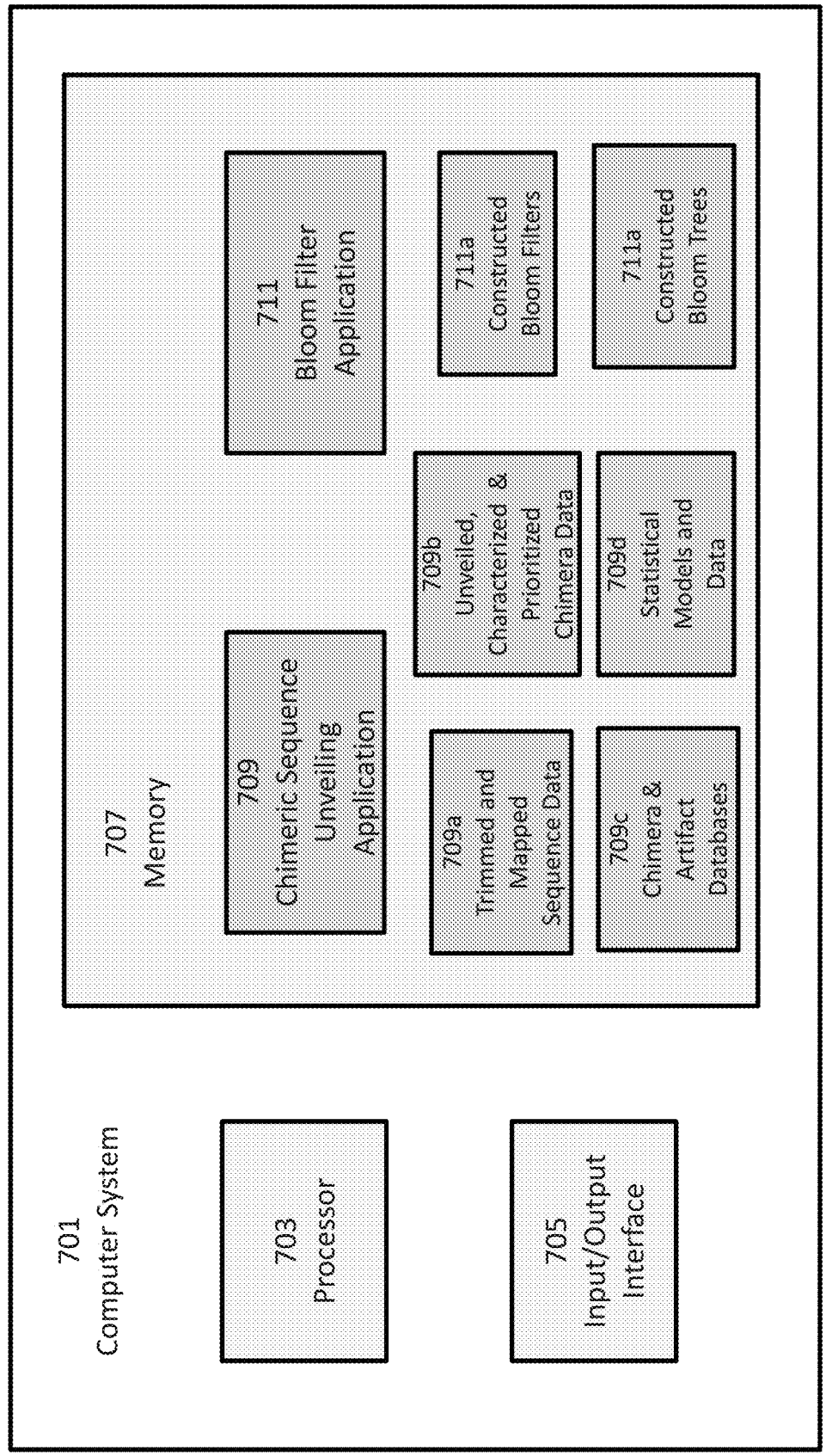
FIG. 7 illustrates a diagram of a computing system configured to unveil chimeric biomolecule sequences in accordance with various embodiments of the invention.

Turning now to FIG. 7, a computing system (701) may be implemented on a single or a plurality of computing device(s) in accordance with some embodiments of the invention. The computing system (701) may be a personal computer, a laptop computer, any other computing device with sufficient processing power, or any plurality and/or combination of computing devices for the processes described herein. The computing system (701) includes a processor (703), which may refer to one or more devices within the computing system (701) that can be configured to perform computations via machine readable instructions stored within a memory (707) of the computer system (701). The processor may include one or more microprocessors (CPUs), one or more graphics processing units (GPUs), and/or one or more digital signal processors (DSPs).

In a number of embodiments of the invention, the memory (707) may contain a chimeric sequence unveiling application (709) and bloom filter application (711) that performs all or a portion of various methods according to different embodiments of the invention described throughout the present application. As an example, processor (703) may perform a chimeric sequence unveiling method similar to any of the processes described above with reference to FIG. 2 and a bloom filter process similar to any of the processes described above with reference to FIG. 3, during which memory (707) may be used to store various intermediate processing data such as trimmed and mapped sequence data (709a), unveiled, characterized, and prioritized chimera data (709b), chimera and artifact databases (709c), statistical models and data (709d), constructed bloom filters (711a), and constructed hierarchical bloom tree data structures (711b).

In some embodiments of the invention, the computer system (701) may include an input/output interface (705) that can be utilized to communicate with a variety of devices, including but not limited to other computing systems, a projector, and/or other display devices. As can be readily appreciated, a variety of software architectures can be utilized to implement a computer system as appropriate to the requirements of specific applications in accordance with various embodiments of the invention.

Although computer systems and processes for chimeric sequence unveiling and performing actions based thereon are described above with respect to FIG. 7, any of a variety of devices and processes for data associated with unveiling of chimeric sequences as appropriate to the requirements of a specific application can be utilized in accordance with many embodiments of the invention.

Applications of Chimeric Biomolecules

Various embodiments are directed to development of research tools, diagnostics, and medicaments related to the chimeras unveiled by statistical methods. As such, novel unveiled chimeric sequences can be transformed into various synthetic biomolecules.

In many embodiments, statistical methods can unveil sequences of chimeric biomolecules. These novel sequences, which incorporate a chimeric fusion point, can be used as a template to create synthetic nucleic acid polymers having substantially the same sequence as the candidate chimeric biomolecule. Likewise, synthetic nucleic acid polymers having substantially the same complementary sequence as the candidate chimeric biomolecule sequence can also be created. In numerous embodiments, the synthetic nucleic acid is composed of DNA or RNA bases. It should be understood, however, that other synthetic bases suitable to substitute for canonical nucleic bases can be used. These bases include, but are not limited to, locked nucleic acids, dideoxy nucleic acids, or modified bases (e.g., methylation).

Multiple embodiments are directed to synthetic nucleic acids synthesized in in vitro synthesizers (e.g., phosphoramidite synthesize), bacterial recombination system, or other suitable methods. Furthermore, the synthesized nucleic acids can be purified and lyophilized, or kept stored in a biological system (e.g., bacteria, yeast). For use in a biological system, the synthetic nucleic acids can be inserted into a plasmid vector, or similar. The plasmid vector can also be an expression vector, wherein a promoter and 3'-polyA tail is combined with the chimeric sequence.

Purified synthetic nucleic acid polymers can also be chemically modified for various purposes. For example, fluorescent probes, small molecule drugs, or enzymes can be covalently attached to nucleic acid polymers. Accordingly, numerous embodiments are directed to synthetic nucleic acid polymers having a covalent attachment.

Embodiments are also directed to expression vectors and expression systems that produce chimeric RNA, and further produce chimeric peptides or proteins. These expression systems can incorporate an expression vector, as described above, and to express chimeric biomolecules in a suitable expression system. Typical expression systems include bacterial (e.g., *E. coli*), insect (e.g., SF9), yeast (e.g., *S. cerevisiae*), animal (e.g., CHO), or human (e.g., HEK 293) lines. Chimeric RNA and or protein can be purified from these systems using standard biotechnology production procedures.

In addition, many embodiments are also directed to the use of biomarkers to detect a chimeric biomolecule and/or diagnose a biological sample (e.g., clinical biopsy). Multiple methods are well known and can be used to detect a chimeric RNA molecule, such as, for example, hybridization, polymerase proliferation (e.g., PCR), or next-generation sequencing. In any of these exemplary assays, chimeric DNA or RNA could be detected by extracting the molecules from a sample or biopsy and then detected further downstream.

Multiple embodiments also incorporate methods to unveil DNA rearrangements with high precision. Many embodiments may detect, for example, viral or other pathogen sequences, or cancer from an appropriate biopsy.

Many embodiments are directed to genetically modified cells that incorporate unveiled chimeric biomolecules. In particular, embodiments are directed to a drug screening platform in which genetically modified cells can be used to identify molecules (e.g., small molecules, biomolecules) that can mitigate, inhibit or even revert a neoplastic phenotype.

Antigen Binding Molecule Development & Purification

In accordance with a number of embodiments, antigen-binding molecules (e.g., antibodies) can be developed with high specificity, preference and affinity for chimeric biomolecules that are antigenic (e.g., proteins, peptides, nucleic acids). In many of embodiments, high affinity antigen binding molecules are developed using chimeric biomolecules, such as those described herein. Many embodiments are also directed to the use of chimeric biomolecules to select and/or purify antigen-binding molecules, as determined by their specificity, preference, and/or affinity. A chimeric biomolecule, in many cases, is a neoantigen (i.e., de novo antigen arising in a neoplasia). Accordingly, in several embodiments, an antigen-binding molecule is capable of binding neoantigens within a neoplasia Antigen binding molecules can be any antibodies, fragments of antibodies, variants, and derivatives thereof capable of specifically binding an antigen. These include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, and fragments produced by a Fab expression library.

By "specifically binds," or "specifically recognizes," used interchangeably herein, it is generally meant that an antigen binding molecule (e.g., an antibody) binds to an epitope via its antigen binding domain and that the binding entails some complementarity between the antigen binding domain and the epitope. According to this definition, an antibody is said to "specifically bind" to an epitope when it binds to that epitope, via its antigen-binding domain more readily than it would bind to a random, unrelated epitope.

By "preferentially binds," it is meant that an antigen-binding molecule (e.g., antibody) specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

As used herein, the term "affinity" refers to a measure of the strength of the binding of an individual epitope by the antigen-binding molecule.

Antibodies are composed of a light chain and heavy chain. In general, the light and heavy chains are covalently bonded to each other, and the "tail" portions of the two heavy chains are typically bonded to each other by covalent disulfide linkages. Non-covalent linkages between two heavy chains can be used instead of disulfide linkages, which is typical when the antibodies are generated in culture.

Both the light and heavy chains are divided into regions of structural and functional homology, such as the constant and variable domains. The variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fe receptor binding, complement binding, etc.

The antigen recognition of the VL and VH domains is determined by the complementarity determining regions (CDRs). In naturally occurring antibodies, there are six CDRs, which are short, non-contiguous sequences that are specifically positioned to form the antigen-binding domain. An antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, Chothia and Lesk, *J. Mol. Biol.* 1987 196, 901-917, which is incorporated herein by reference).

Antibody Acquisition by Immunization

Figure 8:
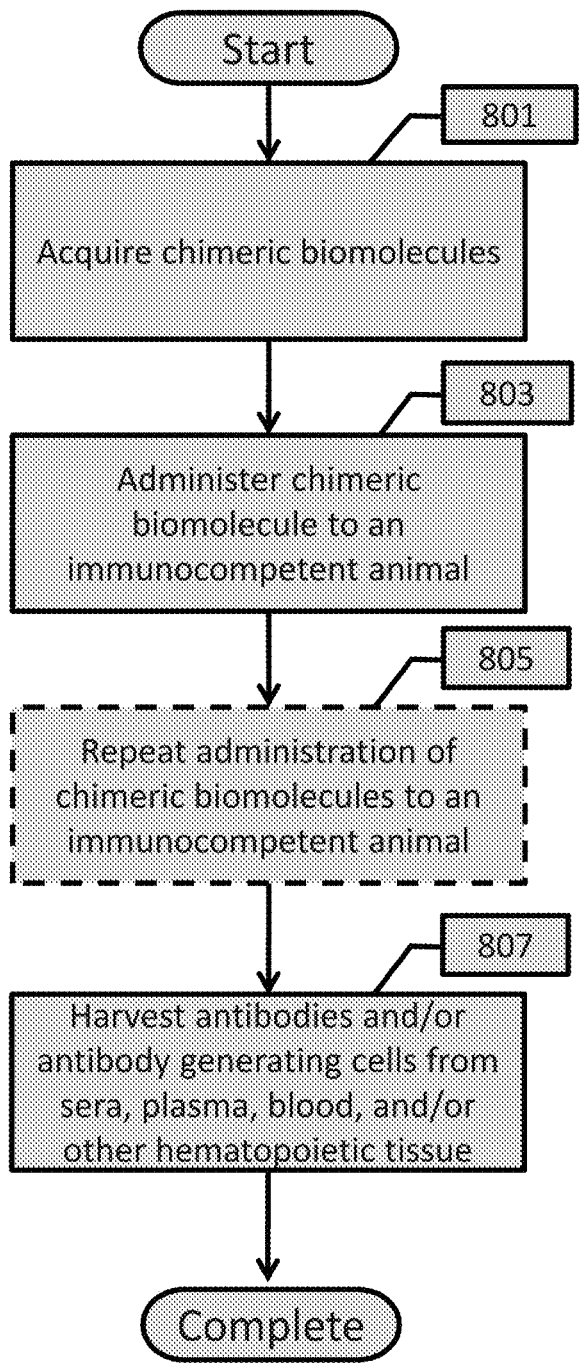
FIG. 8 illustrates a process for developing polyclonal antibodies having affinity for a candidate chimeric biomolecule in accordance with an embodiment of the invention.

An embodiment for the production of antibodies with high affinity for a chimeric biomolecule is depicted in FIG. 8. Process 800 begins with an acquisition (801) of chimeric biomolecules. As described herein, chimeric biomolecules can be produced by a number of methods known in the art. For example, chimeric nucleic acids can be produced in in vitro synthesizers (e.g., phosphoramidite synthesize), bacterial recombination system, or other suitable methods. Likewise, chimeric proteins or peptides can be recombinantly produced in an appropriate expression system, such as bacterial (e.g., *E. coli*), insect (e.g., SF9), yeast (e.g., *S. cerevisiae*), animal (e.g., CHO), or human (e.g., HEK 293) lines.

Process 800 administers (803) immunocompetent animals with an immunogenic cocktail having chimeric biomolecules. Any immunocompetent animal can be used, such as, for example, human, rabbit, goat, mouse, rat, chicken, or guinea pig. Immunocompetent animals can be administered with a stimulating amount of with chimeric biomolecule, with or without conjugate and with or without adjuvant. A stimulating amount of chimeric biomolecule is the amount required to stimulate an immune response that results in production of a collectable amount of antibodies that have affinity for the chimeric biomolecule. The stimulating amount may also depend on the use of conjugate and/or adjuvant. Any appropriate conjugate can be used, such as, for example, hemocyanin. Likewise, any appropriate adjuvant can be used, such as, for example, complete Freund's adjuvant.

Administration (805) of chimeric biomolecules into an immunocompetent animal can be optionally repeated. Often, repeat administrations can improve antibody production. The appropriate amount of administrations depends on the application, however, typically one, two, three, or four administrations are performed.

Sera, plasma, blood, and/or other hematopoietic tissue having high affinity antibodies and/or antibody generating cells are harvested (807) from immunocompetent animals at an appropriate amount of time after the final administration of chimeric biomolecules. The appropriate amount of time is the time required for the immunocompetent animal to have an immune response and generate antibodies, which is dependent in part on the immunocompetent animal used. For example, an appropriate time to harvest antibodies from rabbits is typically around 30 days after last immunization. Harvesting of sera, plasma and/or blood can be performed by any of the many methods known in the art.

Once sera, plasma, blood and/or hematopoietic tissue having high affinity antibodies cells are harvested, antibodies may be used in their natural buffer or further purified by a number of methods in accordance of a number of embodiments. Likewise, antibody-generating cells may be cultured and/or stored in accordance with several embodiments.

Monoclonal Antibody Development

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. 1988, the disclosure of which is incorporated herein by reference. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells that have been immortalized via transformation.

In the well-known hybridoma process (Kohler et al., *Nature* 1975 256, 495; the disclosure of which is incorporated herein by reference) the relatively short-lived, or mortal, lymphocytes from a mammal (e.g., B cells derived from a human subject as described herein) are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. Each single strain produces antibodies, which are homogeneous against a desired antigen.

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen (e.g., chimeric biomolecules). The binding specificity of the monoclonal antibodies produced by hybridoma cells is determined by in vitro assays such as immunoprecipitation, radioimmunoassay (RIA), or enzyme-linked immunosorbent assay (ELISA). After hybridoma cells are identified that produce antibodies of the desired specificity, affinity and/or activity, the clones may be subcloned by limiting dilution procedures and grown by standard methods (Goding, Monoclonal Antibodies: Principles and Practice, Academic Press, 1986 pp 59-103)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Selection and Purification of Binding Molecules of a Chimeric Biomolecule

Embodiments are also directed to the selection of antigen binding molecules having high specificity, preference, and affinity for chimeric biomolecules. In various embodiments, chimeric biomolecules, such as those described herein, are used to identify and select such antigen binding molecules. Binding molecules can be used for a variety downstream applications, including, but not limited to, diagnosis and treatment of tumors and cancers.

Embodiments can begin with acquisition of antigen binding molecules. Antigen binding molecules can be obtained in a variety of methods, including those described herein. Once antigen-binding molecules are obtained, they can be screened for their specificity, preference, and affinity for chimeric biomolecules.

Many assays are known in the art to screen the specificity of antibodies for a particular antigen. These assays include, but are not limited to, Western blot, immunoprecipitation, RIA, and ELISA. Accordingly, chimeric biomolecules can be used as antigens to screen for specificity.

A number of assays are also known to determine antibody preference for a particular antigen over a similar antigen. Particularly, in this application, antigen-binding molecules that preferentially bind chimeric biomolecules with low cross-reactivity with monomers and insoluble fibrils is desired. Accordingly, specificity assays, such as those described above, can be used to directly compare antigen binding molecules' ability to bind chimeric biomolecules and near off-targets. In addition to comparison assays, direct competition assays can be performed, wherein antigen binding molecules are in contact with chimeric biomolecules and near off-targets and their preference for each antigen is determined.

Binding affinities of antigen binding molecules can be measured by a number of assays. In many of these assays, the dissociation constant (Kd) can be measured directly. Alternatively, affinity can be determined qualitatively by a number assays, including, but not limited to Western blot, immunoprecipitation, RIA, and ELISA.

EXEMPLARY EMBODIMENTS

Bioinformatic and biological data support the methods and systems of unveiling chimeric molecule sequences and applications thereof. In the ensuing sections, exemplary computational methods and exemplary applications related to unveiling chimeric molecule sequences are provided.

Unveiling of Chimeric Molecules via MACHETE

Figure 9:
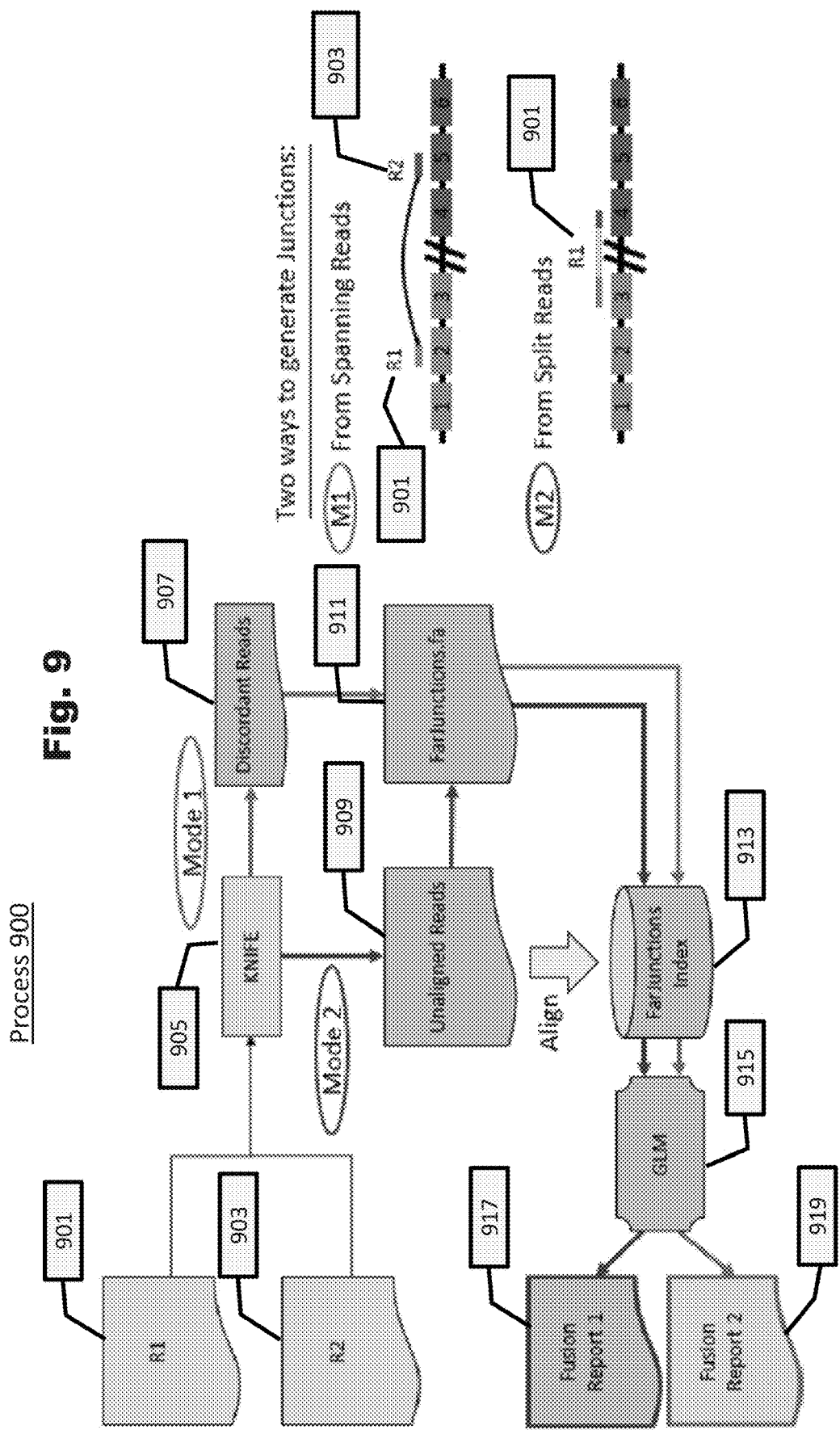
FIG. 9 illustrates a process for unveiling chimeric biomolecule sequences in accordance with an embodiment of the invention.
Figure 10:
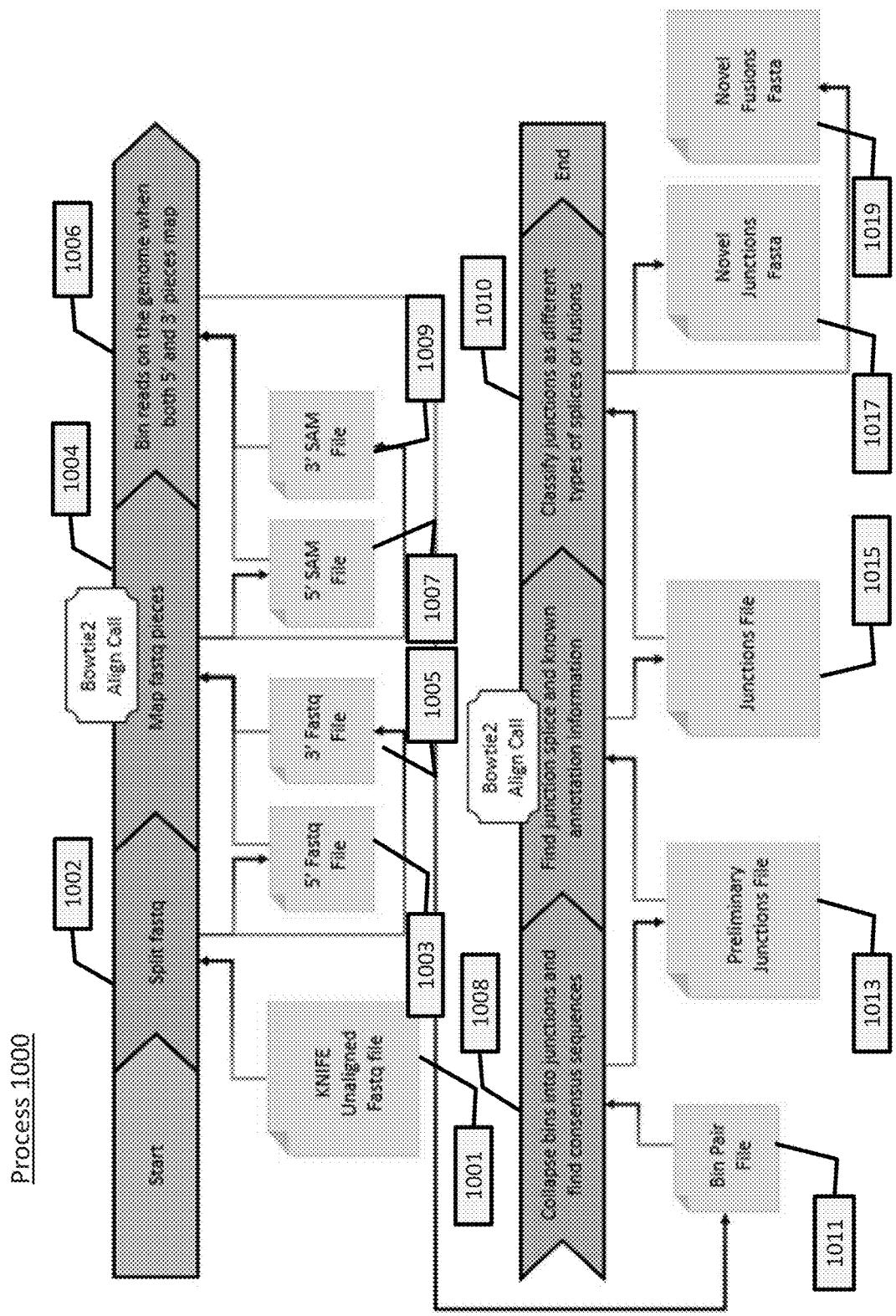
FIG. 10 illustrates a process for unveiling chimeric biomolecule sequences in accordance with an embodiment of the invention.

In a number of embodiments, chimeric sequence unveiling methods produce candidate fusion databases from discordant spanning reads. As shown in FIG. 9, exemplary process 900, also referred to as MACHETE, uses alignments of paired-end RNA seq reads output from KNIFE to generate databases of candidate chimeric sequences defined by their diagnostic exon-exon junctions (Mode 1). Reads where paired sequences of a 5' sequence end (R1 (901)) and a 3' sequence end (R2 (903)) are identified by KNIFE (905) as both aligned to the genome index, both aligned to the linear junction index (i.e., index of nucleic acid sequences spanning an exon-exon junction), or one mate aligned to the linear junction index and the other to the genome index, are evaluated and recorded as 'discordant' (907) if mates aligned more than the user-defined radius apart or on different chromosomes. These discordant reads signal that there may be a fusion junction nearby. For each discordant read pair, process 900 defines a pair of windows having a genetic distance (e.g., 20 kilobase (kb)) in the genome surrounding R1 and R2 and identify all exons with a 5' or 3' end within these windows. For each exon in the first window and each in the second, embodiments add this exon-exon junction sequence as a nominated chimeric fusion (911) to a nominated fusion (i.e., candidate chimera) database (913). Similar logic is applied when one or both read mates map to an annotated linear exon-exon junction.

Mode 1 of process 900 can screen read alignments to the KNIFE genome and linear junction indices for evidence of read pairs that span a fusion. Reads where mates (R1 and R2) both aligned to the genome, both aligned to the linear junction index, or one mate aligned to the linear junction index and the other to the genome index, are considered. The mates are termed 'discordant' if R1 and R2 map to different chromosomes or are further apart than a user-defined threshold, (e.g., 20 kb, 50 kb, 100 kb, 200 kb, 500 kb). The terms "discordant", "far junctions" ("FJ"), and "fusions" are used interchangeably. It is worth noting that because some human genes are longer than 100 kb, some fusions identified by MACHETE are compatible with linear or circular splicing from a reference genome.

Annotated exons within a 10 kb window around each of the discordant mates R1 and R2 can be used to nominate fusions, and all nominated fusions can be included in the fusion index. An exon database generated with the hg19 UCSC annotation was used in this example, but any database containing exon sequence data using a proper reference sequence annotation can be used.

There are three situations to consider when identifying these exons:
1. R1 aligned to the genome at coordinate x and R2 aligned to the genome at coordinate y. The two corresponding windows are $w_x$, spanning from x−10 kb to x+10 kb and $w_y$, spanning from y−10 kb to y+10 kb.
2. One mate aligned to the genome and the other aligned to a linear junction. For R1 aligned to the genome at coordinate x and R2 aligned to a linear junction with breakpoint coordinates $y_1$ and $y_2$, x is compared independently to $y_1$ and $y_2$. If only $y_1$ is further from x than the user-defined threshold, only one pair of windows is created, centered at x and $y_1$. If both $y_1$ and $y_2$ are further from x than the threshold, then a pair of windows is created centered at x and $y_1$, and another pair is created centered at x and $y_2$.
3. R1 aligned to a linear junction with breakpoint coordinates $x_1$ and $x_2$ and R2 aligned to a linear junction with breakpoint coordinates $y_1$ and $y_2$. All combinations of $(x_1, x_2)$ and $(y_1, y_2)$ locations are compared independently, with up to four pairs of windows created.

Each pair of windows is treated symmetrically. All exons with any overlap in $w_x$ or with any overlap in $w_y$ can be identified using the exon database generated during KNIFE index creation. For each pair of windows, a database of all exon pairs can be created. For each exon pair, sequences are concatenated and a sequence of an arbitrary length (e.g. 300) can be created by trimming or padding with Ns so the exon-exon breakpoint lies at the center.

The fusion index contains the following sequences:
150 nt from x concatenated to 150 nt from y, $\forall x \in A$, $\forall y \in B$
150 nt from y concatenated to 150 nt from x, $\forall x \in A$, $\forall y \in B$ The sense of these fusion sequences is the actual sequence of exons (i.e. is 'transcript-centric'), in contrast to KNIFE, in which the reverse complement sequence from antisense exons is used in junction indices. Also in contrast to KNIFE, exon x and exon y need not be transcribed from the same strand.

Various other embodiments of chimeric sequence unveiling methods produce candidate fusion databases from split-reads. For example, process 900 can also use split reads to generate a nominated fusion database (Mode 2), in addition to the database generated by discordant spanning reads. Unlike other methods that identify split reads using dynamic programming, such as those described in (Haas and Dobin, STAR-Fusion, 2015 (https://github.com/STAR-Fusion/STAR-Fusion/wiki), the disclosure of which is incorporated herein by reference in its entirety), process 900 can use a static definition of a split-read as a previously unaligned read whose 5'- and 3'-nucleotides (nt) map far from one another in the genome index (909). It should be noted that the read length and alignment of the read could vary, and thus the definition of a split-read should incorporate a minimum number of nts aligning to disparate loci in the genome. For example, a split-read may consist of 36 5'-nts from one locus of the genome and 36 3'-nts from a disparate locus. Note that because of the two 36 nt fragments, this exemplary split-read approach can only process input reads that exceed 71 nucleotides, but would vary depending on the definition of a split-read.

In accordance with Mode 2 of process 900, split reads can nominate candidate fusions within either R1 or R2 sequences, instead of using spanning reads described above, as described in more detail in process 1000.

Process 600B nominates split-reads as potential chimeric sequences (FIG. 6B). To begin, unaligned reads (1001) are split into 5'- and 3' fragments, and written to separate (1002) fastq files, labeled 5' Fastq (1003) and 3' Fastq (1005) respectively. These flanking sequences are then realigned (1004) to the genome using Bowtie2 to produce a 5' (1007) and 3' (1009) SAM output file. Reads that had both their 5' and 3' sequences map back successfully are then identified. The mapping location of the 5' and 3' piece of each split-read is assigned (1006) to the nearest bin of a specified genetic distance (e.g., 50 nts) and the combination of both bins is termed a bin-pair (1011). If multiple reads share the same bin-pair, they are grouped (1008) to build a consensus sequence via majority voting to mask potential sequencing errors to create preliminary junction files (1013). If this consensus sequence is consistent with an annotated exon-exon junction (1015), it is nominated (1010) as a fusion junction (1017). If it is not, the consensus is still included in the split-read fusion database (1019), but will not be included in the fusion report. The reads used to construct fusion junction sequences are considered training data and can be excluded from the unaligned reads that are subsequently aligned to the nominated fusion database. This can lead to an underestimation of the abundance of fusions nominated by split-reads, but allows a disciplined framework for statistical modeling of the fusions by separating reads used to fit and test expression of junctions, described below.

The splice site of a multi-bin consensus sequence can be identified by breaking the sequence at every position and selecting the split that generates the best (containing the fewest mismatches) upstream and downstream mapping pair to the genome. Annotations can be used to find the closest genes to the donor and acceptor of the junction consensus. A putative junction can be termed a fusion if both pieces map within a defined distance (default 2 bases) of an annotated exon boundary and the pieces map sufficiently far apart in the genome (e.g. defined threshold, default 100 kb). The sequences of nominated fusions can be constructed as described above for Mode 1. Reads used to nominate fusions by the split-read method can be removed from subsequent realignment steps.

Multiple embodiments are also directed to generation of a junction database that models chimeric artifacts in order to identify biochemical artifacts that may arise during RNA sequence library preparation. Various embodiments to unveil chimeric sequences incorporate a statistical model of several types of artifacts that can introduce false positives into fusion discovery. These artifacts include, but are not limited to, ligation artifacts and reverse transcriptase (RT) template switching artifacts. Ligation artifacts arise when two cDNAs from different RNA molecules are ligated. RT artifacts may occur when an RT enzyme initiates on one RNA molecule, dissociates and then re-initiates on a second molecule. These artifacts can appear at non-trivial rates during library preparation and produce what appears to be a sequence compatible with a fusion transcript. An innovation of various currently described embodiments is to model the rate of chimeric artifacts for each candidate fusion junction in the database. The rate of chimeric artifacts can be modeled via a realistic simplifying assumption that an artifactual read giving rise to biochemical events are equally likely to have a spurious fusion breakpoint at any point along the transcript and should not be biased to occurring at an exon-exon boundary. To model this, for each fusion junction, insertion-deletion (indel) fusion junctions were created with symmetric addition and deletion of nucleotides at the exon-exon junction.

One method to model the rate of ligation artifacts, in accordance with various embodiments, is to make a realistic simplifying assumption that a read that is a chimeric artifact is equally likely to have a "fusion breakpoint" at any point along the transcript and should not be biased to occurring at an exon-exon boundary. To model this, one can generate a set of indel fusion indices composed of 1-5 N's inserted on each side of each sequence in the fusion FASTA database, as well as 1-5 nt symmetric deletions on each side of the junction breakpoints in the fusion indices.

For Example, below is a sequence in the fusion index with | as the breakpoint:

```
                                      (Seq. ID Nos. 1 & 2)
    AAGTATTTTCAAAGAATTT | CCATATTTCAACTATATACA
```

A pair of sequences would be created in each of the following 5 index indices:

```
Indels1:
                                        (Seq. ID Nos. 3-6)
(ins)     AAGTATTTTCAAAGAATTTN  | NCCATATTTCAACTATATACA (del)     AAGTATTTTCAAAGAATT    |  CATATTTCAACTATATACA Indels2:
                                        (Seq. ID Nos. 7-10)
(ins)     AAGTATTTTCAAAGAATTTNN | NNCCATATTTCAACTATATACA (del)     AAGTATTTTCAAAGAAT     |   ATATTTCAACTATATACA Indels3:
                                       (Seq. ID Nos. 11-14)
(ins)     AAGTATTTTCAAAGAATTTNNN | NNNCCATATTTCAACTATATACA (del)     AAGTATTTTCAAAGAA      |    TATTTCAACTATATACA Indels4:
                                       (Seq. ID Nos. 15-18)
(ins)     AAGTATTTTCAAAGAATTTNNNN | NNNNCCATATTTCAACTATATACA (del)     AAGTATTTTCAAAGA       |     ATTTCAACTATATACA Indels5:
                                       (Seq. ID Nos. 19-22)
(ins)     AAGTATTTTCAAAGAATTTNNNNN | NNNNNCCATATTTCAACTATATACA (del)     AAGTATTTTCAAAG        |      TTTCAACTATATACA
```

To model the rates of indels for canonical splicing, the 5 analogous indel indices are generated using all sequences in the KNIFE linear junction indices (i.e., exon-exon junctions). Unaligned reads from KNIFE can be aligned to each of these linear junction indel indices and the information used to map to linear junction indel indices to model the probability of each read originating from a real versus artifact or chimeric. The modeled indel fusion junctions are stored in an indel fusion index.

In various embodiments, nucleic acid sequencing reads are classified as consistent or inconsistent with the fusion junction to which it aligns. After building a fusion index from either discordant spanning or split reads, reads that were classified as 'unaligned' by KNIFE are aligned to the original and indel fusion indices. For an alignment to a fusion index to be considered, the read must overlap the exon-exon junction by a user-specified number of bases. Reads that do not align to the fusion index are set aside, and can be used for alternative analysis. In cases where a read aligns to multiple fusion indices, the read is determined to align to the fusion with the best alignment score. For reads where one mate (R1 or R2) aligned to the fusion index, alignment statistics are retrieved for the other mate (R2 or R1 respectively). Paired alignments can be designated as compatible or incompatible with originating from a fusion based on the following analysis. The mate aligning to the fusion index is designated R1 and the other mate R2 for purposes of explanation only; however, all reads for which either mate aligned to the fusion index are included. If both R1 and R2 align to the fusion index, they are considered compatible only if they align to the same fusion. All R2 alignments to the scrambled junction index are considered inconsistent. R2 is "unaligned" or "unmapped" if it did not align to the genome, linear junction, scrambled junction, or fusion indices or if R2 aligned to a junction index but did not overlap the junction by the user-specified minimum. No restrictions need be imposed on the distance between the coordinates of the R2 alignment and the fusion.

In several embodiments, chimeric sequences are unveiled and prioritized by a priori statistical analysis (915). In many embodiments, processes described herein use of statistical scores to prioritize fusions based on their likelihood of being false positives. As described herein, one source of false positives is derived from the biochemical artifacts. Sequencing errors convolved with degenerate sequence motifs at exon boundaries can also result in identification of false positive junctional sequences. In addition, bona fide mutations or indels that are present within the genome of the sourced biological tissue could compound this problem, further contributing to artifacts. For example, cancer genomes are widely known to harbor many genetic mutations and indels, which could result in artifactual chimeric sequences.

Figure 11:
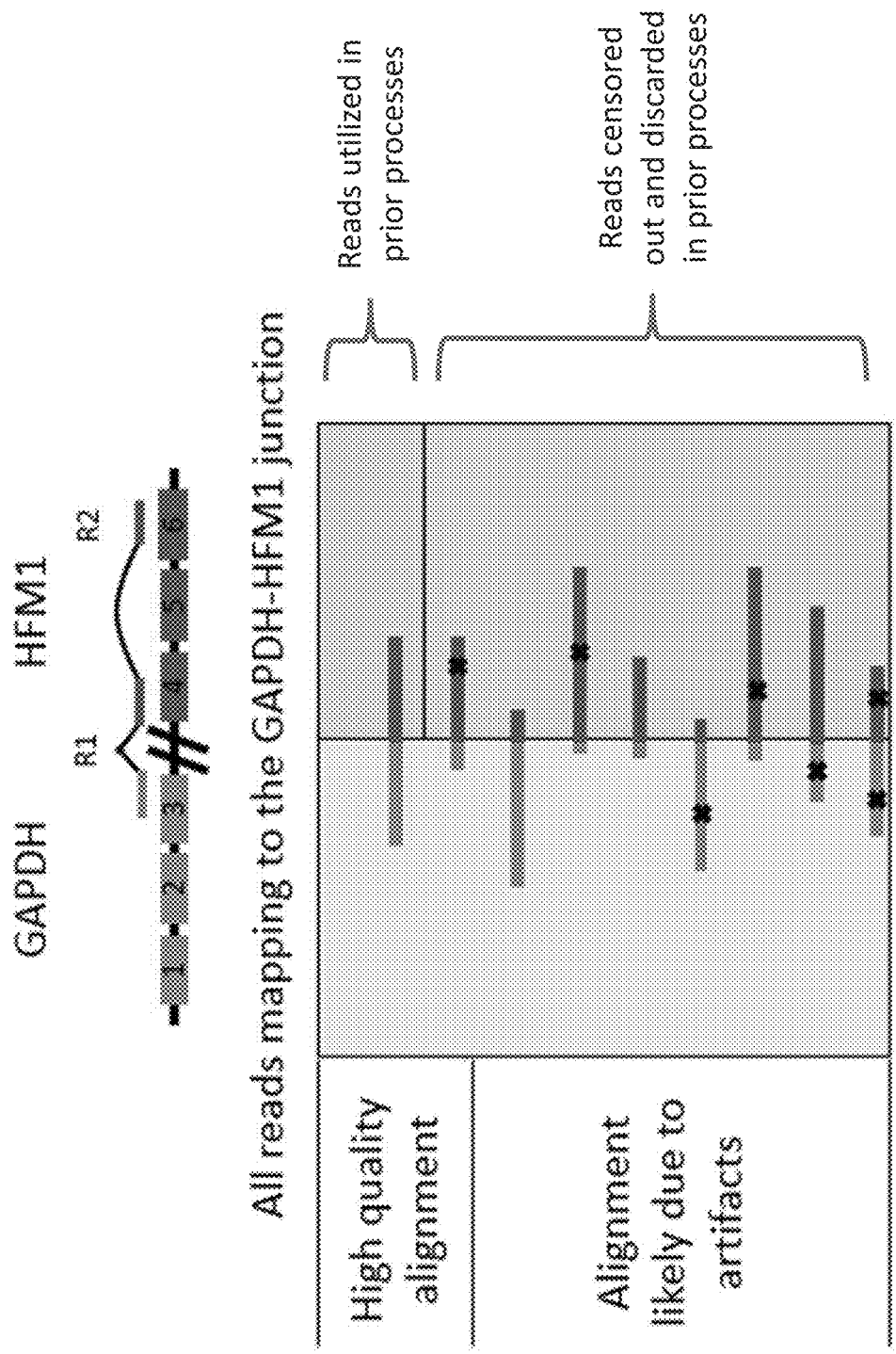
FIG. 11 illustrates an example of not discarding sequence reads via censoring in accordance with various embodiments of the invention.

One approach to address this problem is to exclude reads that align to fusions below a certain quality of alignment score or contain fewer than a certain number of nucleotides overlapping the fusion junction (FIG. 11). This procedure is called censoring, and is used by most, if not all other chimeric sequence detection methods currently in practice. In FIG. 11, GAPDH-HFM1 is given as an example of an artifactual fusion. Reads aligning to the fusion will be aggregated and used in model building and generation of a final statistical score for the fusion in the database even if they have low mapping quality, contain mismatches (depicted with X) or have a small junction overlap. In other chimeric sequence detection methods currently in common practice, reads are first censored so that only reads with few mismatches and high overlap are reported, presenting only positive data on the junction even if it is an artifact.

As depicted in FIG. 11, censoring approaches result in increasing numbers of artifactual fusions being reported as sequencing depth increases, especially among highly expressed genes. This can be due to the convolution of sequencing errors and sequence homology. If enough reads are sequenced, random errors will eventually result in reads that map to a fusion even if the fusion sequence does not exist in the input RNA.

The processes currently described herein, such as MACHETE, use a different approach. Rather than applying hard thresholds to reads that other processes would have discarded, various embodiments of processes utilize these reads to estimate the probability that each putative fusion is an artifact. The first step in this process uses the information from all reads aligning to a fusion junction, including those with poor alignment scores, reads mapping to constructed indel indices, and reads where mates map inconsistently (anomalies). MACHETE fits a generalized linear model (GLM) for each read, with predictors being alignment scores, mapping quality, and the amount of junction overlap. The GLM is used to estimate the probability, $\hat{p}$, that a read's alignment to a putative fusion was due to an artifact.

To predict a putative fusion is due to an artifact, a statistical model to discriminate "linear" and "decoy" reads is created in accordance with various embodiments of the invention. Decoy reads are those for which R1 aligned to a scrambled junction and R2 is incompatible. In this example, the GLM is fit on all decoy reads and a random subsample of 10,000 linear reads with a compatible R2 and all decoy reads in the KNIFE class input file; a seed is set so this random sampling is reproducible. The model is fit with two iterations using a re-weighting scheme. The GLM uses predictors from both R1 and R2, using the following command in R:

x=glm(is.pos~overlap+lenAdjScore+qual+len-AdjScoreR2+qualR2, data=readPredictions, family=binomial(link="logit"), weights=readPredictions[,cur_weight])

where is.pos is 1 for "linear" reads and 0 for "decoy" reads, overlap is the minimum number of nucleotides that flank each side of the junction breakpoint, qualR2 are the mapping quality, and lenAdjScoreR2 is the adjusted alignment score. The adjusted alignment score can be computed as the Bowtie2 alignment score plus the number of Ns in the portion of the junction to which the read aligned. Since short exons in the junction indices are padded with Ns, this adjustment removes the default penalty imposed by Bowtie2 (−1 for each N in the alignment) which would inappropriately penalize alignments to these short exons.

When fit on the subsample of linear reads and all decoy reads, the GLM is termed linearDecoyGLM and the p for a read r can be interpreted as the estimated probability that read r maps to a fusion that is present in the RNA sample.

Numerous embodiments are also directed to identifying and removing artifactual junctions by modeling anomaly and indel reads. For example, MACHETE can identify artifactual reads of this nature. To do so, MACHETE includes inconsistent reads that align to each junction and reads that align with indels (using alignments to companion indel junctions as described above) in assessing whether a junction is an artifact. After fitting the linearDecoyGLM, the model can use linear junctions defined by KNIFE to predict and classify these junctions as "good" or "bad" if they fall respectively into the 80% highest and 20% lowest quantiles of the distribution of junction scores, called junction_cdf.

Note that this discrimination is for linear junctions in KNIFE and junction_cdf can be computed using only reads classified as linear by the KNIFE process (without indels or anomalies). Reads aligning to indel junction indices can then be stratified as "good", or "bad" according to whether they align to linear junctions classified as "good", or "bad" and used to fit the IndelGLM model. If either class contains fewer than 20 reads, the linearDecoyGLM model is used as the IndelGLM model. Each read aligning to a fusion indel sequence can be assigned a p̂ by the GLM. Similarly, anomaly reads can be stratified according to whether they align to linear junctions classified as "good" or "bad" and are used to fit the AnomalyGLM model, which is then used to predict p̂ for reads classified as anomalies.

The per-read probabilities estimated by the GLM are aggregated to generate a cumulative score for each nominated fusion, which is compared to a null distribution. MACHETE constructs a null distribution for each value of N, the number of reads aligning to the fusion junction, by randomly sampling from the empirical distribution of p̂ for all reads in the sequencing library when N is small, and uses the Hoeffding combinatorial central limit theorem to estimate this distribution for large N (Hoeffding, *Ann Math Stat*, 22:558-66, 1951, the disclosure of which is incorporated herein by reference in its entirety). Comparing the cumulative score for each junction to the null distribution results in assignment of a junction value to each fusion junction.

For each junction, a value is assigned to nominate anomalous or indel reads in accordance with many embodiments. For example, a value can be assigned using the product p-hat (pP) equation:

$$_pP = \prod_{i \in L} \hat{p}_i \prod_{i \in A} \frac{\hat{p}_i}{\hat{p}_i + 1} \prod_{i \in D} \frac{\hat{p}_i}{\hat{p}_i + 1}$$

where L is the set of all compatible paired end (PE) reads, A is the set of PE reads which are anomalies, D is the set of compatible PE reads aligning to indel sequences derived from the junction and pi is the fitted value for each read respectively in the respective GLM.

For anomaly or indel reads, which are assigned p̂, the following transformation can be applied:

$$\frac{\hat{p}}{1 + \hat{p}}$$

as the contribution to the pP. Intuitively, this says that given the observation of an anomaly or indel read, the highest possible contribution of the read to the pP is 0.5. This matches the intuition that observing indel or anomaly reads for a junction decreases confidence that the junction is 'real'.

Note that pP is monotonically decreasing in the number of reads. Therefore, to assess the statistical significance of the observed value of pP, corrections can be made for sampling depth of the junction. For a fusion with n reads mapping to it, pP can be referred to the null distribution of scores derived from randomly sampling n reads from the null distribution of p̂ of all linear reads from the assigned by the linearDecoyGLM. Importantly, this controls for variability in scores due to sequencing depth alone as the null junction score distribution changes significantly for large n versus small n.

Specifically, for each n<15, the permutation distribution can be computed exactly. For n≥15, this value can be approximated using the normal distribution (permutation CLT) which holds for large n using the approximation:

$$\sqrt{n}\left(\frac{\log(_pP) - \mu}{\sigma}\right) \sim N(0, 1)$$

for n reads where:

μ=mean(log p̂$_i$) and σ=var(log p̂$_i$)

The fraction of the sampling distribution smaller than or equal to pP is denoted "junction_cdf" and describes the estimate of the cumulative probability that the fusion junction would receive less than or equal to its observed value under simple random sampling of reads. Thus, the larger the value of junction_cdf, the less likely the value of pP would be observed if reads were sampled at random from the empirical distribution of p̂.

Numerous embodiments are also directed to unbiased identification and removal of fusions homologous to canonical splicing events. In some instances, putative chimeric sequences might not actually be fused genes, but are normal splicing events that were initially detected as chimeric sequences. For example, MACHETE uses unbiased bioinformatic prediction to identify putative fusion junctions that are likely to be artifacts due to having a high degree of sequence homology with the reference genome or exonic linear or circular RNA splice junctions. Once putative fusion sequences are in the database, reads originating from bona fide spliced RNA may erroneously map to such spurious junctions. As seen in an example depicted in FIG. 12, Fusion Exon 1 from Gene 1 and Fusion Exon 2 from Gene 2 align to two nearby exons of Gene 3 of reference sequences. To identify these likely artifactual fusion sequences, MACHETE aligns the sequences of candidate fusions to both the reference genome and KNIFE junction indices. The putative chimeras that have sequences that are very similar to reference annotated splice junctions or genomic sequences can be classified as "mappable fusions." These mappable fusions can be removed from the final list of putative fusions and are used to generate the null distribution of junction scores. Fusions that align to one of the KNIFE reference indices are designated "BadFJ1"=1 in the MACHETE reports, and those that did not align are designated "BadFJ1"=0.

In addition, because the annotation of the human transcriptome is incomplete, sequences in the MACHETE fusion database could align to unannotated but bona fide linear splicing events involving cryptic exons not part of an annotation. These events would not be detected by the alignments that result in classification as "mappable fusions." As a conservative method to identify putative fusions that can be explained by such un-annotated linear splicing, putative fusions remove fusions from the final list if, when split, the 5' and 3' ends of a fusion junctional sequence map to the genome within a 50 kb radius, as depicted in FIG. 8. One method of doing this, for example, is to perform split read mapping of each nominated as follows: the first and last 40 non-N base pairs from each fusion sequence are taken as pseudo R1 and R2 sequences and mapped as paired-end reads to the KNIFE genome, transcriptome, linear junction, and scrambled junction indices. Bowtie2 parameters can be, for example:

--no-unal --no-mixed --no-sq --np 0 -p 8 -I 0 -X 50000 -f -ff

These parameters limit the gap between the paired-end reads to 50,000 bases in the reference indices. Fusions that align to one of the KNIFE reference indices are designated "BadFJ2"=1 and all others are designated "BadFJ2"=0.

Figure 13:
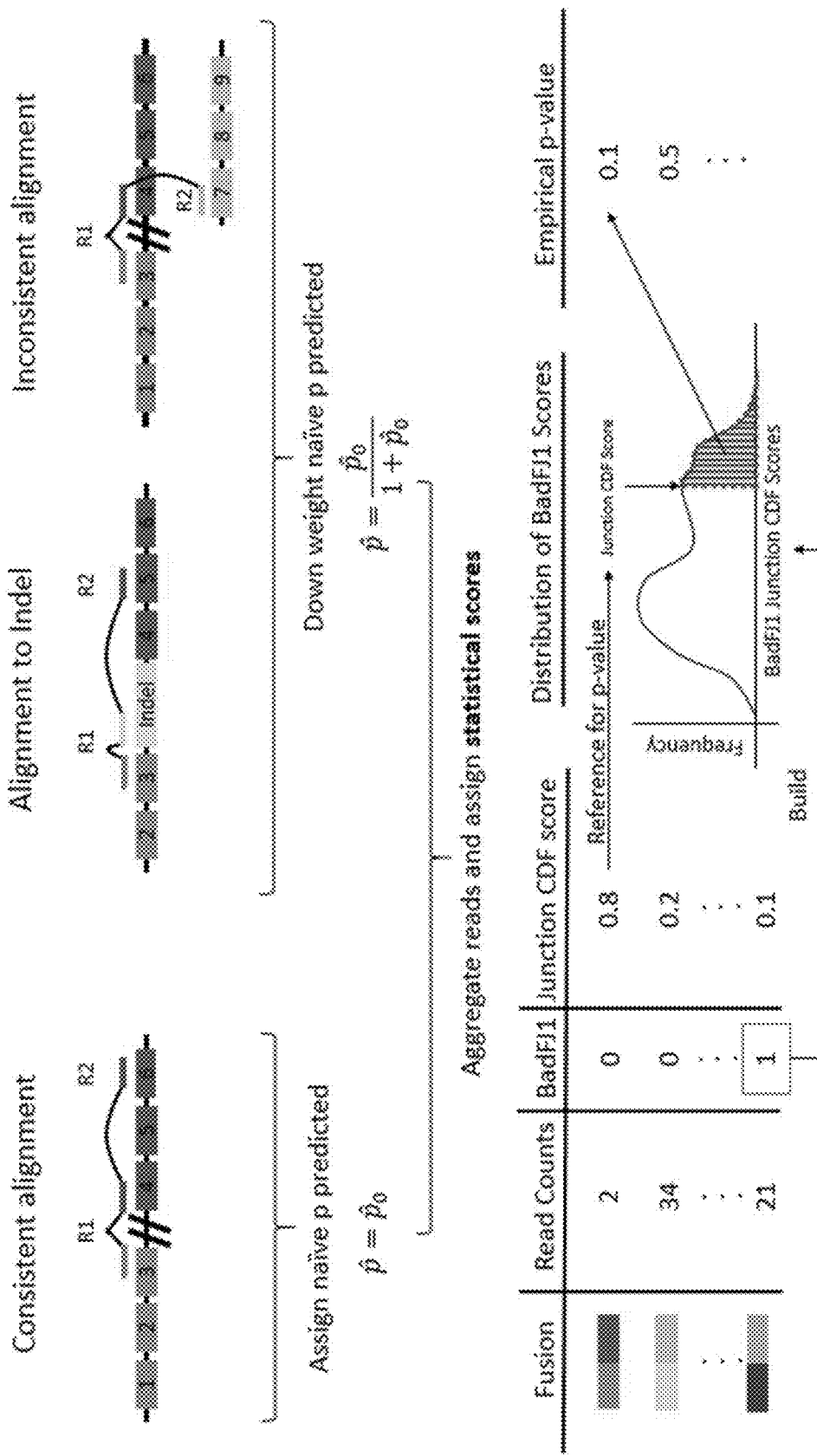
FIG. 13 illustrates an example of a priori statistical analysis in accordance with various embodiments of the invention.

More embodiments are directed to assignment of an empirical p value to the putative junctions that unveil the likelihood the junction is a bona fide chimeric sequence (915) (FIG. 13). For example, MACHETE uses a statistical framework to generate an empirical p value for each junction, resulting in an estimated probability that the junction with a given score is an artifact based on an empirical null. This value is conceptually different from the junction score because it uses a more realistic null model, accounting for structure in the null distribution lost by simple random sampling of reads that generates the junction score. Like other components in MACHETE, the empirical p value is determined by using data that would have otherwise been discarded in other chimeric sequence detection methods currently in common practice. In this case, MACHETE models the null distribution of junction scores using junctions which bioinformatic evidence supports being artifacts because they map to the genome or transcriptome ("mappable fusions," see FIG. 12). The empirical p value for each fusion junction is estimated by referring its junction score to the empirical distribution of junction scores of mappable fusions. The empirical p value can be used to determine which fusions are reported by MACHETE and to prioritize fusions for follow-up study. Additionally, standard statistical analysis of these p values could be applied to estimate a false discovery rate (FDR).

Because MACHETE typically only uses reads that fail to align to KNIFE indices, junctions in the fusion index that align to the genome or KNIFE junctions (mappable fusions, also called "BadFJ1") are likely homologous to sequences explained by RNA expression from the reference genome, and more likely to have statistical scores that mirror fusions that are artifacts. Thus, in the absence of ground truth for junctional sequences that are false positives, the distribution of junction_cdfs for mappable fusions is used as a surrogate for ground truth to model the null distribution of the junction_cdf values. The junction_cdf value for every junction with BadFJ1=0 and BadFJ2=0 is then referred to this distribution, computing an empirical p value. Note that junctions with BadFJ2=1 are likely to reflect junctions that are un-annotated linear spliced transcripts and would be expected to have generally higher values of junction_cdf so are not used to model the empirical p value. After choosing a threshold on the empirical p value, this value is used in our criteria for calling a fusion as expressed. Defining c=junction_cdf(i) for a fusion that has BadFJ1=BadFJ2=0, this simple estimate is given as:

$$\hat{p}_0 \left( \frac{\sum_{j \in BadFJ1=1} 1_{junction_{cdf(j)} \leq c}}{\sum_{j \in BadFJ1=1} 1} \right)$$

In this example, for a junction to be considered a fusion and reported back in the final reports, two or more reads classified as unaligned by KNIFE must map to the junction, the empirical value must be less than 0.1 and the junction_cdf must be greater than 0.2. Alternatively, if only one read from the reads classified as unaligned by KNIFE maps to the junction, the junction_cdf computed using the lower confidence interval (2 standard deviations) for $\hat{p}$ and pP must both be greater than 0.5 to report the junction as a fusion. Accordingly, these results are revealed in a Fusion Report (917, 919).

Benchmarking MACHETE Against Non-a Priori Methods of Unveiling Chimeras

Figure 14:
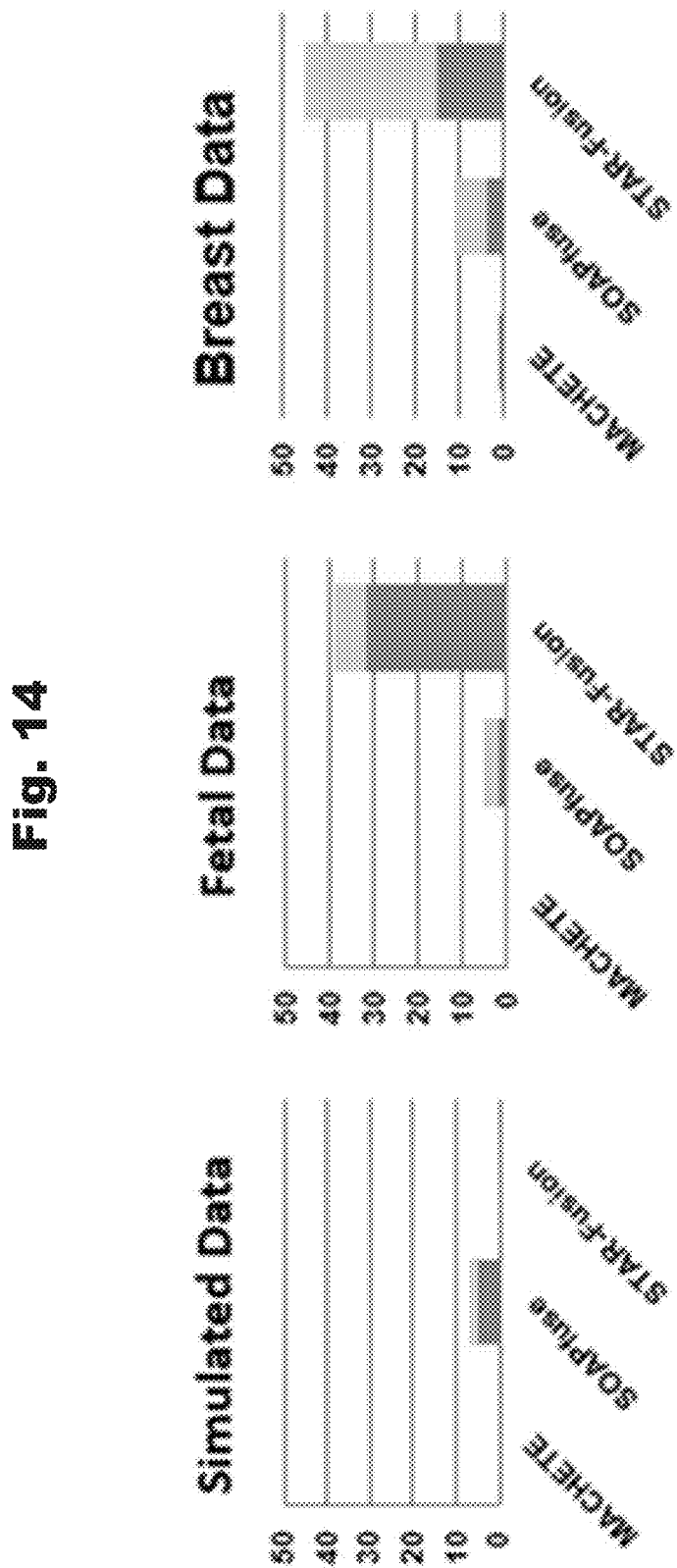
FIG. 14 illustrates multiple graphs detailing chimeric sequence unveiling sensitivity and accuracy of various methodologies generated in accordance with a number of embodiments of the invention.

MACHETE has been benchmarked against SOAPfuse (and STAR-Fusion (Jia et al., *Genome Biol*, 14:R12, 2013; *Hass and Dobin*, cited supra; the disclosures of which are incorporated herein by reference in its entirety). SOAPfuse achieved the best balance between sensitivity and specificity amongst commonly used techniques according to recent independent benchmarks (S. Kumar et al., *Sci. Rep.*, 6:e21597, 2016; S. Liu et al., *Nucleic Acid Research*, 44:e47, 2016; the disclosures of which are incorporated herein by reference in its entirety). These methodologies were tested using publicly available data for three cancer types: i) 2 independent datasets from the BCR-ABL1 positive cell line K562, ii) data from 2 distinct patient-derived Ewing's sarcoma cell lines, and iii) the ovarian cancer cell line OVCAR3. The highest ranked fusions nominated by MACHETE in OVCAR3 were assessed, and 3/3 predictions were validated. None of the three nominated fusions have previously been reported. When tested, SOAPfuse only detected 1/3 and STAR-Fusion detected 2/3. These methodologies were tested on three negative control datasets: i) forty three samples from eight normal human fetal tissue types, ii) three normal breast organoids, and iii) two datasets simulated from the human reference transcriptome under two different parameter regimes. Using the same statistical thresholds that give high true positive rates in the cancer samples, MACHETE has an unprecedented low false positive rate, reporting only one false positive fusion among all of the negative controls. This is a significant advance over SOAPfuse and STAR-Fusion which each report large numbers of distinct fusions in the same samples (FIG. 14).

The vast majority of validated gene fusions, including the BCR-ABL and EWS-FLI fusions described herein, occur at exon-exon boundaries. MACHETE only detects fusions at exon boundaries, and these stringent criteria improve specificity of SOAPfuse and STAR-Fusion by eliminating some false positive fusions in normal samples. In order to directly compare the results of fusion algorithms each designed to detect a distinct, but significantly overlapping, subset of all potential fusions, a uniform set of filtering criteria was imposed on the results of SOAPfuse, STAR-Fusion, and MACHETE. These criteria are 1) fusions must be reported at exon-exon boundaries; 2) read pairs have to occur more than 1 Mb apart or on different chromosomes. MACHETE results are additionally filtered based on a priori statistical scores, which are not provided by other methods. To assess the effect of imposing a commonly used threshold of more than one read on the false positive rate for all methods, results were compared using all junctions fulfilling the above criteria or the subset of those junctions with more than one mapping read. For the benchmarking experiments, the number of fusions found by a method in the form of "Q|R" to where Q is the unfiltered count, and R is the filtered count is reported below. In addition, the number of fusions detected by a method in the form of "Q|R" where Q is the filtered count without using the read count threshold, and R is the filtered count with the read count threshold is reported below.

MACHETE Significantly Improves Specificity on Negative Controls

Specificity was evaluated using standards previously applied by third party assessments of fusion detection methods (Yoshihara et al., *Oncogene*, 34:4845-54, 2015, the disclosure of which is incorporated herein by reference in its entirety). Namely, a fusion detection method with high specificity should find no fusions in data simulated from the reference human transcriptome. In normal samples, the algorithm should also rarely, if ever, find interchromosomal fusions, with exceptions occurring only when cryptic translocations have occurred. Because such events are thought to be exceptionally rare, it was assumed that interchromosomal fusions reported by methods in normal samples are artifacts. A subset of individuals harbor local tandem duplications in their genomes, copy number variants (CNVs), that could in principle interrupt protein coding genes and result in gene fusions. However, these events are also considered to be rarely detected in normal cells, especially between exons separated by more than 1 Mb.

FIG. 14 depicts the number of fusion isoforms detected by MACHETE, SOAPfuse, and STAR-Fusion in negative control data. In the simulated data, MACHETE and STAR-Fusion reported only three fusions, all of which were TOP3B-PI4KA isoforms that were included in the simulated ground truth (true positives). SOAPfuse found one of the three fusions, but reported an additional 715 fusions that were not in the simulated data (false positives).

In normal fetal RNA, MACHETE reported no fusions in 43 samples. In the same data, SOAPfuse reported 512 fusions, while STAR-Fusion reported 39132 fusions. In normal breast organoids, SOAPfuse detected 1114 fusion isoforms and STAR-Fusion detected 45115 fusions. In the same data, MACHETE reported a single potential fusion, MBNL2-GNAS, which was also reported by SOAPfuse.

While STAR-Fusion matched the specificity of MACHETE on simulated data, it reported many more presumed false positives than MACHETE or SOAPfuse in normal samples. These results underline the significant improvement in specificity achieved by MACHETE on both real and simulated data.

MACHETE Improves Positive Predictive Value Compared to Current Best Performing Processes The sensitivity and Positive Predictive Value (PPV)=TP/(FP+TP) of MACHETE was compared to the top performing algorithms from S. Kumar et al. (cited supra) and S. Liu et al. (cited supra) in a context where the ground truth is known. Third party simulated data from the negative control of Engstrom simulation 1 (P. G. Engstrom et al. Sci. Rep. 3:1689, 2013) that lacked any gene fusions was used as negative control data, and concatenated all reads from the positive control dataset containing 50 gene fusions used in S. Kumar et al. (cited supra). In order to have uniform read lengths, the 3' most base of the reads from the Engstrom simulation 1 was removed from each read. This is referred to herein as the 'mixed' dataset.

MACHETE reported 33 of the 50 true positive fusions and 0 false positives, a sensitivity of 66% and a PPV of 100%. In contrast, the best performing algorithms from S. Kumar et al. (cited supra), EricScript (resp. SOAPfuse and STAR-Fusion) had sensitivity of 80% (74% and 84%) and PPV of 77% (71% and 91%). STAR-Fusion performs well here, having a PPV close to MACHETE. However, as discussed below, STARFusion suffers from a very high FP rate in other samples, while MACHETE maintains tight control of FPs (see FIG. 15).

Figure 16:
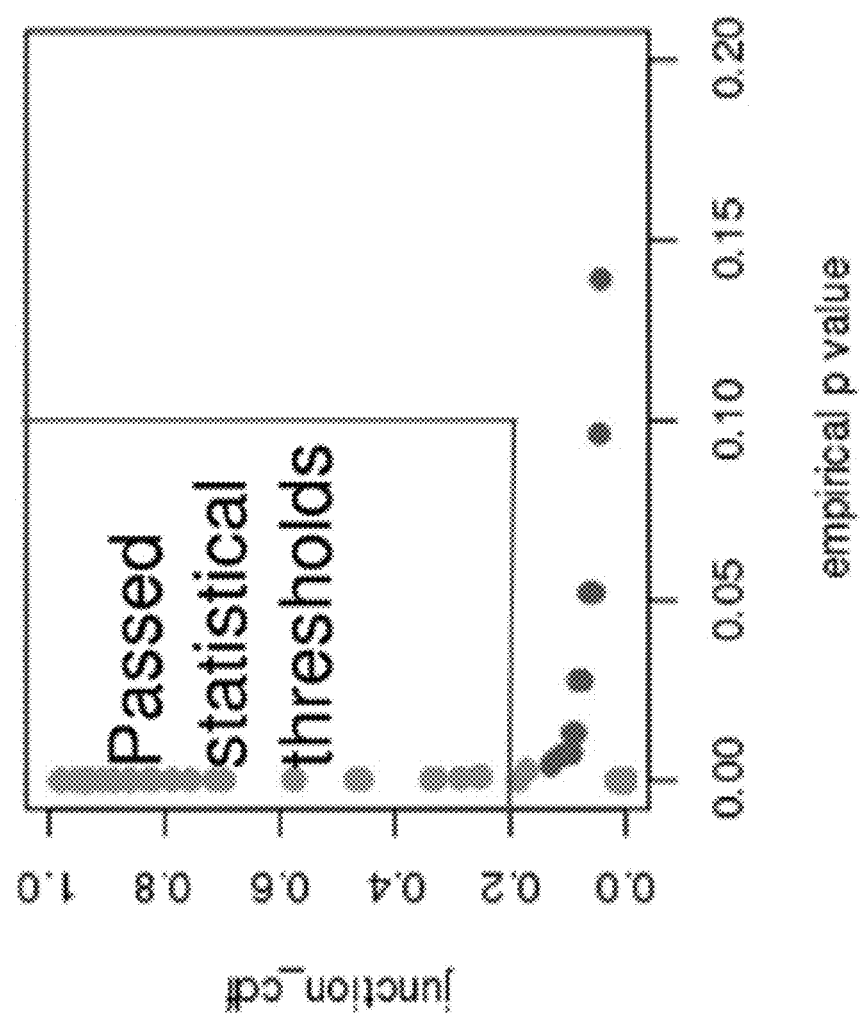
FIG. 16 illustrates a graph detailing empirical p value and junction score detailing MACHETE's ability to differentiate true positives from false positives generated in accordance with a number of embodiments of the invention.
Figure 17:
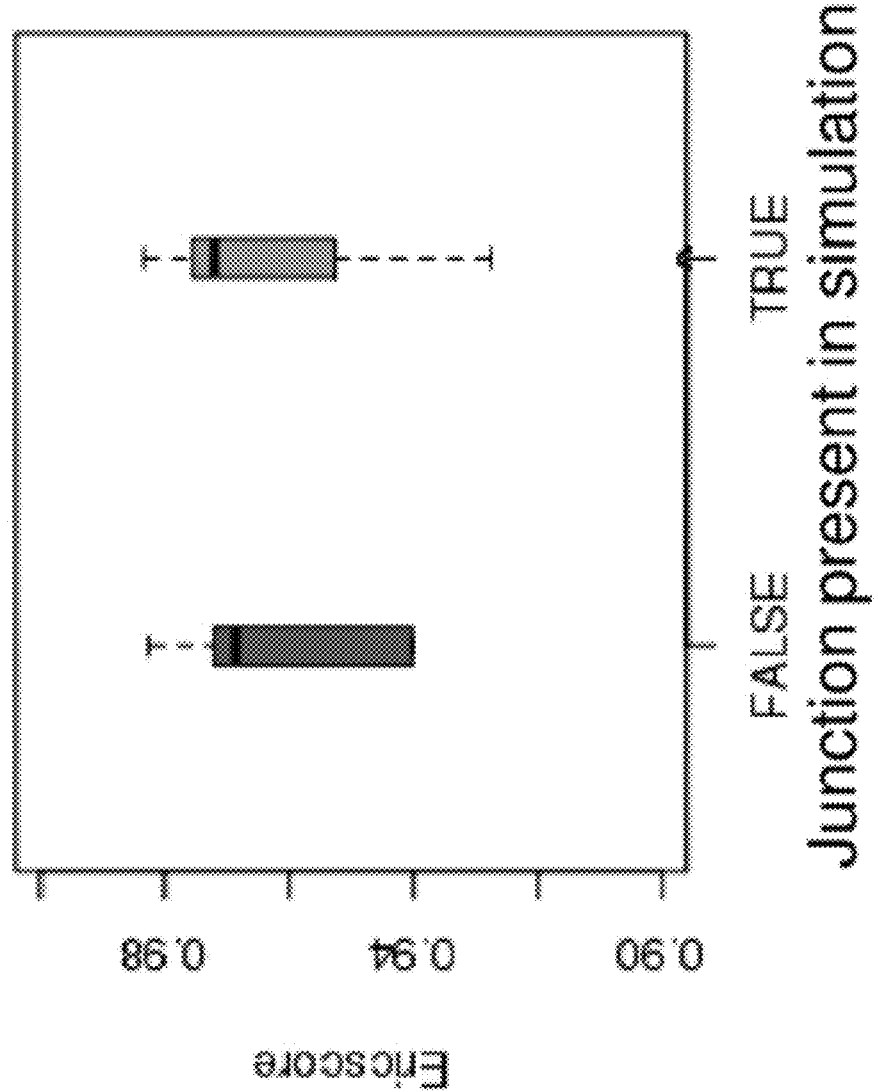
FIG. 17 illustrates a graph detailing the inability of a prior art method failing to discriminate between true positives and false positives.

The use of statistical scores by MACHETE is key to its precision and high PPV. MACHETE detects the sequences of 42 fusions in the ground truth set of fusions, but nine of them are removed based on their poor statistical scores. The distribution of empirical p values are displayed in FIG. 16 stratified by whether the fusion is a TP. FIG. 16 shows that all fusions with low empirical p values and high junction cdf scores are true positives which is why statistical scoring allows MACHETE to achieve a perfect PPV on the third-party-generated mixed dataset. These features are not true of the EricScore (FIG. 17). Even at a high threshold for the EricScore, the PPV is low and at a threshold for the score of 0.95, 31 TP and 8 FP are reported. MACHETE achieves higher sensitivity (39 fusions detected) and a PPV of 1 (0 FP detected). Finally, it is noted that MACHETE detects 42 fusions, the same sensitivity of STAR-Fusion, but assigns some TP scores consistent with them being artifacts. This behavior is predicted for any statistic used to test a hypothesis, and reflects the property that no statistical test (or statistical algorithm) can have perfect power (i.e. a power of 1).

MACHETE has Comparable Detection Efficiency of BCR-ABL1 to Other Algorithms

Increased specificity can always be achieved by shrinking a rejection region, which would correspond to more stringent thresholds imposed to accept a nominated fusion. To address the concern that MACHETE's low false negative rate could result in decreased statistical power to detect true positives, MACHETE's ability to identify positive control fusions was tested.

To test for one of the best characterized gene fusions, BCR-ABL1, and another validated fusion, NUP214-XKR3We, data derived from the chronic myelogenous leukemia (CML) cell line K562 was used (Maher et al., Proc. Natl. Acad. Sci., the disclosure of which is incorporated herein by reference in its entirety). A total of 11 replicates generated in two labs, both members of the ENCODE consortium, were analyzed. MACHETE, SOAPfuse, and STAR-Fusion were run on and compared on 10 of the replicates because SOAPfuse could not finish analysis on one.

Across all samples, the three methods detected only one isoform of each of the validated fusions, BCR-ABL1 and NUP214-XKR3. Within each replicate, these fusions were within the top three results when ranked by read count for SOAPfuse and STAR-Fusion and were consistently the top two results for MACHETE. Read count filtering did not change detection of these well-documented fusions. NUP214-XKR3 was detected in all replicates and the BCR-ABL1 fusion was identified in all replicates except SRR192416 and SRR192417 by MACHETE, SOAPfuse, and STAR-Fusion. All three methods also identified a recurrent inversion on chromosome 16 giving rise to the C16orf87-ORC6 fusion, a fusion of unknown significance.

Figure 18:
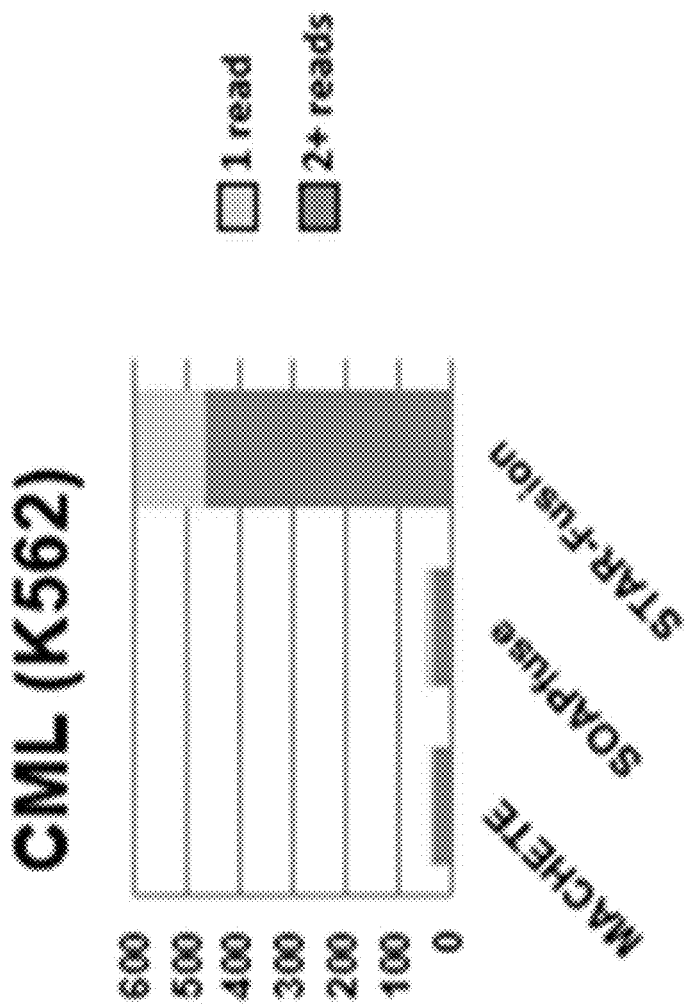
FIG. 18 illustrates a graph detailing chimeric sequence unveiling sensitivity and accuracy of various methodologies generated in accordance with a number of embodiments of the invention.

MACHETE and SOAPfuse reported a similar number of distinct fusion events across all 10 replicates (FIG. 18). SOAPfuse reported 48132 fusions, while MACHETE reported 39130 fusions. In contrast, STAR-Fusion reported 5931462 distinct fusions across these same replicates. The number of fusions reported by STAR-Fusion per replicate from biosample ENCBS087RNA (3 replicates) ranged from 13 to 125, and from 13 to 122 per replicate from biosample ENCBS088RNA (6 replicates). Given that these are all K562 cell line samples and many of the fusions reported by STAR-Fusion were detected in a single experiment, the majority of these are likely false positives.

Although SRR3192422 was excluded from the above analysis because SOAPfuse failed to complete, the fusions reported by MACHETE and STAR-Fusion were examined in this replicate. Both methods reported more fusions than in any of the other 10 replicates: 2471154 for STAR-Fusion and 57146 for MACHETE. Strikingly, BCR-ABL1 and NUP214-XKR3 remained the fusions with the highest read counts reported by MACHETE in this replicate. NUP214-XKR3 remains the top result for STAR-Fusion, but the method reported 35 other fusions with as many or more reads as BCR-ABL1 in this replicate. These results demonstrate MACHETE's ability to prioritize true positive fusions even in samples that are problematic for non-a priori methods.

MACHETE Improves Detection of Fusion Transcripts in Ewing's Sarcoma Cell Lines

Ewing's sarcoma is characterized by a translocation resulting in expression of fusion transcripts between the EWSR1 gene on chromosome 22 and the FLI1 gene on chromosome 11, or t(11;22) (q24; 12). In some tumors and patient derived cell lines, the reciprocal FLI1-EWSR1 transcripts are also expressed. The sensitivity of MACHETE's detection of the documented alternative splicing between EWSR1 and FLI1 in the Ewing's sarcoma cell lines SKMNC and A673, as well as the detection of the reciprocal fusion event between FLI1 and EWSR1 in A673 was evaluated (FIG. 19).

RNA-Seq data generated from two experiments using the cell line A673 and four experiments using the cell line SKMNC was analyzed. shRNA against FLI1, targeting the EWSR1-FLI1 fusion, and negative control shRNA against GFP were introduced into the cells using a lentiviral vector. The four SKMNC samples consisted of the following experiments: treatment of shGFP for 48 hours, shGFP for 96 hours, shFLI1 for 48 hours, or shFLI1 for 96 hours. The two A673 samples consisted of the following experiments: treatment of shGFP for 48 hours or shFLI1 for 96 hours. Successful depletion of the EWS-FLI1 fusion by shFLI1 was verified (Riggi et al. *Cancer Cell*, 26:668-81, 2014, the disclosure of which is incorporated herein by reference in its entirety), with some depletion at 48 hours, and more dramatic, but incomplete, depletion at 96 hours and no depletion of the EWSR1-FLI1 in the control shGFP treated cells. Because shRNA modulated the expression of the EWSR1-FLI1 transcripts, this dataset permitted assessment of the sensitivity of detection of EWSR1-FLI1 by the three methods in cell lines with and without knockdown of EWSR1-FLI1 transcripts.

MACHETE and STAR-Fusion detected the expression of EWSR1-FLI1 fusion transcripts in each of the six samples (FIG. 19). MACHETE also detected two additional isoforms not reported by STAR-Fusion, including a splice variant unique to the SKMNC cell line. EWSR1-FLI1 was detected by SOAPfuse in all four SKMNC experiments, but with only one supporting read in two of the experiments, and no EWSR1-FLI1 isoforms were detected by SOAPfuse in one of the A673 experiments, representing a significant shortcoming in sensitivity.

MACHETE and STAR-Fusion found the most highly expressed fusion in the control samples (shGFP) of both cell lines to be an isoform of EWSR1-FLI1, an isoform not detected by SOAPfuse in any of the control samples. The most highly expressed fusion reported by SOAPfuse in each of the control samples (shGFP) was YEATS2-GALNT, a fusion also detected by MACHETE and STAR-Fusion. STAR-Fusion reports 78 distinct fusion isoforms across all six samples, from which would be difficult to select fusions for validation. Across these samples, MACHETE reports only 16 distinct expressed fusion isoforms, including one FLI1-EWSR1 and four distinct EWSR1-FLI1 isoforms. SOAPfuse also reports 16 distinct fusion isoforms, although only two of these are EWSR1-FLI isoforms and none are FLI-EWSR1.

The A673 sample is known to express the reciprocal FLI1-EWSR1 transcript (40). SOAPfuse did not detect any fusion transcripts derived from the reciprocal translocation (FIG. 19). MACHETE detected one isoform of FLI1-EWSR1 with two reads, somewhat counter-intuitively, if samples were sequenced at comparable depth, in the shFLI1 A673 sample. STAR-Fusion detected two isoforms of FLI1-EWSR1 in this sample with only one read each.

Together, this data demonstrates that MACHETE is more sensitive and specific than STAR-Fusion in the analyzed Ewing's sarcoma data. SOAPfuse achieves a similar specificity but sacrifices sensitivity. This data also shows that thresholds of results based on read counts from fusion detection algorithms misses biologically significant gene fusions. In this case, thresholding of junctional reads would result in STAR-Fusion missing the FLI1-EWSR1 reciprocal translocation and SOAPfuse missing EWSR1-FLI1. Using these methods without read count thresholds results in significant false positives, as described in previous sections, and additionally fails to prioritize biologically important fusions.

MACHETE Discovers Novel Fusions in Ovarian Cancer Cell Line OVCAR3

All three methods were used to predict fusions in publicly available RNA-Seq data from the ovarian cancer cell line OVCAR3. Using RNA from de novo extracted from OVCAR3 cell lines, validations of the most abundant predicted fusions that passed MACHETE's statistical filters were attempted. These filters are: two splice isoforms of a translocation giving rise to a fusion between the genes SPEN and NEU1, another translocation giving rise to a fusion between NUP98 and the gene BEAN1, and a greater than 2 Mb predicted duplication resulting in a fusion between the genes ITSN2 and OTOF on chromosome 2. All three fusions, including the predicted splice variant in SPEN-NEU1, were validated by PCR using gel electrophoresis and Sanger sequencing.

SOAPfuse predicted only one fusion in each of the two OVCAR3 samples with one read each: in one sample, the fusion LINC00665-HKR1, and in the other, SPEN-NEU1. STAR-Fusion detected 27117 fusions, but failed to detect either of the two SPEN-NEU1 isoforms that were predicted by MACHETE and validated by PCR.

In the PCR validations, the ovarian cancer cell line HEY was used as a control under the assumption that the vast majority of gene fusions are neoplasm-specific. HEY was negative for all fusions tested. These results suggest the potential of finding specific but potentially significant fusions using precise de novo detection of fusion transcripts.

Description of PCR Validation Methods on Select Chimeras Unveiled by MACHETE

RNA was extracted and reverse transcribed using standard protocols. All PCRs were performed for 35 cycles, 30 second extension times using TaqSupermix and the following PCR primers. PCR products were TOPO cloned and Sanger sequencing was performed according to standard protocols.

MACHETE candidate junctions:
chr1:SPEN:16265371:+:chr6:NEU1:31829227:-:fusion
chr1:SPEN:16264501:+:chr6:NEU1:31829227:-:fusion
Primers Used for Validation of SPEN-NEU1:

```
>SPEN-NEU-F:
                                   (Seq. ID No. 23)
CACTTCGTCTCTGGCAACAA

>SPEN-NEU-R:
                                   (Seq. ID No. 24)
TGTGAGCACAAAGGGAGTAGAA
```

Sanger Sequencing Result for SPEN-NEU1:
>Clone 1:

(Seq. ID No. 25)
CACTTCGTCTCTGGCAACAACGTCCTGGCCCATCGGTCCCTGCCCCTTT

CTGAAGGAGGGCCCCCACTAAGGATCGCCCAGAGGATGCGGCTGGAGGC

AACGCAGCTGGAAGGGGTTGCCCGAAGGATGACGGCAGCACATGGTCTC

CTACAGCGTTCATTGTCAATGATGGGGATGTCCCCGATGGGCTGAACCT

TGGGGCAGTAGTGAGCGATGTTGAGACAGGAGTAGTATTTCTTTTCTAC

TCCCTTTGTGCTCACA

>Clone 2:

(Seq. ID No. 26)
CACTTCGTCTCTGGCAACAACGTCCTGGCCCATCGGTCCCTGCCCCTTT

CTGAAGGAGGGCCCCCACTAAGGATCGCCCAGAGGATGCGGCTGGAGGC

AACGCAGCTGGAAGGGGTTGCCCGAAGGATGACGGTGGAGACAGATTAC

TGTCTGCTGCTGGCTCTGCCCTGTGGCCGTGACCAAGAGGATGTTGTGA

GCCAGACCGAGTCCCTCAAGGCTGCCTTCATCACTTACCTGCAGGCCAA

GCAGGCGGCAGGGATCATCAACGTTCCCAACCCTGGCTCCAATCAGGCA

GCACATGGTCTCCTACAGCGTTCATTGTCAATGATGGGGATGTCCCCGA

TGGGCTGAACCTTGGGGCAGTAGTGAGCGATGTTGAGACAGGAGTAGTA

TTTCTTTTCTACTCCCTTTGTGCTCACA

MACHETE Candidate Junctions:
chr11:NUP98:3818629:-:chr16:BEAN1:66511462:+:fusion
Primers Used for Validation of NUP98-BEAN1:

>NUP-BEAN-R:
(Seq. ID No. 27)
TCTGGGTACAGCTCCCTGAG

>NUP-BEAN-F:
(Seq. ID No. 28)
CAGGGGACTCCTGACACTTC

Sanger Sequencing Result for NUP98-BEAN1:

(Seq. ID No. 29)
CAGGGGACTCCTGACACTTCCCCTTCCCCACCGAACCGCGTGTCGGACGA

GCACACATACAGCCGCTCAAGCCGCAGGATGCGCTATGCCTGCAGCTCCT

CAGAGGACTGGCCCCCACCCTTGGACATCAGCTCTGACGGGACGTGGAT

GCCACGGTGCTCAGGGAGCTGTACCCAGA

MACHETE Candidate Junctions:
chr2:ITSN2:24550920:-:chr2:OTOF:26739467:-:rev
Primers Used for Validation of NUP98-BEAN1:

>OTOF-R:
(Seq. ID No. 30)
AGCAGTCCATCCGTCTCTTG

>ITSN2-F:
(Seq. ID No. 31)
TGATGGCTCAGTTTCCCACA

Sanger Sequencing Result for ITSN2-OTOF:

(Seq. ID No. 32)
TGATGGCTCAGTTTCCCACAGCTATGAATGACCAGCCTGTGCGTGGAGGT

CCGGTATCAGGCCACtGACGGCACAGTGGGCTCCTGGGACGATGGGGACT

TCCTGGGAGATGAGTCTCTTCAAGAGGAAGAGAAGGACAGCCAAGAGACG

GATGGACTGCT

Scalable MACHETE Capable of Handling Big Datasets

In an exemplary embodiment, the process MACHETE can be made scalable (sMACHETE) with the use of a process hierarchical bloom filter tree known as Sequence Bloom Trees (SBTs). In performance, sMACHETE identifies gold standard positive controls, such as TMPRSS-ERG, a variety of recurrent gene fusions in acute myeloid leukemia (AML) and glioblastoma multiforme (GBM). sMACHETE predicts novel recurrent 5' and 3' partners and novel recurrent gene pairs in its list of RNA chimeras which are enriched for Catalogue of Somatic Mutations In Cancer (COSMIC) genes, while maintaining an extremely low false positive rate.

Figure 20:
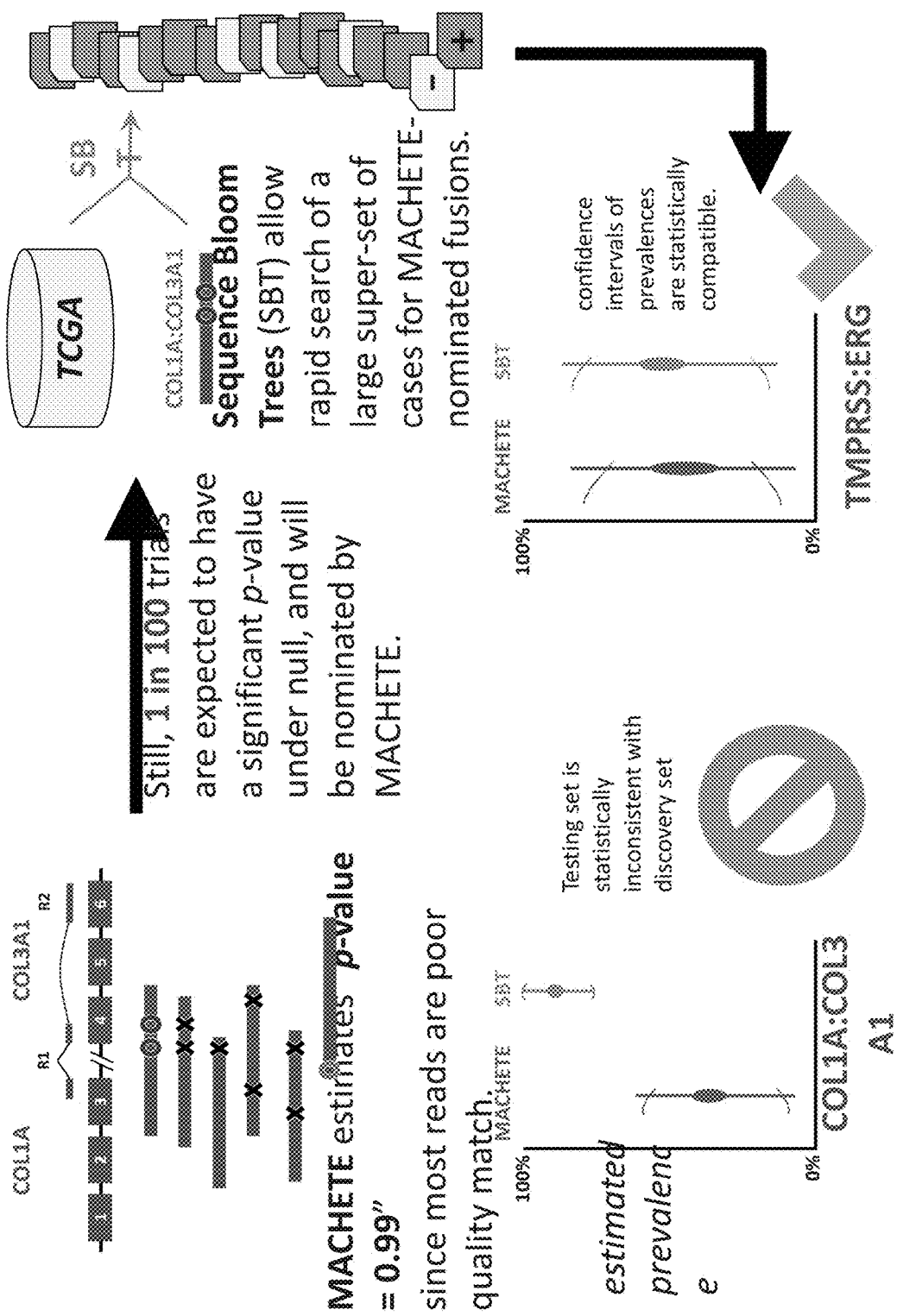
FIG. 20 illustrates an example of bloom filter efficiency in combination with a priori statistical analysis to unveil chimeric sequences in accordance with various embodiments of the invention.

As described above, MACHETE parses sequencing reads into categories that: (a) align to the genome; (b) are potential chimeras resulting from intra-genic rearrangements under 1 megabase, (c) are consistent with canonical splice junctions; or (d) cannot be aligned. Read pairs where both reads map to an index, but their coordinates are farther away than a user-defined radius (e.g., 100 kB) are used to nominate potential gene fusions defined by their diagnostic exon-exon junction. Unaligned reads are mapped to candidate fusions, and MACHETE uses reads that other chimera detection algorithms discard to model artifactual fusions and assign a statistical score to each chimera candidate (FIG. 20).

In addition to the statistical models employed by MACHETE, sMACHETE criteria for chimera significance accounting for multiple hypothesis testing when MACHETE is run on large numbers of samples. For example criteria could include: (a) no more than two of the first eight nt at in the acceptor sequence are "A"; (b) the mapping quality, i.e. uniqueness of the sequence in the genome, of both the donor and acceptor is high (see FIG. 20); (c) and a threshold on MACHETE's empirical p-value that adjusts for multiple testing of when the partners of fusions are highly expressed (see FIG. 8). For intuition, (a) is a helpful criterion because some human exons have highly degenerate sequence (for example, due to Alu exonization); (b) is a helpful criterion because other exons contain polyA stretches at the 5' most end, including those with bona fide poly(A) signals at the 5' end of an exon. Once such exons enter the MACHETE junctional database, they cannot be distinguished from (a) splicing to other Alu elements including cryptic intragenic sequences (Shen et al., 2011) or (b) premature poly-adenlyation. Excluding exons with such sequences could sacrifice some detection power but increases MACHETE's low false positive rate.

As described herein, the basic process of MACHETE for one pair of FASTQ files involves the following steps: (i) applying Trim Galore, a wrapper for CutAdapt, to the pair of files; (ii) checking for certain file-naming requirements, running the KNIFE algorithm on the pair of results from Trim Galore; (iii) running the MACHETE on the output files of the knife. The KNIFE process can be run as described in Szabo et al., or using modifications as desired by the user.

In many embodiments, runs are performed on samples for multiple cancer types. For each cancer type, the CGC Data Browser web interface, in a few cases, and, far more often, the CGC Application Programming Interface (API) were used to select RNA-Seq files to analyze. The TCGA files are pairs of FASTQ files, each pair consisting of a forward and reverse read file.

In more embodiments, the MACHETE process is run via interaction with the CGC API with an R script. The entire process can also be tied together as one program to be called on the CGC platform, and this is a benefit of the platform generally. Additionally, the files given to the KNIFE have to satisfy certain naming conventions, and this was handled with the R script. It should be noted that it would not require much additional work to string together the pipeline so that one could easily use the CGC web interface to run the entire pipeline on one archive file of FASTQ files of paired-end reads. In general, the API can be run on groups of 15 to 50 archive files of FASTQ files, typically all of the same cancer disease type.

Many embodiments are also directed to generation of SBT queries from MACHETE. For each sample, each scrambled junction with reads detected by KNIFE is assigned a p-value; each chimera MACHETE detects is assigned an empirical p value as previously described. Scrambled junctions reported by KNIFE and MACHETE junctions are considered potential chimeras, and the following statistics and thresholds are used to generate these values. Chimera refers to the exon-exon pair so includes both gene name and position of donor and acceptor sequence.

Some criteria to unveil a chimera may include:
1. At least 2 total reads must map to the junction.
2. The empirical p-value for a junction<0.1.
3. The product of the empirical p value, and the sum of the maximum of junctional reads aligning to each partner in the putative chimera<5, a correction for multiple testing of junctional reads aligning to highly expressed genes.
4. The number of "A" in the eight 5' most donor sequences is six or fewer because some human exons have poly-A stretches long enough that for many reads result in failures to distinguish them from polyA tails.
5. Each KNIFE junctional sequence is split into the complete donor and 12-mer in acceptor; and the complete acceptor and 12-mer in the donor; if either sequence aligns to the KNIFE linear splice junction database using bowtie2 default parameters, the junction is classified as Bad, analogous to MACHETE's BadFJ and will not be reported as a chimera.

Once the criteria of chimeric junctions are described, the 20 nt flanking the chimeric junction of all chimeras can be retrieved and output as a fasta sequence. Each 20 nt, which is completely contained in an exon and represents the exonic boundary of the chimera, is mapped to the human genome hg19 build using bowtie2 with default parameters. The SBT query is then run using these sequences as described:
1. The summed mapping quality from the donor and acceptor sequence must exceed 45.
2. The donor and acceptor sequence must be separated by a radius>10 KB or be on opposite strands or different chromosomes; if the donor and acceptor are from the same gene, there must be greater than 100 reads mapping to the junction. Recall mapping qual: $-10 \log 10 \Pr\{$mapping position is wrong$\}$ as described in the bowtie2 manual.
3. The upper approximate 95% confidence interval for the fraction of anomalies compared to total number of reads must not exceed 0.25. Total anomalies are reported per junction by the KNIFE and are summed across all categories of anomalies for junctions reported by MACHETE. Specifically, shrinkage is applied with epsilon=0.01, to estimate p-hat, the fraction of anomalies (p-hat:=epsilon+(anomaly reads/(anomalies+non-anomaly reads)); The standard deviation of p-hat is estimated with the normal approximation and two standard deviations more than p-hat must be <0.25.

Chimeras passing the above threshold can be used as query sequences as input into the SBT for all cancers for which the SBT was built. Chimeras are reported by sMACHETE if both:
1. The SBT detects the chimera in at least one query (i.e. the SBT must detect the chimera).
2. The chimera must be detected in a sample where MACHETE and SBTs were both run.

In addition to these two reporting criteria, in order to be reported on a pan-cancer list, the empirical frequency of the chimera (e.g. across all 10 SBTs that were built) is less than or equal to the upper (1-0.0001) exact binomial confidence interval for the estimate of the pan-cancer detection rate, given by x/N, where x is the number of samples where the chimera is detected, and N is the total number of samples in the MACHETE discovery set summed over all diseases.

Likewise, in addition to the above two reporting criteria, to be reported in a list for just one of the cancers for which a SBT was built, the chimera is if the empirical frequency of the chimera for that given disease type as found by the SBT is less than or equal to the upper (1-0.0001) exact binomial confidence interval for the estimate of the within-cancer detection rate, given by x/N, where x is the number of samples where the chimera is detected in the SBT for the particular disease, and where N is the number of samples in the MACHETE discovery set within a disease.

Multiple embodiments are also directed to the ability of sMACHETE to detect false-negative rates. Two classes of false negatives (FN) are detected by sMACHETE (1) FN by the sequence bloom tree, in the sense that a junction is detectable by KNIFE and MACHETE but fails to be detected by the SBT. This situation can arise when there are not sufficiently many k-mers found by the SBT (here, we require 80% of the 20mers in the 40 nt sequence composed of the 20 flanking sequences on each side of the junction to be detected); It is possible for KNIFE and or MACHETE to detect junctions that, for example, have 2 total reads but both reads overlap the junction by, for example, 15 nt. In this case, the SBT will not detect the junction, although KNIFE or MACHETE will. For example, the FN rate can be defined to be NaN. (2) FN junctions detected in samples by the SBT that are not detected by MACHETE or KNIFE. When the number of samples with a junction detected by the SBT is greater than the number of samples with a junction detected by the MACHETE or KNIFE, the false negative rate is defined as the number of samples containing a detected junction by the SBT divided by the number of samples containing a detected junction by the SBT.

Figure 21:
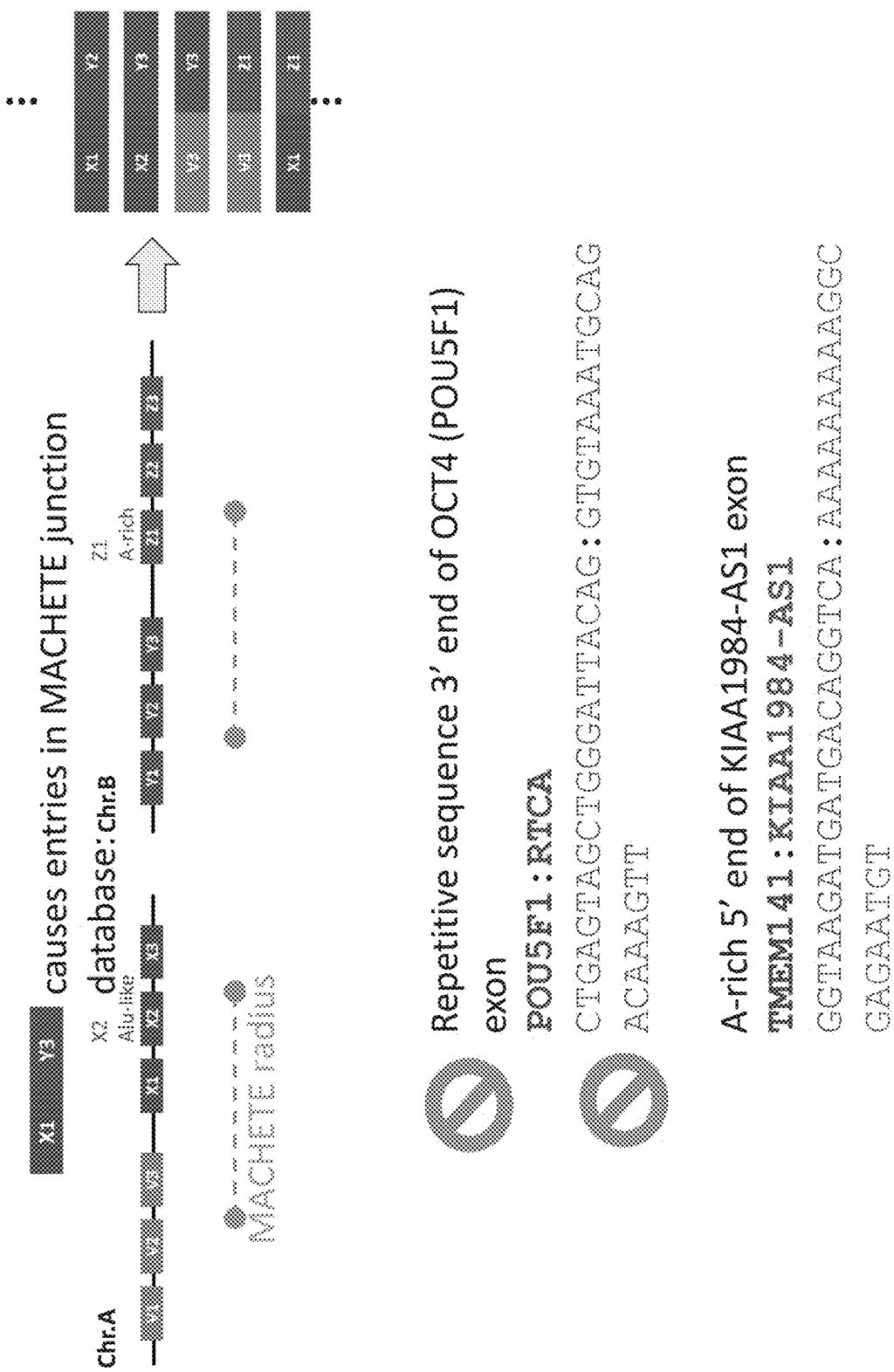
FIG. 21 illustrates examples of sequence read processing in accordance with various embodiments of the invention.

To test the ability of sMACHETE, MACHETE was run on 22 cancers in the TCGA using a discovery set consisting of a large fraction of AML (n=65, 37% of individuals represented in the TCGA database), serous ovarian (n=82, 19% of individuals with primary tumors in the database), pancreatic (n=101, 57% of individuals with primary tumors) and glioblastoma (n=92, 59% of individuals with primary tumors) and a small fraction of the other cancers (399 in 18 cancers, 6% of individuals with primary tumors for these cancers profiled by the TCGA). The remaining samples were designated and used as "testing" data (FIG. 21). As negative controls, Illumina Human Bodymap datasets were analyzed because as described by the TCGA consortium, samples classified as "Solid Tissue Normal" in the TCGA datasets are not consistently molecularly normal. In the discovery step, a subset of tumors was deeply sampled. These subset of tumors included tumors where early detection or new drug targets could have great impact (serous ovarian carcinoma, glioblastoma multiforme and pancreatic adenocarcinoma) as well as AML, which was used because its cytogenetics have been extensively studied.

Bloom filters for RNA-Seq sequencing reads were constructed from each primary tumor for the Illumina Body Map data and ten cancers defined by TCGA, which include acute myeloid leukemia (AML), breast invasive carcinoma (BRCA), cervical squamous cell carcinoma and endocervical adenocarcinoma (CESC), colon adenocarcinoma (COAD), glioblastoma multiforme (GBM), lung adenocarcinoma (LUAD), ovarian serous cystadenocarcinoma (OV), pancreatic adenocarcinoma (PAAD), prostate adenocarcinoma (PRAD), and sarcoma (SARC). The bloom filters were constructed using the same hashfile, ensuring that the filters could be combined as desired by a user. A separate SBT for each disease type was also constructed. The SBT with all chimeras nominated in the discovery step that passed a statistical threshold were queried.

Using the discovery set, a list of chimeras passing MACHETE's statistical bar were generated (FIG. 20), including those chimeras nominated by running MACHETE on negative controls from the Body Map. Then, all datasets for any chimera found in any discovery set were queried. The incidence of each chimera in each sample type (each TCGA disease or Body Map) was estimated by SBTs. Next, standard binomial confidence intervals were used to test for consistency of the rate fusions that were present in the samples used in MACHETE's discovery step and the rate they were found in the SBT. Chimeric sequences that were more prevalent across the entire dataset than statistically compatible with predicted prevalence from the discovery set were excluded from the final list of fusions (see FIG. 20).

Establishing fusion rate consistency is an important aspect. Given an exon-exon junction query sequence that could be generated by sequencing errors convolved with gene homology or ligation artifacts, SBTs will not consider the alignment profile of all reads aligning to this junction as MACHETE does, (e.g. reads with errors or evidence of other artifacts because reads with mismatches to the query sequence are by definition censored by the SBT). As a result, the SBT, like other processes, can have a high false positive rate due to: (a) false positives intrinsic to the SBT query; (b) false positive identification of putative chimeras due to events such as depicted in FIG. 11, even in the presence of a null false positive rate by the SBT itself.

False positive chimeras depicted in FIG. 20 can arise as follows: if a single artifact (e.g. a ligation artifact between two highly expressed genes) in a single sample passes MACHETE's statistical threshold in the discovery step, this artifact will be included as a query sequence. The SBT could detect it a high frequency because the statistical models employed by MACHETE are not used by the SBT. Testing for the consistency of the rate of each sequence being detected in the discovery with its prevalence as estimated by sequence bloom trees controls for the multiple testing bias (FIG. 20).

A list of chimeras unveiled is listed in Table 1. This list contains chimeras having 99% confidence of existence in the sample from which the RNA-seq data was derived. Found within the table is the names of the 5'- and 3'-gene, the number of samples in which the chimera exists within, and the junction locus data, in accordance with the UCSC hg19 genome assembly.

sMACHETE has a Lower False Positive Rate than the Best Published Methods

A great weakness in current chimera detection methods is their high rate of false positives, evidenced by reporting chimeras in simulated data that lacks them, as well as normal tissue samples. While local structural copy number variation in the human genome, such as segmental duplication, is a known source of genetic variation expression of chimeric genes in normal samples is considered to be a rare event and experimental validation rates are very low unless the chimeras are explained by transcriptional read-through. Moreover, when validated, these events tend to be somatic events present in only a fraction of cells, and so chimeric transcripts identified in bulk-derived RNA-seq datasets are expected to be both rare and private. Normal samples thus serve an excellent empirical test of an algorithm's false positive rate, as has been appreciated in the literature (Carrara et al., *BMC Bioinformatics*, 2013, the disclosure of which is incorporated herein by reference in its entirety).

The false positive rate of sMACHETE discovery pipeline was quantified by two methods (see FIGS. 22 & 23): (a) testing whether any chimeras found in TCGA tumors were also detected in the Illumina Body Map dataset (Illumina, 2011); (b) testing whether sMACHETE nominated any chimeras from the Illumina Body Map dataset. Because various reports suggest that the best performing method is a meta-caller, ChimerSeq, that integrates several different algorithms and produces what is considered the currently most reliable list of fusions present in TCGA data, it was tested whether any chimeras detected by sMACHETE and ChimerSeq in the TCGA discovery set were also detected in the Illumina body map (Lee et al., *Nucleic Acids Research*, 45:D784-89, 2016, the disclosure of which is incorporated herein by reference in its entirety).

sMACHETE's false positive rate by this method was zero: none of the chimeras that sMACHETE identified in primary tumors in the discovery set were found in the Illumina Body Map dataset. To compare sMACHETE's performance to the state-of-the-art chimera callers the published results of ChimerSeq was used, restricted to the sMACHETE discovery set, and used the SBT to query the Body Map data for these sequences. In contrast to sMACHETE, nine distinct chimeras found by ChimerSeq were also detected in the Body Map data, including several interchromosomal and present in all samples (FIG. 22), strongly suggestive of being false-positives. This establishes a significantly higher false positive rate for ChimerSeq compared to sMACHETE. Other algorithms have even higher false positive rates as reported by third parties (Carrara et al., 2013, cited supra). MACHETE's false positive rate using method (b) was also nonzero.

The number of chimeras sMACHETE detected in the Body Map was quantified as the discovery set. Seven total chimeras, and each identified chimera was found in exactly one sample was quantified. None of the chimeras identified by sMACHETE in the Body Map data were detected in any TCGA sample. In addition, all chimeras were intrachromosomal within 1 MB. This suggests that sMACHETEs discovery of chimeras in the Body Map could be (a) circRNA; (b) bona fide private somatic variants; or (c) that control of false positives by KNIFE (which is responsible for calling chimeras<=1 MB is not as strong as MACHETE's. Library-specific artifacts would be unlikely to be biased towards intra-chromosomal chimeras. Regardless of (a-c), sMA- CHETE achieves a lower FP rate than reported in the literature previously, including by ChimerSeq (Lee et al., 2016, cited supra), and would have a null FP rate if a minimum radius of 1 MB were imposed.

Figure 22:
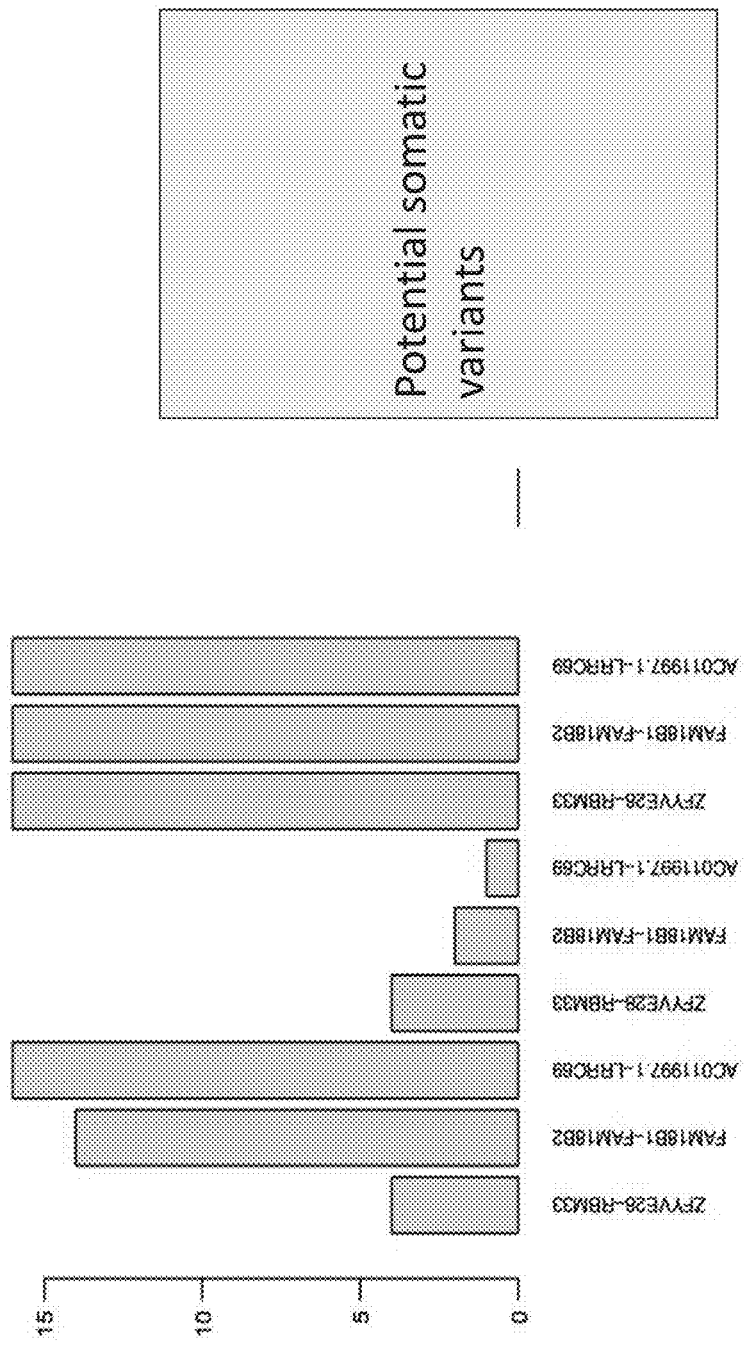
FIG. 22 illustrates a graph detailing chimeric sequence sensitivity and accuracy of various methodologies generated in accordance with several embodiments of the invention.

As a final statistical assessment of sMACHETE's false positives, tumor data from the TCGA RNA-seq corpus was compared with the estimated frequency of each chimera detected by sMACHETE in the discovery set to its estimated frequency in the test set. Recall that MACHETE, the chimera discovery tool detailed above, was never run on the test set which is an independent dataset, and thus any chimera detected in the test set is hypothesis-driven, similar in spirit, although different than a GWAS replication set. The vast majority of chimeras had consistent frequencies in the discovery and testing set, both across all cancers (FIG. 16) and in each cancer in isolation. This suggests that sMACHETE controls the false positive rate in the sense that few artifacts pass through statistical filters. If not, one would expect to see a bias toward the SBT reporting higher rates of chimeras than MACHETE since the only chimeras that are censored out of the reports are those where the SBT-reported prevalence of the fusion is outside of MACHETE''s upper binomial confidence interval. No bias of higher detected chimera frequency in the discovery set exists, consistent with a low false positive rate (FIG. 22).

MACHETE's False Negative Rate can be Empirically Estimated

Because SBTs are designed to have low false negative, SBTs were used to assess MACHETE's empirical false negative rate. MACHETE's false negative rate on recurrent chimeras are estimated using results from the SBT on the discovery set: chimeras found by the SBT but not by MACHETE were considered false negatives for MACHETE, although in principle, they could also be false positives identified by the SBT. This would result in a conservative report of the false negative rate, which is reported on a per-chimera basis. Such estimates are not provided by other methods, hampering performance evaluations in clinical samples.

A subset of sequences are predicted to be detected by MACHETE but not by a SBT, chimeras with low coverage, where MACHETE could detect expression and could score these junctions highly if the reads have appropriate statistical properties. The SBT methodology requires higher junction coverage—i.e. a larger junction overlap (i.e., 19 out of 21 k-mers for a 40-base exon-exon junction) than does MACHETE, and so such chimeras could be missed by the SBT. Using this metric, MACHETE has a quantifiable and low false negative rate. As a technical point, this estimate of the false negative rate across chimeras should only be considered for recurrent chimeras as to be a true false negative for the MACHETE, the SBT detect the chimera at least twice.

sMACHETE Precisely Rediscovers Known Recurrent Gene Fusions in AML

Leukemias are examples of cancers with stereotypic translocations where gene fusions were first described. This tumor type was used as a way to assess MACHETE's in unbiased chimera detection by comparing it to results reported by a large consortium that performed next-generation sequencing analysis and cytogenetics on a large cohort of AML samples (Ley, *N. Engl. J. Med.*, 368:2059-74, 2013; Papaemmanuil et al., *N. Engl. J. Med.*, 374:2202-21, 2016; the disclosures of which are incorporated herein by reference in its entirety).

Sixty-five individuals were used in the sMACHETE discovery set. All recurrent chimeras identified in these samples are previously reported gold standard gene fusions in the literature with the exception of a pan-cancer chimera, CPSF6-CHMP1A which were validated by PCR. sMACHETE detected common gene fusions in AML including CBFB-MYH11, KATSA-CREBBP, a variety of RUNX1 and MLL fusions, and the classical BCR-ABL1 fusion characteristic of Chronic Myelogenous Leukemia but which has also been reported in AML (Bacher et al., *Br. J. Haematol.*, 152:713-20, 2011, the disclosure of which is incorporated herein by reference in its entirety). PML-RARA and its reciprocal transcript were also detected. sMACHETE's calls for AML chimeras are results from a completely unbiased search, and no ad hoc filters were applied.

Figure 23:
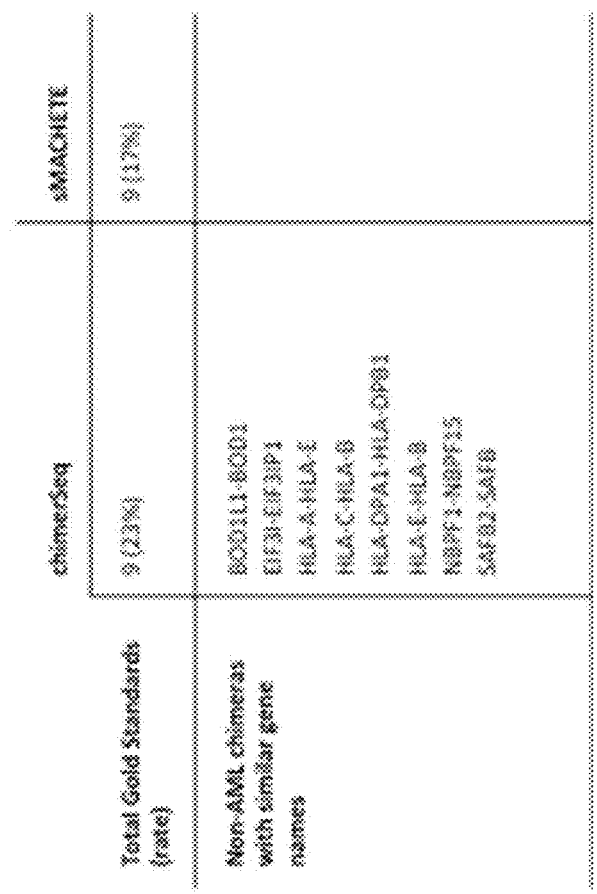
FIG. 23 illustrates a graph detailing chimeric sequence sensitivity and accuracy of various methodologies generated in accordance with a number of embodiments of the invention.

The majority of these chimeras are AML-specific. sMACHETE recovered these chimeras more precisely than with the meta-caller ChimerDBSeq (Lee et al., 2016, cited supra) as compared to an independent survey of AML fusions as measured by the fraction of known fusions in AML recovered compared to total fusions reported (FIG. 23). Seventeen chimeras were identified by both sMACHETE and ChimerSeq; eight of which are classical AML fusions. Twelve chimeras are identified only sMACHETE and thirty-five by only ChimerSeq. sMACHETE and ChimerSeq identify one unique classical AML fusion missed by the other methods. ChimerSeq alone detects RUNX1-RUNX1T1; this fusion is detected by MACHETE with two counts. This chimera failed to be detected by SBT presumably because of the low numbers of counts at the junction resulting in a failure of detection by sMACHETE. This supports the prediction MACHETE detection is more sensitive than sMACHETE. MACHETE did discover RUNX1-RUNX1T1 but it did not meet sMACHETE's statistical bar and therefore it was not reported, however, it does detect and report the reciprocal chimera, RUNX1T1-RUNX1.

Finally, excepting genes involved in classical leukemia fusions which were given similar names because of their joint participation in fusions, putative fusions between homologous genes are generally considered false positives. FIG. 23 shows sMACHETE's improved performance in this realm; it is agnostic to gene names, but finds 0 non-AML fusions with similar gene names, whereas ChimerSeq reports 8 of the 52 total reported (15%; and a higher fraction than 15% when known AML chimeras are excluded from the 52 total reported).

sMACHETE Improves Precise Pan-Cancer Re-Identification of Known Gene Fusions

In addition to testing sMACHETE's chimera discovery in the cytogenetically simple leukemias, its precision was tested in a variety of solid tumors which have more complex cytogenetics. A priori, this complexity could result in either more false positives or prevent sensitive detection of chimeras. One would expect a relationship between total number of chimeras detected and orthogonal measures of genome stability, such as rates of DNA damage checkpoint mutation (e.g. TP53 mutation), chromothripsis or other metrics. For example, the fraction of AML containing gene fusions is well studied, and cytogenetic and analyses have established the increased prevalence of fusions in sarcomas compared to other cancers.

Figure 24:
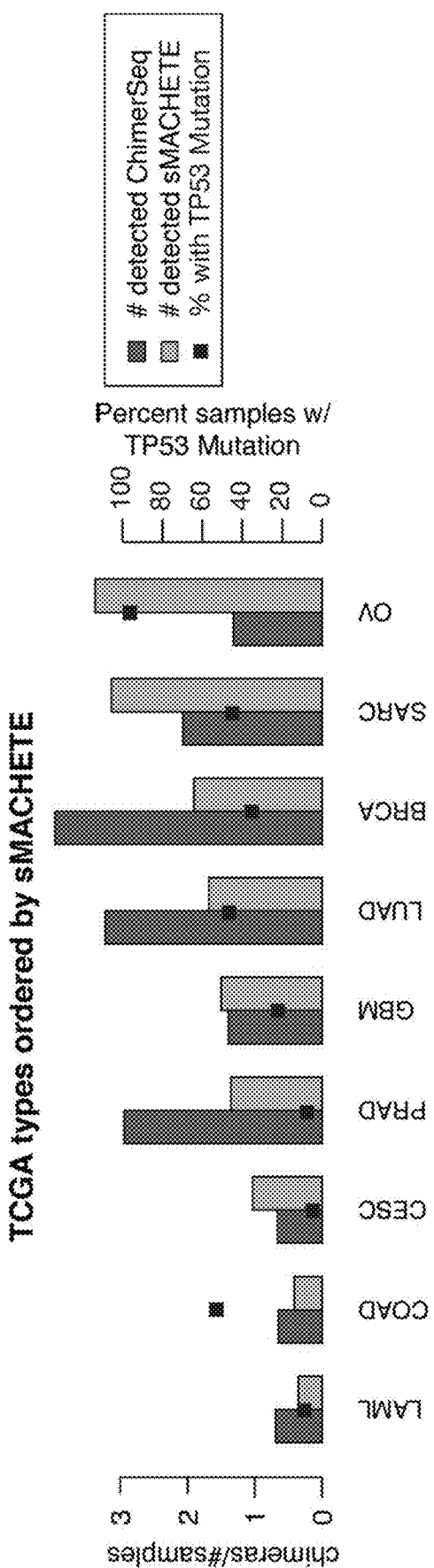
FIG. 24 illustrates a graph detailing chimeric sequence sensitivity and accuracy of various methodologies generated in accordance with certain embodiments of the invention.

As described above, the largest numbers of samples in the discovery set from prostate adenocarcinoma, ovarian serous cystadenocarcinoma, pancreatic adenocarcinoma and glioblastoma multiforme were used, but smaller numbers from other disease types we also analyzed (FIG. 24). This pan-cancer analysis is partly a test of sMACHETE's unbiased recovery of the known prevalence of chimeras in cancers as a function of the degree of their DNA rearrangement.

Specifically, sMACHETE's prediction of chimera prevalence matches TP53 mutation prevalence more dependably than ChimerSeq (FIG. 24). As expected, OV, which has the highest known TP53 mutation rate, also has the highest chimera prevalence detected by sMACHETE, though not by ChimerSeq.

sMACHETE detects chimeras at a rate more consistent with these orthogonal measures than does ChimerSeq (FIG. 24). sMACHETE predicts chimeras in AML at an order of magnitude lower frequency compared to OV and SARC, two cancers with highly rearranged genomes and highly prevalent TP53 mutations. ChimerSeq predicts much closer frequencies between these tumor types, and unexpectedly few chimeras in OV, and reports that the rate of chimeras detected in tumors sampled in COAD and CESC is less than that in AML, which is unexpected.

The ability to precisely detect specific gold standard chimeras in tumors by sMACHETE was also tested. To do this, first, a discovery set was specifically designed in prostate cancer, unlike sampling in all other tumor types, which was essentially unbiased and arbitrary, to include 15 prostate cancers that were positive for TMPRSS2-ERG. The discovery set consisted of 15 of the 23 samples reported in (Sadis et al., 2013 (https://www.thermofisher.com/content/dam/LifeTech/Documents/PDFs/Oncomine/2013AACR_genefusions.pdf), the disclosure of which is incorporated herein by reference in its entirety). sMACHETE detected eight splice variants of TMPRSS2-ERG demonstrating the sensitivity of including detection of isoform-specific expression of fusions.

sMACHETE also identifies the most common gene fusion in GBM, EGR fusions, the LANCL2-SEPT14 and FGFR3-TACC3 fusions with highest prevalence in GBM and cervical cancer as well as other less common drivers such as ETV6-NTRK3 in colorectal adenocarcinoma (COAD). As an illustration of sMACHETE's improved precision, while sMACHETE has fewer false positives than all other tested methods, including ChimerSeq, which missed the recurrent LANCL2-SEPT14 in GBM and the validated driving fusion ETV6-NTRK3 in COAD despite having a higher false positive rate than sMACHETE.

As expected, chimeras reported by sMACHETE in all cancers are highly depleted of circular RNA, partly because of biochemical approaches in library prep. A criteria we imposed that intragenic chimeras (intragenic exon rearrangements) had to be expressed at high levels to pass into sMACHETE's final list of chimeras. This suggests that the vast majority of chimeras are linear isoforms. However, one would presume that some chimeras identified by MACHETE and other methods, particularly those involving neighboring genes, are circular.

Chimeras Identified by sMACHETE are Enriched in COSMIC and Kinase Genes

Figure 25:
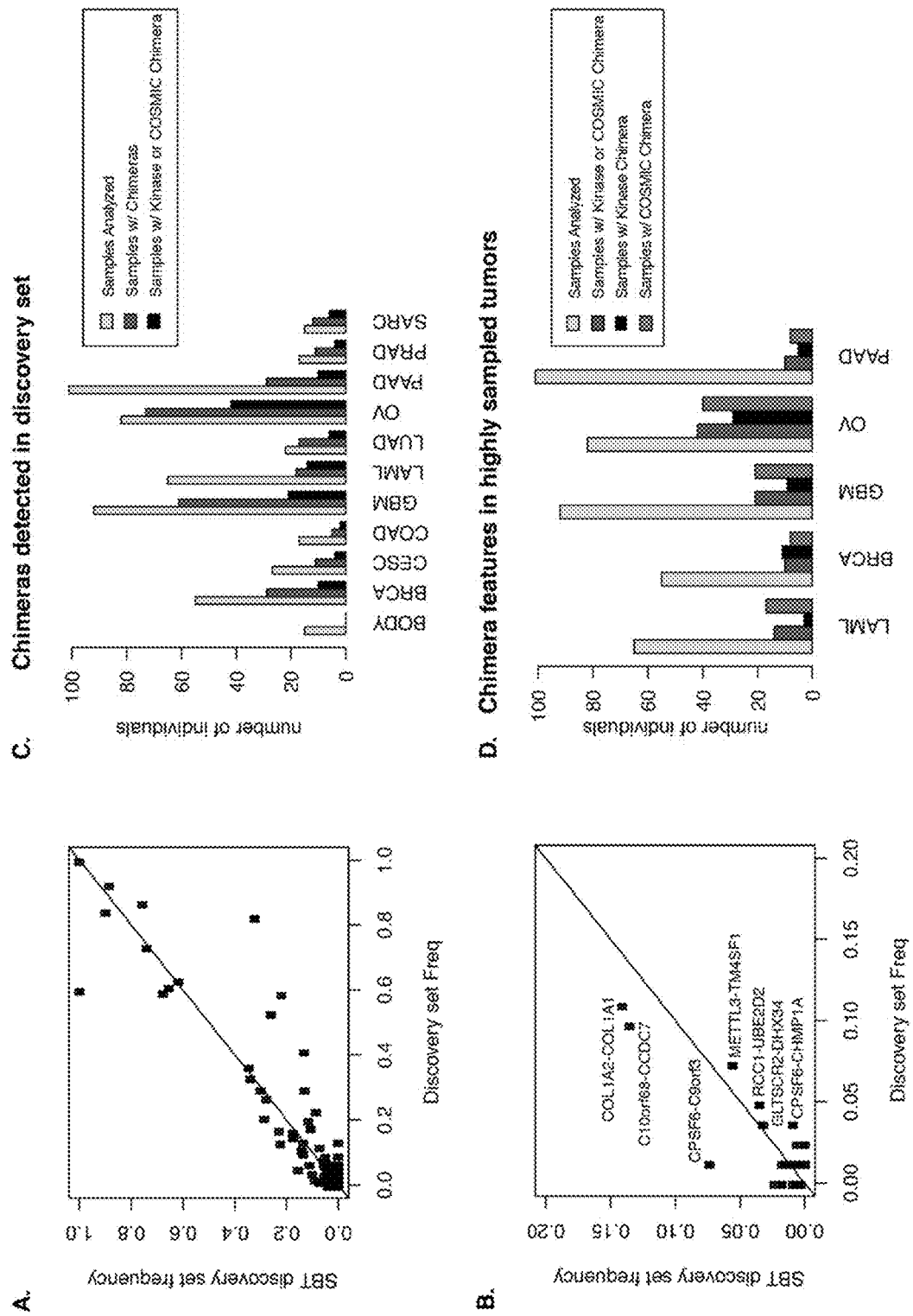
FIG. 25 illustrates graphs detailing chimeric sequence sensitivity and accuracy of various methodologies generated in accordance with several embodiments of the invention.

Because the only ontologies used by sMACHETE are exon sequences, one can use functional annotations of genes involved in chimeras as an independent test to see whether sMACHETE is identifying a biological signal. If it is, one would expect an enrichment of genes in the chimeras it identifies involved in known cancer pathways. To test this, for each cancer type, the total number of distinct chimeras sMACHETE identifies was computed, as well whether their annotation includes the word "kinase" or present in the Catalogue of Somatic Mutations in Cancer (COSMIC) database. In most cancer types profiled by sMACHETE, the fraction of chimeras identified and annotated as either COSMIC or kinase exceeds 20%, a rate much greater than expected by chance given the number of such genes with an annotation including the word "kinase" in the genome (FIG. 25).

The largest enrichment of COSMIC genes or those whose annotation includes the word "kinase" is in AML which matches expectations because AML fusions are very well studied, known to drive some leukemias and therefore annotated as COSMIC genes. No enrichment was found for exclusivity in "kinase" or COSMIC genes among chimeras detected in each tumor conditional on chimeras being drawn at random from sMACHETE's pan-tumor list, perhaps not surprising given the enrichment for genes with annotations including "kinase" and COSMIC genes in the list of detected chimeras per tumor.

Ovarian Cancers are Enriched in Chimeras Including Kinase and COSMIC Genes

The most common genetic lesion in ovarian cancer is the TP53 mutation, present in >99% of cases (Cancer Genome Atlas Research Network, 2011). However, apart from this event, few common recurrent driving lesions are known. This suggests that RNA chimeras could be responsible for driving some fraction of these cancers.

sMACHETE reports 89% of all ovarian cancers in its discovery set to have a gene chimera, the highest rate of any disease we profiled. Slightly over 50% of tumors contain a chimera involving a kinase or COSMIC gene, again a higher frequency than any other profiled disease. Prevalent recurrent chimeras were not detected, with the exception of those that could be explained by circRNA, although recurrent chimeras involving genes on different chromosomes, unlikely to be circRNA, were detected: 3.8% of tumors were estimated to have the chimera RCC1-UBE2D2 (RCC1 is a regulator of chromosome condensation, UBE2D2 a ubiquitin conjugating enzyme), which is predicted to be specific to ovarian tumors, and 5.9% the chimera METTL3-TM4SF1 (METTL3 is a methyltransferase like protein and TM4SF1 a transmembrane protein of unknown function), also specific to ovarian cancer. The discovery and testing set frequencies for these chimeras were very similar, and both chimeras in both discovery and testing sets were specific to ovarian cancer, suggesting a potential driving role.

Together, these data suggest that the rate chimeras observed in ovarian cancer is higher than previously appreciated. sMACHETE's unbiased estimation of chimera prevalence in other tumors is consistent with pan-cancer estimates by orthogonal means. Along with sMACHETE's specificity on normal controls, these results support the idea that chimeras, perhaps relatively rare or even unique, could be an unappreciated driver of ovarian cancers.

Rare Recurrent Pan-Cancer Gene Chimeras are a Hallmark of Solid Tumors sMACHETE's performance recovering gold standard chimeras in primary tumors as well as its low rate of false positives suggests that it has improved sensitivity to discover novel recurrent chimeras. A statistical model can be used that tests whether, conditional on the total number of gene chimeras in all tumors, a particular chimera is observed more than once. Because sMACHETE detects an order of magnitude fewer chimeras than a number of genes, the probability of a recurrent event by chance alone is very small. Under this null model, essentially no recurrent chimeras are expected to be detected.

sMACHETE predicted roughly 100 recurrent gene chimeras. Some of these chimeras are well-known, as described above. Together, the total number of recurrent chimeras that sMACHETE detected in addition to known, well-studied, driving gene fusions suggests a signature of selection. Consistent with this, large number of the recurrent chimeras, involve partners with at least partial evidence of druggability, such as kinases, chromatin remodeling complexes and other signaling molecules, such as the chimera including Strawberry Notched Homolog, SBNO2, SBNO2-SERINC2. Other recurrent chimeras were re-discovered, such as the RPS6 KB-VMP1 fusion in BRCA, but also detected for the first time in other cancer types, such as LUAD and OV.

Figure 26:
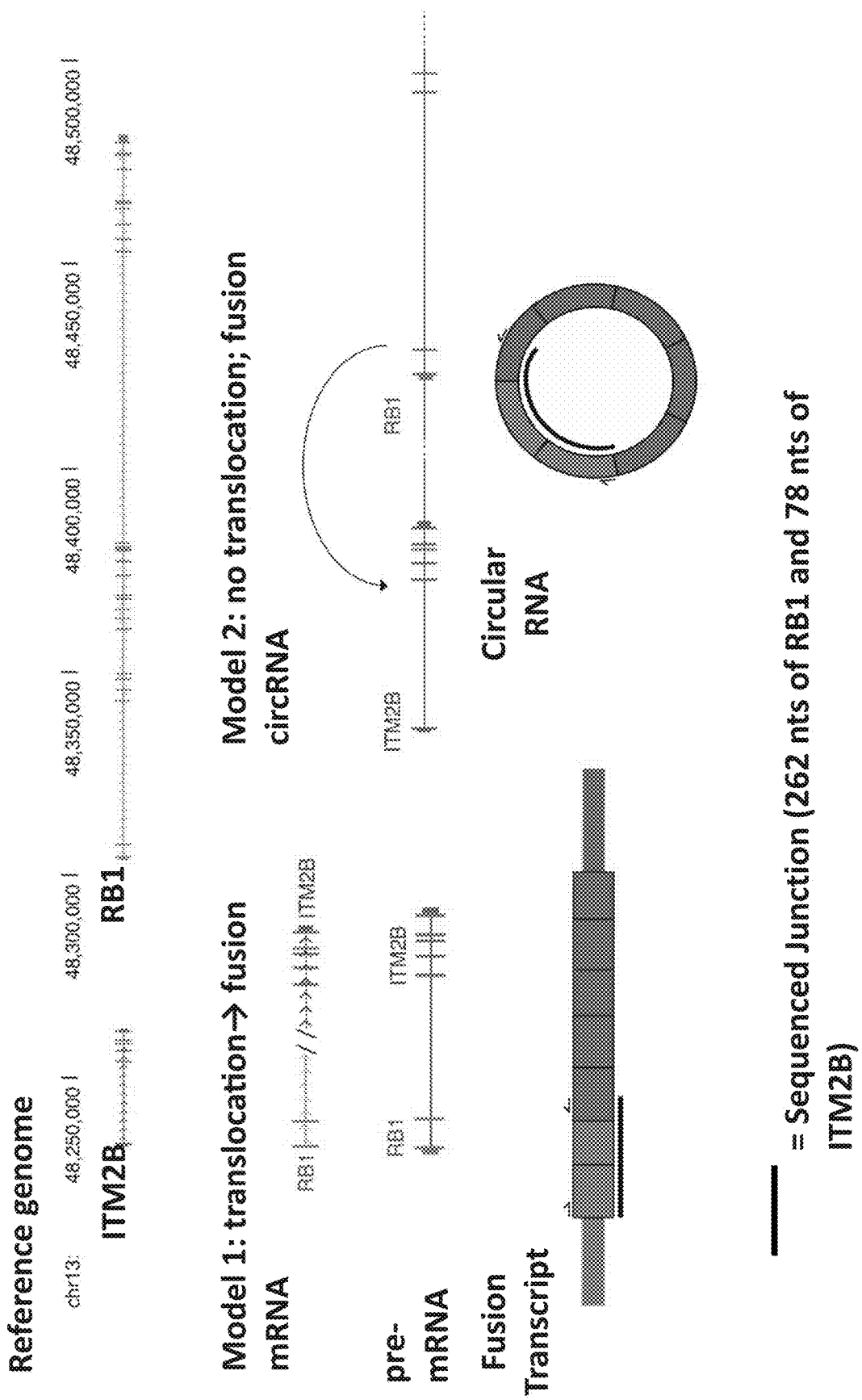
FIG. 26 illustrates an example of a chimeric sequence unveiled in accordance with various embodiments of the invention.
Figure 27:
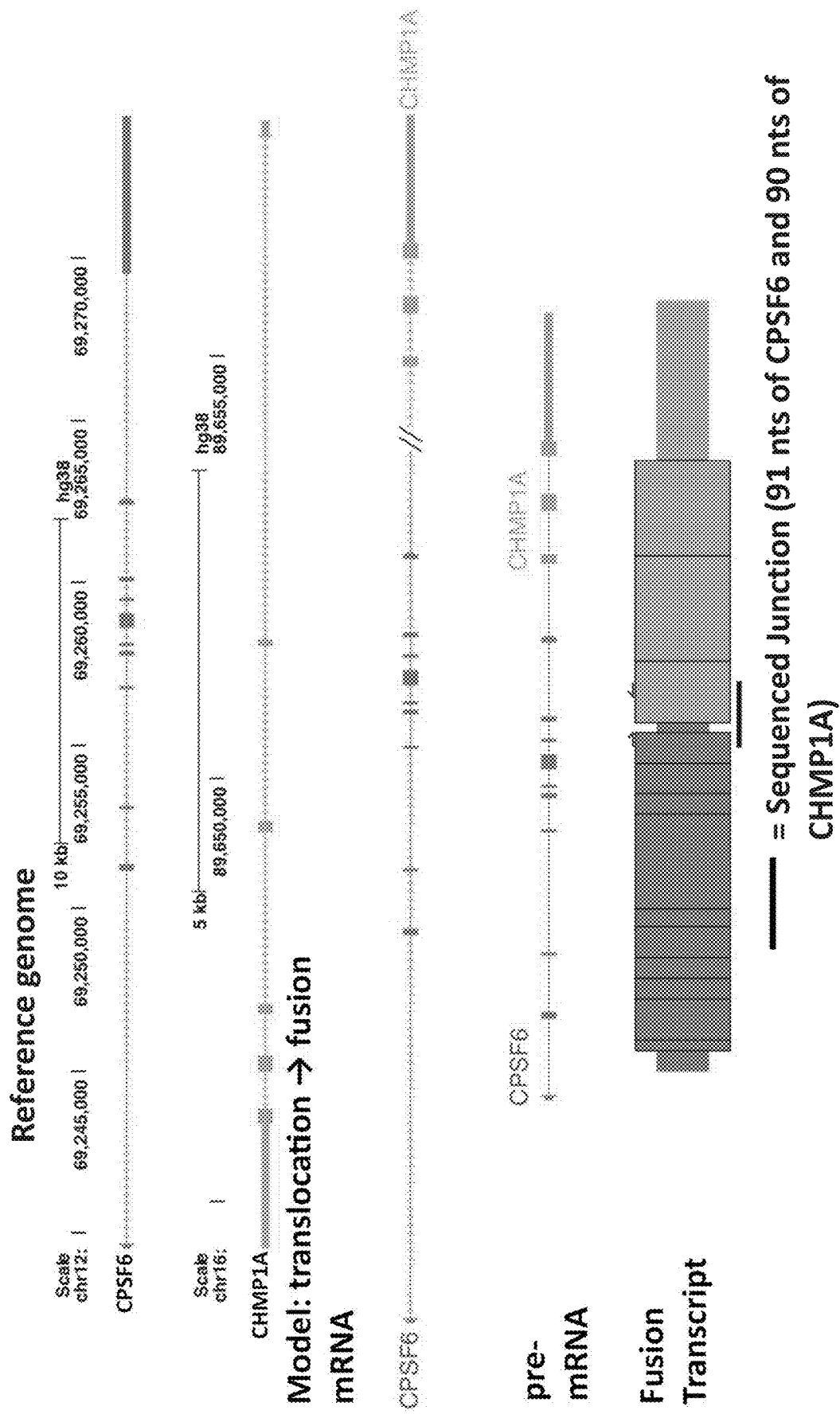
FIG. 27 illustrates an example of a chimeric sequence unveiled in accordance with various embodiments of the invention.

Using predictions from TCGA data, validation of two such chimeras was attempted, predicted to be present in a variety of tumors, CPSF6-CHMP1A and RB1-ITMB2. RT-PCR from 10 primary ovarian tumor samples was performed (labeled A-J (-E) and two cell lines, HeLa and K562 which we considered to be negative controls. Samples (C,F,G) had PCR products of the expected size for CPSF6-CHMP1A and samples (B,G,H,I, and J) had PCR products of the expected size for containing the RB1-ITM2B chimera. Neither chimera was detected in HeLa or K562 samples. Sanger sequencing of the PCR products confirmed the chimeric sequence from these predicted junction (FIG. 26). CPSF6-CHMP1A is an inter-chromosomal chimera whereas the RB1 and ITM2B are transcribed in neighboring loci, and thus the chimera could be explained by a circular RNA or a local genomic rearrangement (see FIG. 27). An attempt was not made to distinguish whether an underlying DNA change was responsible for the RB1-ITM2B chimera.

The same samples were tested using PCR for the TFG128-GPR128 chimera, which has been previously described and validated (Chase et al., *Haematologica*, 95:20-26, 2010, the disclosure of which is incorporated herein by reference in its entirety) and is also detected by sMACHETE. Consistent with the range of previous reports, sMACHETE estimates its frequency to be <1% in SARC, and 2.8% in PAAD, 1.5% in OV. PCR tests for TFG128-GPR128 in the ovarian samples were negative. The putative ovarian-specific recurrent chimeras METTL3-TM4SF1 (sMACHETE predicted frequency 5.9%) and RCC1-UBE2D2 (sMACHETE predicted frequency 3.8%) were also tested in these samples. The PCR results to detect putative chimeras were negative, which is not unexpected under simple binomial sampling models given the estimated prevalence using TCGA data.

Apart from sMACHETE's rediscovery of known recurrent gene fusions, the vast majority of sMACHETE's predicted chimeras were present in a small number of tumors. Because many chimeras were present in only one sample in the discovery set, and yet detected in multiple tumors using sMACHETE via the SBT, this suggests that the size of the discovery set may be insufficient to detect the repertoire of recurrent chimeras expressed in tumors.

Description of PCR Validation Methods on Select Chimeras Unveiled by sMACHETE

Reverse transcription of RNA was performed on Ovarian cancer samples (600 ng of each and 1 ug for neg. control HeLa and K562 total RNA) using Moloney Murine Leukemia Virus Reverse Transcriptase (M-MLV RT) enzyme (Promega) according to manufacturer's recommendations. The reverse transcription was primed with equal parts of random N6 (PAN facility, Stanford University) at 2.5 mM final concentration. cDNA reaction was diluted 1:10 and used 1 mL/10 mL PCR reaction. Validation and negative control reactions were run on a 1×TBE 1.75% Agarose gel and imaged using Alpha Innotech Alphalmager™ (San Leandro, Calif.) gel imaging system. PCR-validated fusion transcripts were further confirmed using Sanger sequencing. PCR primers used and validated PCR sequences can be found in the following paragraphs.

Primer Sequences Used for Candidate Junction CPSF6-CHMP1A:

Forward:
(Seq. ID No. 33)
AAGCAGAGAACGAGAGAGGC

Reverse:
(Seq. ID No. 34)
TGTCCATCACTGAGGAGACC

Sanger Sequencing Result for CPSF6-CHMP1A:

(Seq. ID No. 35)
CTTCTAACGATGACGATATTCGCGCTCTCGGTCACGCTCTCGGTCACGGT

CTCGGTCACGATCCCGGTGCCTCTCTCGTTCTCTGCTTAAGAGGTGACCA

AGAATATGGCCCAGGTGACCAAAGCCCTGGACAAGGCCCTGAGCACCATG

GACCTGCAGAAGGTCTCCTCAGTGATGGACA

Primer Sequences Used for Candidate Junction RB1-ITM2B:

Forward:
(Seq. ID No. 36)
ATGCCGCCCAAAACCCCCCGAAAAAC

Reverse:
(Seq. ID No. 37)
CTCCTCCTAGAATAACACCTGCA

Sanger Sequencing Result for RB1-IMT2B:

(Seq. ID No. 38)
TGCACCATACCAGGCTTCCTTCTTTGGCCACCGGTACCACATCATCTGGG

TCCAATACTCCATCCACAGATGAAACTTTCTCCCAAGTTAACCAAGCTCT

CTCTCTGACATGATCTGGTATCTTTAATTTCTGACATAATGCAGTAAAAT

CAGGTTCTTCTGTTTCTTCAAACTCAAGCCTGACGAGAGGCAGGTCCTCC

GGGCCGCTGTCCTGCTCTGGGTCCTCCTCAGGAGGGGCGGCGGCGGCGG

TGCCGGGGGTTCCGCGGCGGCAGCGGCGGCGGTGGCGGCCGTTTTTCGGG

GGGTTTTGGGCGGCA

Individual Chimera Partners Recur More Frequently than by Chance

Genes participating in multiple chimeras as 5' or 3' partners could be evidence the recurrent partners being oncogenes. The ETS family of transcription factors is a prime example of this, and recurrently participates in gene fusions across a variety of cancer types. Yet, to infer selection for a partner to be recurrent, it is essential to have a statistical model for the null distribution of number of times partners in a chimera are expected to be paired with multiple genes. For example, if many tumors are sampled, and many chimeras are reported, by chance, some genes will be present on the list of chimeras more than once. The critical question for assessing a potential biological relevance is whether representation of the 5' or 3' partner is greater than by chance.

Of the almost 1000 gene chimeras identified in the discovery set, if 5' or 3' chimera partners are drawn from all annotated genes at random, the number of distinct 5' or 3' partners present on the list of gene chimeras has a known statistical distribution because the problem matches the famous "coupon collector's problem". In the coupon collector's problem, n coupons are available, and a collector receives them at random. Probability studies have focused on how many distinct coupons the collector will have after collecting k total coupons. For the current application, gene chimeras are the coupons, and desire to test whether the number of distinct genes (coupons) nominated by sMACHETE is lower than expected by chance, indicating a non-random and perhaps selective advantage for a subset of genes to be involved in a chimera. There is also a mapping to the 'balls in boxes' problem in statistics, where k balls are thrown into n boxes and the null distribution of the number of boxes with >1 ball can be computed.

The distribution of number of genes recurrently involved in chimeras as 5' or 3' partners in sMACHETE chimeras is higher than would be expected by chance and is highly significant. Other more commonly used statistics in this context, such as how many coupons (genes) are collected (detected) multiple times (i.e. paired with multiple partners) expected after k total have been collected. Some such coupons (genes) are detected at much higher frequencies than expected by chance: genes with the highest diversity of 5' and 3' partners include known oncogenes previously not reported to participate in chimeras, such as MDM2, as well as novel oncogenes in the YEATS family. The most promiscuous chimera partners include VMP1, which is recurrently fused as a 3' partner with four 5' partners. RALA and CHMP1A each have three distinct 5' partners. CPSF6 has six distinct 3' partners. It should be noted, as more types neoplastic samples are analyzed, more 5' and 3' partners are likely to be discovered.

Together, the finding that 'coupons,' i.e. genes involved in chimeras, are accumulated at a slower than random rate is consistent with a model where a large number of genes are oncogenic as 3' or 5' partners in RNA chimeras. Under this model, if N such genes exist, large numbers of oncogenic chimeras also exist—order gN where g is the number of human genes. Until sampling of tumors approaches O(gN), one would not expect to observe any particular chimera in multiple tumors. Therefore, the use of recurrence as a proxy for driving RNA chimeras would not be useful.

TABLE 1

Chimeras Unveiled by sMACHETE

| 5'-Gene (gene1) | 3'-Gene (gene2) | Number of Samples Found to Have Chimera | strand 1 | strand 2 | chr1 | chr2 | pos1 | pos2 |
|---|---|---|---|---|---|---|---|---|
| TMPRSS2 | ERG | 171 | − | − | chr21 | chr21 | 42880008 | 39817544 |
| TMPRSS2 | ERG | 171 | − | − | chr21 | chr21 | 42880008 | 39817544 |
| C10orf68 | CCDC7 | 83 | + | + | chr10 | chr10 | 32873232 | 32832228 |
| C10orf68 | CCDC7 | 83 | + | + | chr10 | chr10 | 32873232 | 32832228 |
| C10orf68 | CCDC7 | 83 | + | + | chr10 | chr10 | 32873232 | 32832228 |
| C10orf68 | CCDC7 | 83 | + | + | chr10 | chr10 | 32873232 | 32832228 |
| C10orf68 | CCDC7 | 83 | + | + | chr10 | chr10 | 32873232 | 32832228 |
| C10orf68 | CCDC7 | 83 | + | + | chr10 | chr10 | 32873232 | 32832228 |
| TMPRSS2 | ERG | 70 | − | − | chr21 | chr21 | 42880008 | 39795483 |
| TMPRSS2 | ERG | 67 | − | − | chr21 | chr21 | 42870046 | 39817544 |
| TFG | GPR128 | 62 | + | + | chr3 | chr3 | 100438902 | 100348442 |
| TFG | GPR128 | 62 | + | + | chr3 | chr3 | 100438902 | 100348442 |
| TFG | GPR128 | 62 | + | + | chr3 | chr3 | 100438902 | 100348442 |
| TFG | GPR128 | 62 | + | + | chr3 | chr3 | 100438902 | 100348442 |
| TFG | GPR128 | 62 | + | + | chr3 | chr3 | 100438902 | 100348442 |
| TFG | GPR128 | 62 | + | + | chr3 | chr3 | 100438902 | 100348442 |
| TFG | GPR128 | 62 | + | + | chr3 | chr3 | 100438902 | 100348442 |
| TFG | GPR128 | 62 | + | + | chr3 | chr3 | 100438902 | 100348442 |
| TFG | GPR128 | 62 | + | + | chr3 | chr3 | 100438902 | 100348442 |
| TFG | GPR128 | 62 | + | + | chr3 | chr3 | 100438902 | 100348442 |
| CPSF6 | CHMP1A | 40 | + | − | chr12 | chr16 | 69656342 | 89713739 |
| CPSF6 | CHMP1A | 40 | + | − | chr12 | chr16 | 69656342 | 89713739 |
| CPSF6 | CHMP1A | 40 | + | − | chr12 | chr16 | 69656342 | 89713739 |
| CPSF6 | CHMP1A | 40 | + | − | chr12 | chr16 | 69656342 | 89713739 |
| CPSF6 | CHMP1A | 40 | + | − | chr12 | chr16 | 69656342 | 89713739 |
| CPSF6 | CHMP1A | 40 | + | − | chr12 | chr16 | 69656342 | 89713739 |
| CPSF6 | CHMP1A | 40 | + | − | chr12 | chr16 | 69656342 | 89713739 |
| CPSF6 | CHMP1A | 40 | + | − | chr12 | chr16 | 69656342 | 89713739 |
| FGFR3 | TACC3 | 40 | + | + | chr4 | chr4 | 1808661 | 1741429 |
| FGFR3 | TACC3 | 40 | + | + | chr4 | chr4 | 1808661 | 1741429 |
| CHD2 | LOC100507217 | 35 | + | + | chr15 | chr15 | 93444529 | 93428745 |
| CHD2 | LOC100507217 | 35 | + | + | chr15 | chr15 | 93444529 | 93428745 |
| CHD2 | LOC100507217 | 35 | + | + | chr15 | chr15 | 93444529 | 93428745 |
| CHD2 | LOC100507217 | 35 | + | + | chr15 | chr15 | 93444529 | 93428745 |
| CHD2 | LOC100507217 | 35 | + | + | chr15 | chr15 | 93444529 | 93428745 |
| CHD2 | LOC100507217 | 35 | + | + | chr15 | chr15 | 93444529 | 93428745 |
| CHD2 | LOC100507217 | 35 | + | + | chr15 | chr15 | 93444529 | 93428745 |
| COL1A2 | COL1A1 | 26 | + | − | chr7 | chr17 | 94035615 | 48266371 |
| COL1A2 | COL1A1 | 26 | + | − | chr7 | chr17 | 94035615 | 48266371 |
| COL1A2 | COL1A1 | 26 | + | − | chr7 | chr17 | 94035615 | 48266371 |
| COL1A2 | COL1A1 | 26 | + | − | chr7 | chr17 | 94035615 | 48266371 |
| METTL3 | TM4SF1 | 25 | − | − | chr14 | chr3 | 21971807 | 149093556 |

TABLE 1-continued

Chimeras Unveiled by sMACHETE

| 5'-Gene (gene1) | 3'-Gene (gene2) | Number of Samples Found to Have Chimera | strand 1 | strand 2 | chr1 | chr2 | pos1 | pos2 |
|---|---|---|---|---|---|---|---|---|
| GATS | PILRB | 20 | − | + | chr7 | chr7 | 99820220 | 99952766 |
| GATS | PILRB | 20 | − | + | chr7 | chr7 | 99820220 | 99952766 |
| GATS | PILRB | 20 | − | + | chr7 | chr7 | 99820220 | 99952766 |
| GATS | PILRB | 20 | − | + | chr7 | chr7 | 99820220 | 99952766 |
| GATS | PILRB | 20 | − | + | chr7 | chr7 | 99820220 | 99952766 |
| GATS | PILRB | 20 | − | + | chr7 | chr7 | 99820220 | 99952766 |
| GATS | PILRB | 20 | − | + | chr7 | chr7 | 99820220 | 99952766 |
| RB1 | ITM2B | 20 | + | + | chr13 | chr13 | 48881542 | 48827944 |
| RB1 | ITM2B | 20 | + | + | chr13 | chr13 | 48881542 | 48827944 |
| RB1 | ITM2B | 20 | + | + | chr13 | chr13 | 48881542 | 48827944 |
| RB1 | ITM2B | 20 | + | + | chr13 | chr13 | 48881542 | 48827944 |
| RB1 | ITM2B | 20 | + | + | chr13 | chr13 | 48881542 | 48827944 |
| RB1 | ITM2B | 20 | + | + | chr13 | chr13 | 48881542 | 48827944 |
| RB1 | ITM2B | 20 | + | + | chr13 | chr13 | 48881542 | 48827944 |
| TMPRSS2 | ERG | 19 | − | − | chr21 | chr21 | 42880008 | 39956869 |
| CHD2 | CHMP1A | 17 | + | − | chr15 | chr16 | 93444529 | 89713739 |
| CHD2 | CHMP1A | 17 | + | − | chr15 | chr16 | 93444529 | 89713739 |
| CHD2 | CHMP1A | 17 | + | − | chr15 | chr16 | 93444529 | 89713739 |
| CHD2 | CHMP1A | 17 | + | − | chr15 | chr16 | 93444529 | 89713739 |
| CHD2 | CHMP1A | 17 | + | − | chr15 | chr16 | 93444529 | 89713739 |
| CHD2 | CHMP1A | 17 | + | − | chr15 | chr16 | 93444529 | 89713739 |
| CHD2 | CHMP1A | 17 | + | − | chr15 | chr16 | 93444529 | 89713739 |
| RCC1 | UBE2D2 | 16 | + | + | chr1 | chr5 | 28832596 | 138979957 |
| LANCL2 | 14-Sep | 13 | + | − | chr7 | chr7 | 55479782 | 55886916 |
| CBFB | MYH11 | 10 | + | − | chr16 | chr16 | 67116211 | 15814908 |
| FBRSL1 | NOC4L | 10 | + | + | chr12 | chr12 | 133067447 | 132635526 |
| FBRSL1 | NOC4L | 10 | + | + | chr12 | chr12 | 133067447 | 132635526 |
| FBRSL1 | NOC4L | 10 | + | + | chr12 | chr12 | 133067447 | 132635526 |
| FBRSL1 | NOC4L | 10 | + | + | chr12 | chr12 | 133067447 | 132635526 |
| FBRSL1 | NOC4L | 10 | + | + | chr12 | chr12 | 133067447 | 132635526 |
| MAPKAPK5 | ACAD10 | 10 | + | + | chr12 | chr12 | 112308984 | 112182447 |
| MAPKAPK5 | ACAD10 | 10 | + | + | chr12 | chr12 | 112308984 | 112182447 |
| MAPKAPK5 | ACAD10 | 10 | + | + | chr12 | chr12 | 112308984 | 112182447 |
| MAPKAPK5 | ACAD10 | 10 | + | + | chr12 | chr12 | 112308984 | 112182447 |
| MAPKAPK5 | ACAD10 | 10 | + | + | chr12 | chr12 | 112308984 | 112182447 |
| MAPKAPK5 | ACAD10 | 10 | + | + | chr12 | chr12 | 112308984 | 112182447 |
| MAPKAPK5 | ACAD10 | 10 | + | + | chr12 | chr12 | 112308984 | 112182447 |
| GGACT | PCCA | 9 | − | + | chr13 | chr13 | 101236079 | 101179929 |
| GGACT | PCCA | 9 | − | + | chr13 | chr13 | 101236079 | 101179929 |
| GGACT | PCCA | 9 | − | + | chr13 | chr13 | 101236079 | 101179929 |
| GGACT | PCCA | 9 | − | + | chr13 | chr13 | 101236079 | 101179929 |
| TMPRSS2 | ERG | 9 | − | − | chr21 | chr21 | 42879877 | 39956869 |
| PML | RARA | 8 | + | + | chr15 | chr17 | 74325755 | 38504568 |
| C10orf68 | CCDC7 | 7 | + | + | chr10 | chr10 | 32856819 | 32832228 |
| CLPS | CPA1 | 7 | − | + | chr6 | chr7 | 35764982 | 130027665 |
| MATR3 | CTNNA1 | 7 | + | + | chr5 | chr5 | 138629494 | 138145727 |
| MATR3 | CTNNA1 | 7 | + | + | chr5 | chr5 | 138629494 | 138145727 |
| MATR3 | CTNNA1 | 7 | + | + | chr5 | chr5 | 138629494 | 138145727 |
| MATR3 | CTNNA1 | 7 | + | + | chr5 | chr5 | 138629494 | 138145727 |
| SBNO2 | SERINC2 | 7 | − | + | chr19 | chr1 | 1149368 | 31905814 |
| SBNO2 | SERINC2 | 7 | − | + | chr19 | chr1 | 1149368 | 31905814 |
| SBNO2 | SERINC2 | 7 | − | + | chr19 | chr1 | 1149368 | 31905814 |
| LYPD6 | LYPD6B | 6 | + | + | chr2 | chr2 | 150187236 | 149987397 |
| MBD5 | ORC4 | 6 | + | − | chr2 | chr2 | 148779253 | 148733544 |
| MBD5 | ORC4 | 6 | + | − | chr2 | chr2 | 148779253 | 148733544 |
| MBD5 | ORC4 | 6 | + | − | chr2 | chr2 | 148779253 | 148733544 |
| TMPRSS2 | ERG | 6 | − | − | chr21 | chr21 | 42866283 | 39817544 |
| UBAP1 | UBE2R2 | 6 | + | + | chr9 | chr9 | 34179238 | 33886879 |
| CD44 | PDHX | 5 | + | + | chr11 | chr11 | 35211612 | 34952951 |
| CD44 | PDHX | 5 | + | + | chr11 | chr11 | 35211612 | 34952951 |
| CPSF6 | LOC93622 | 5 | + | + | chr12 | chr4 | 69656342 | 6676720 |
| CPSF6 | LOC93622 | 5 | + | + | chr12 | chr4 | 69656342 | 6676720 |
| CPSF6 | LOC93622 | 5 | + | + | chr12 | chr4 | 69656342 | 6676720 |
| CPSF6 | LOC93622 | 5 | + | + | chr12 | chr4 | 69656342 | 6676720 |
| 6-Mar | CCT5 | 5 | + | + | chr5 | chr5 | 10394897 | 10254257 |
| 6-Mar | CCT5 | 5 | + | + | chr5 | chr5 | 10394897 | 10254257 |
| RPS6KB1 | VMP1 | 5 | + | + | chr17 | chr17 | 57970686 | 57915656 |
| RPS6KB1 | VMP1 | 5 | + | + | chr17 | chr17 | 57970686 | 57915656 |
| RPS6KB1 | VMP1 | 5 | + | + | chr17 | chr17 | 57970686 | 57915656 |
| TMEM135 | LOC100506368 | 5 | + | + | chr11 | chr11 | 86802437 | 86669024 |

TABLE 1-continued

Chimeras Unveiled by sMACHETE

| 5'-Gene (gene1) | 3'-Gene (gene2) | Number of Samples Found to Have Chimera | strand 1 | strand 2 | chr1 | chr2 | pos1 | pos2 |
|---|---|---|---|---|---|---|---|---|
| TMEM135 | LOC100506368 | 5 | + | + | chr11 | chr11 | 86802437 | 86669024 |
| TMEM135 | LOC100506368 | 5 | + | + | chr11 | chr11 | 86802437 | 86669024 |
| VRK2 | FANCL | 5 | + | − | chr2 | chr2 | 58373609 | 58393009 |
| VRK2 | FANCL | 5 | + | − | chr2 | chr2 | 58373609 | 58393009 |
| VRK2 | FANCL | 5 | + | − | chr2 | chr2 | 58373609 | 58393009 |
| VRK2 | FANCL | 5 | + | − | chr2 | chr2 | 58373609 | 58393009 |
| CHD7 | RAB2A | 4 | + | + | chr8 | chr8 | 61591641 | 61471411 |
| CHD7 | RAB2A | 4 | + | + | chr8 | chr8 | 61591641 | 61471411 |
| CPSF6 | CREBZF | 4 | + | − | chr12 | chr11 | 69656342 | 85371641 |
| CPSF6 | CREBZF | 4 | + | − | chr12 | chr11 | 69656342 | 85371641 |
| CPSF6 | CREBZF | 4 | + | − | chr12 | chr11 | 69656342 | 85371641 |
| LOC100507424 | ITFG2 | 4 | + | + | chr12 | chr12 | 2946122 | 2931960 |
| LOC100507424 | ITFG2 | 4 | + | + | chr12 | chr12 | 2946122 | 2931960 |
| MGRN1 | HMOX2 | 4 | + | + | chr16 | chr16 | 4675049 | 4555485 |
| MGRN1 | HMOX2 | 4 | + | + | chr16 | chr16 | 4675049 | 4555485 |
| MGRN1 | HMOX2 | 4 | + | + | chr16 | chr16 | 4675049 | 4555485 |
| PSMD14 | TANK | 4 | + | + | chr2 | chr2 | 162175384 | 162036125 |
| PSMD14 | TANK | 4 | + | + | chr2 | chr2 | 162175384 | 162036125 |
| PSMD14 | TANK | 4 | + | + | chr2 | chr2 | 162175384 | 162036125 |
| RARA | PML | 4 | + | + | chr17 | chr15 | 38487648 | 74326819 |
| RCC1 | PHACTR4 | 4 | + | + | chr1 | chr1 | 28832596 | 28817463 |
| RCC1 | PHACTR4 | 4 | + | + | chr1 | chr1 | 28832596 | 28817463 |
| TBL1XR1 | PIK3CA | 4 | − | + | chr3 | chr3 | 176914909 | 178916538 |
| TBL1XR1 | PIK3CA | 4 | − | + | chr3 | chr3 | 176914909 | 178916538 |
| XKR9 | LACTB2 | 4 | + | − | chr8 | chr8 | 71581773 | 71556478 |
| XKR9 | LACTB2 | 4 | + | − | chr8 | chr8 | 71581773 | 71556478 |
| ARHGEF38 | PPA2 | 3 | + | − | chr4 | chr4 | 106474118 | 106377902 |
| ARHGEF38 | PPA2 | 3 | + | − | chr4 | chr4 | 106474118 | 106377902 |
| CENPW | TRMT11 | 3 | + | + | chr6 | chr6 | 126667464 | 126359851 |
| CPSF6 | TMBIM4 | 3 | + | − | chr12 | chr12 | 69656342 | 66547228 |
| CPSF6 | TMBIM4 | 3 | + | − | chr12 | chr12 | 69656342 | 66547228 |
| ETV6 | NTRK3 | 3 | + | − | chr12 | chr15 | 12022903 | 88483984 |
| ETV6 | NTRK3 | 3 | + | − | chr12 | chr15 | 12022903 | 88483984 |
| OAS2 | OAS1 | 3 | + | + | chr12 | chr12 | 113416590 | 113354314 |
| OAS2 | OAS1 | 3 | + | + | chr12 | chr12 | 113416590 | 113354314 |
| PML | RARA | 3 | + | + | chr15 | chr17 | 74317268 | 38504568 |
| PTRH2 | VMP1 | 3 | − | + | chr17 | chr17 | 57784732 | 57842332 |
| PTRH2 | VMP1 | 3 | − | + | chr17 | chr17 | 57784732 | 57842332 |
| PTRH2 | VMP1 | 3 | − | + | chr17 | chr17 | 57784732 | 57842332 |
| RALA | YAE1D1 | 3 | + | + | chr7 | chr7 | 39663424 | 39610105 |
| TMPRSS2 | ERG | 3 | − | − | chr21 | chr21 | 42880008 | 39947671 |
| ACACB | UNG | 2 | + | + | chr12 | chr12 | 109665294 | 109547634 |
| ACACB | UNG | 2 | + | + | chr12 | chr12 | 109665294 | 109547634 |
| BCR | ABL1 | 2 | + | + | chr22 | chr9 | 23524426 | 133729451 |
| CAV1 | TES | 2 | + | + | chr7 | chr7 | 116166743 | 115897348 |
| CAV1 | TES | 2 | + | + | chr7 | chr7 | 116166743 | 115897348 |
| CCAR1 | HNRNPH3 | 2 | + | + | chr10 | chr10 | 70532856 | 70096956 |
| CCAR1 | HNRNPH3 | 2 | + | + | chr10 | chr10 | 70532856 | 70096956 |
| CCDC91 | MRPS35 | 2 | + | + | chr12 | chr12 | 28637098 | 27888380 |
| CCDC91 | MRPS35 | 2 | + | + | chr12 | chr12 | 28637098 | 27888380 |
| CEP350 | TOR1AIP1 | 2 | + | + | chr1 | chr1 | 179956421 | 179858448 |
| CEP350 | TOR1AIP1 | 2 | + | + | chr1 | chr1 | 179956421 | 179858448 |
| CP | HPS3 | 2 | − | + | chr3 | chr3 | 148895627 | 148889882 |
| CPM | LYZ | 2 | − | + | chr12 | chr12 | 69326458 | 69743888 |
| CPM | LYZ | 2 | − | + | chr12 | chr12 | 69326458 | 69743888 |
| CRTC1 | KLHL26 | 2 | + | + | chr19 | chr19 | 18794638 | 18775071 |
| CRTC1 | KLHL26 | 2 | + | + | chr19 | chr19 | 18794638 | 18775071 |
| DIP2B | TMBIM6 | 2 | + | + | chr12 | chr12 | 50899023 | 50146247 |
| DIP2B | TMBIM6 | 2 | + | + | chr12 | chr12 | 50899023 | 50146247 |
| DOK7 | RGS12 | 2 | + | + | chr4 | chr4 | 3465278 | 3415799 |
| DOK7 | RGS12 | 2 | + | + | chr4 | chr4 | 3465278 | 3415799 |
| EBF3 | MGMT | 2 | − | + | chr10 | chr10 | 131755522 | 131506159 |
| EBF3 | MGMT | 2 | − | + | chr10 | chr10 | 131755522 | 131506159 |
| ERBB2 | PPP1R1B | 2 | + | + | chr17 | chr17 | 37883800 | 37791860 |
| ERBB2 | PPP1R1B | 2 | + | + | chr17 | chr17 | 37883800 | 37791860 |
| EXOSC8 | SUPT20H | 2 | + | − | chr13 | chr13 | 37574959 | 37586434 |
| FGFR3 | TACC3 | 2 | + | + | chr4 | chr4 | 1808661 | 1739325 |
| FRS2 | DTX3 | 2 | + | + | chr12 | chr12 | 69864310 | 58002860 |
| GPR35 | ANKMY1 | 2 | + | − | chr2 | chr2 | 241558448 | 241468926 |
| ITCH | ASIP | 2 | + | + | chr20 | chr20 | 32981687 | 32848171 |

TABLE 1-continued

Chimeras Unveiled by sMACHETE

| 5'-Gene (gene1) | 3'-Gene (gene2) | Number of Samples Found to Have Chimera | strand 1 | strand 2 | chr1 | chr2 | pos1 | pos2 |
|---|---|---|---|---|---|---|---|---|
| ITCH | ASIP | 2 | + | + | chr20 | chr20 | 32981687 | 32848171 |
| ITPKC | LTBP4 | 2 | + | + | chr19 | chr19 | 41231344 | 41110941 |
| ITPKC | LTBP4 | 2 | + | + | chr19 | chr19 | 41231344 | 41110941 |
| LAPTM4B | MTDH | 2 | + | + | chr8 | chr8 | 98817692 | 98731277 |
| LAPTM4B | MTDH | 2 | + | + | chr8 | chr8 | 98817692 | 98731277 |
| LDLRAD3 | TRIM44 | 2 | + | + | chr11 | chr11 | 36120011 | 35827908 |
| LDLRAD3 | TRIM44 | 2 | + | + | chr11 | chr11 | 36120011 | 35827908 |
| LGR6 | GPR37L1 | 2 | + | + | chr1 | chr1 | 202205121 | 202096869 |
| LMLN | RPL35A | 2 | + | + | chr3 | chr3 | 197707375 | 197680874 |
| LMLN | RPL35A | 2 | + | + | chr3 | chr3 | 197707375 | 197680874 |
| LRIG3 | ATF7 | 2 | − | − | chr12 | chr12 | 59307763 | 53946421 |
| LRIG3 | ATF7 | 2 | − | − | chr12 | chr12 | 59307763 | 53994805 |
| MYO3B | TSHZ2 | 2 | + | + | chr2 | chr20 | 171092646 | 52103683 |
| NRBP1 | SNX17 | 2 | + | + | chr2 | chr2 | 27660227 | 27598373 |
| NRBP1 | SNX17 | 2 | + | + | chr2 | chr2 | 27660227 | 27598373 |
| NSD1 | NUP98 | 2 | + | − | chr5 | chr11 | 176639196 | 3756554 |
| NUP35 | KCNH7 | 2 | + | − | chr2 | chr2 | 184016377 | 163292107 |
| PICALM | MLLT10 | 2 | − | + | chr11 | chr10 | 85685751 | 21940602 |
| PKP4 | PDE1A | 2 | + | + | chr2 | chr2 | 159459616 | 183011879 |
| PPHLN1 | TIMELESS | 2 | + | − | chr12 | chr12 | 42787491 | 56818936 |
| PTRH2 | VMP1 | 2 | − | + | chr17 | chr17 | 57784732 | 57808782 |
| PTRH2 | VMP1 | 2 | − | + | chr17 | chr17 | 57784732 | 57808782 |
| RPS6KB1 | VMP1 | 2 | + | + | chr17 | chr17 | 57992064 | 57886157 |
| RPS6KB1 | VMP1 | 2 | + | + | chr17 | chr17 | 57992064 | 57886157 |
| SDCCAG8 | CEP170 | 2 | + | − | chr1 | chr1 | 243419542 | 243388623 |
| SDCCAG8 | CEP170 | 2 | + | − | chr1 | chr1 | 243419542 | 243388623 |
| SPOPL | HNMT | 2 | + | + | chr2 | chr2 | 139259689 | 138758488 |
| SPOPL | HNMT | 2 | + | + | chr2 | chr2 | 139259689 | 138758488 |
| TAF4 | TSHZ2 | 2 | − | + | chr20 | chr20 | 60572606 | 52103683 |
| THRA | GSDMA | 2 | + | + | chr17 | chr17 | 38233191 | 38121936 |
| THRA | GSDMA | 2 | + | + | chr17 | chr17 | 38233191 | 38121936 |
| THRA | GSDMA | 2 | + | + | chr17 | chr17 | 38233861 | 38121936 |
| THRA | GSDMA | 2 | + | + | chr17 | chr17 | 38233861 | 38121936 |
| TSFM | AVIL | 2 | + | − | chr12 | chr12 | 58177066 | 58194995 |
| TSFM | AVIL | 2 | + | − | chr12 | chr12 | 58177066 | 58194995 |
| TSHZ3 | CDH2 | 2 | − | − | chr19 | chr18 | 31840086 | 25593873 |
| AAAS | C12orf10 | 1 | − | + | chr12 | chr12 | 53714349 | 53699692 |
| ABCA5 | DTNB | 1 | − | + | chr17 | chr2 | 67323193 | 25611230 |
| ACTN4 | CAPN12 | 1 | + | − | chr19 | chr19 | 39212328 | 39221863 |
| ADAM15 | CHD1L | 1 | + | + | chr1 | chr1 | 155032450 | 146739085 |
| ADAM9 | C17orf51 | 1 | + | − | chr8 | chr17 | 38913291 | 21438799 |
| ADAM9 | CRB1 | 1 | + | + | chr8 | chr1 | 38854679 | 197297552 |
| ADCK3 | EPHX1 | 1 | + | + | chr1 | chr1 | 227128100 | 226032199 |
| ADCK5 | INPP5B | 1 | + | − | chr1 | chr1 | 145603179 | 38328102 |
| AEBP2 | LMO3 | 1 | + | − | chr12 | chr12 | 19646920 | 16753802 |
| AFF1 | PTPN13 | 1 | + | + | chr4 | chr4 | 88053560 | 87693931 |
| AGPAT6 | ADAM9 | 1 | + | + | chr8 | chr8 | 41456823 | 38899465 |
| AGPAT9 | COPS4 | 1 | + | + | chr4 | chr4 | 84465755 | 83987591 |
| AGRN | CDC42BPG | 1 | + | − | chr1 | chr11 | 989931 | 64600431 |
| AKAP11 | MRPS31 | 1 | + | − | chr13 | chr13 | 42882745 | 41303737 |
| AKAP6 | EGLN3 | 1 | + | + | chr14 | chr14 | 32903023 | 34400421 |
| AKT3 | SDCCAG8 | 1 | − | + | chr1 | chr1 | 243736228 | 243579004 |
| ALG11 | PROSER1 | 1 | + | − | chr13 | chr13 | 52586598 | 39602457 |
| ANKRD11 | DYNLRB2 | 1 | − | + | chr16 | chr16 | 89556653 | 80583381 |
| ANKRD11 | PARVA | 1 | − | + | chr16 | chr11 | 89484692 | 12495292 |
| ANKRD12 | CCDC178 | 1 | + | − | chr18 | chr18 | 9136963 | 30518055 |
| ANKRD33B | ADAMTS16 | 1 | + | + | chr5 | chr5 | 10564945 | 5232354 |
| AP3D1 | DOT1L | 1 | − | + | chr19 | chr19 | 2151238 | 2210399 |
| AP4B1 | C20orf194 | 1 | − | + | chr1 | chr20 | 114447227 | 3356949 |
| APBB2 | MPPED2 | 1 | − | − | chr4 | chr11 | 41015600 | 30602041 |
| ARFGEF2 | NCOA3 | 1 | + | + | chr20 | chr20 | 47580435 | 46211927 |
| ARFGEF2 | NCOA3 | 1 | + | + | chr20 | chr20 | 47582560 | 46211927 |
| ARHGAP35 | IGFL2 | 1 | + | + | chr19 | chr19 | 47440665 | 46663672 |
| ARHGEF25 | B4GALNT1 | 1 | + | − | chr12 | chr12 | 58010278 | 58022929 |
| ARID1A | BEND5 | 1 | + | + | chr1 | chr1 | 27024031 | 49202124 |
| ARIH1 | THSD4 | 1 | + | + | chr15 | chr15 | 72810475 | 72057359 |
| ARL8B | ITPR1 | 1 | + | + | chr3 | chr3 | 5164273 | 4852949 |
| ASRGL1 | SCGB1D1 | 1 | + | + | chr11 | chr11 | 62105639 | 61960871 |
| ATF7IP | FAM83B | 1 | + | + | chr12 | chr6 | 14518761 | 54804504 |
| ATG13 | TSPAN18 | 1 | + | + | chr11 | chr11 | 46639440 | 44881879 |

TABLE 1-continued

Chimeras Unveiled by sMACHETE

| 5'-Gene (gene1) | 3'-Gene (gene2) | Number of Samples Found to Have Chimera | strand 1 | strand 2 | Junction Locus Data | | | |
|---|---|---|---|---|---|---|---|---|
| | | | | | chr1 | chr2 | pos1 | pos2 |
| ATG4C | NFIA | 1 | + | + | chr1 | chr1 | 63270926 | 61798184 |
| ATM | ACAT1 | 1 | + | + | chr11 | chr11 | 108203627 | 108017997 |
| ATP11B | CARS | 1 | + | − | chr3 | chr11 | 182563310 | 3026663 |
| ATP1A1OS | ATP1A1 | 1 | − | + | chr1 | chr1 | 116961081 | 116943483 |
| ATP2A2 | IFT81 | 1 | + | + | chr12 | chr12 | 110771948 | 110641669 |
| ATP2B4 | MRPS21 | 1 | + | + | chr1 | chr1 | 203696699 | 150280482 |
| ATP2B4 | PRELP | 1 | + | + | chr1 | chr1 | 203596347 | 203452297 |
| ATP9B | LUC7L | 1 | + | − | chr18 | chr16 | 76953263 | 258187 |
| ATXN2L | CCDC101 | 1 | + | + | chr16 | chr16 | 28834879 | 28600421 |
| AUTS2 | ACTR1A | 1 | + | − | chr7 | chr10 | 69364484 | 104250370 |
| AVL9 | ZNF544 | 1 | + | + | chr7 | chr19 | 32535414 | 58772217 |
| AXIN1 | BBX | 1 | − | + | chr16 | chr3 | 396148 | 107466812 |
| B3GALTL | MTUS2 | 1 | + | + | chr13 | chr13 | 31898032 | 30014120 |
| B3GNT2 | KIAA1841 | 1 | + | + | chr2 | chr2 | 62423490 | 61304055 |
| B3GNT2 | KIAA1841 | 1 | + | + | chr2 | chr2 | 62423490 | 61308587 |
| B4GALT1 | STRA8 | 1 | − | + | chr9 | chr7 | 33166756 | 134925271 |
| BAI2 | HS3ST4 | 1 | + | + | chr1 | chr16 | 32221600 | 26146933 |
| BAI2 | HS3ST4 | 1 | + | + | chr1 | chr16 | 32229485 | 26146933 |
| BAIAP2L1 | DMTF1 | 1 | − | + | chr7 | chr7 | 98030114 | 86800311 |
| BCAS3 | CACNG6 | 1 | + | + | chr17 | chr19 | 59024713 | 54515205 |
| BCAT1 | USP15 | 1 | − | + | chr12 | chr12 | 25002720 | 62687960 |
| BCKDK | HSD3B7 | 1 | + | + | chr16 | chr16 | 31119800 | 30998161 |
| BCL2L1 | RHAG | 1 | − | − | chr20 | chr6 | 30309458 | 49583484 |
| BCL2L1 | RHAG | 1 | − | − | chr20 | chr6 | 30309647 | 49583484 |
| BCL2L11 | AFMID | 1 | + | + | chr2 | chr17 | 111881716 | 76187051 |
| BCL2L11 | BIRC5 | 1 | + | + | chr2 | chr17 | 111881716 | 76210761 |
| BCLAF1 | COL21A1 | 1 | − | − | chr6 | chr6 | 136610851 | 56047454 |
| BCRP2 | UFD1L | 1 | + | − | chr22 | chr22 | 21457515 | 19445662 |
| C11orf30 | LRP5 | 1 | + | + | chr11 | chr11 | 76175124 | 68153784 |
| C12orf49 | MDM2 | 1 | − | + | chr12 | chr12 | 117175595 | 69229609 |
| C12orf49 | SLC35E3 | 1 | − | + | chr12 | chr12 | 117175595 | 69145812 |
| C12orf49 | TMEM120B | 1 | − | + | chr12 | chr12 | 117175595 | 122181535 |
| C12orf5 | TSPAN9 | 1 | + | + | chr12 | chr12 | 4430469 | 3310343 |
| C12orf5 | TSPAN9 | 1 | + | + | chr12 | chr12 | 4430469 | 3387587 |
| C16orf45 | RHBDL2 | 1 | + | − | chr16 | chr1 | 15528616 | 39385009 |
| C19orf25 | MED1 | 1 | − | − | chr19 | chr17 | 1478773 | 37604157 |
| C19orf47 | SCN1B | 1 | − | + | chr19 | chr19 | 40847693 | 35523432 |
| C19orf47 | SCN1B | 1 | − | + | chr19 | chr19 | 40847746 | 35523432 |
| CAB39L | USP12 | 1 | − | − | chr13 | chr13 | 49906083 | 27649525 |
| CABIN1 | MIF | 1 | + | + | chr22 | chr22 | 24530382 | 24236956 |
| CACNG4 | VMP1 | 1 | + | + | chr17 | chr17 | 64961247 | 57851115 |
| CADM1 | SORL1 | 1 | − | + | chr11 | chr11 | 115374989 | 121424646 |
| CALD1 | EXOC4 | 1 | + | + | chr7 | chr7 | 134552555 | 133502078 |
| CAMK1D | DHTKD1 | 1 | + | + | chr10 | chr10 | 12391909 | 12159672 |
| CAMK1D | DHTKD1 | 1 | + | + | chr10 | chr10 | 12391909 | 12160748 |
| CAMTA1 | CHST4 | 1 | + | + | chr1 | chr16 | 6885270 | 71570563 |
| CAPN1 | MRPL49 | 1 | + | + | chr11 | chr11 | 64956217 | 64891974 |
| CARD8 | SULT2B1 | 1 | − | + | chr19 | chr19 | 48752780 | 49099996 |
| CARM1 | C19orf38 | 1 | + | + | chr19 | chr19 | 10982598 | 10960935 |
| CARS | PLD3 | 1 | − | + | chr11 | chr19 | 3078573 | 40872326 |
| CASC4 | LRRC8D | 1 | + | + | chr15 | chr1 | 44630515 | 90398626 |
| CAT | CD3D | 1 | + | − | chr11 | chr11 | 34460626 | 118210209 |
| CAT | CD3D | 1 | + | − | chr11 | chr11 | 34460626 | 118210621 |
| CAT | CD3D | 1 | + | − | chr11 | chr11 | 34460626 | 118211308 |
| CBFB | MYH11 | 1 | + | − | chr16 | chr16 | 67116211 | 15820911 |
| CBX3 | HNRNPA2B1 | 1 | + | − | chr7 | chr7 | 26248175 | 26237081 |
| CCBP2 | NKTR | 1 | + | + | chr3 | chr3 | 42851024 | 42683993 |
| CCDC107 | PITPNB | 1 | + | − | chr9 | chr22 | 35660644 | 28310335 |
| CCND3 | PPP2R5D | 1 | − | + | chr6 | chr6 | 42016239 | 42957349 |
| CCSER1 | MMRN1 | 1 | + | + | chr4 | chr4 | 91048982 | 90844319 |
| CD44 | PDHX | 1 | + | + | chr11 | chr11 | 35201954 | 34978931 |
| CDH1 | CDH3 | 1 | + | + | chr16 | chr16 | 68772314 | 68710288 |
| CDH1 | CDKL3 | 1 | + | − | chr16 | chr5 | 68856128 | 133642393 |
| CDH23 | NSD1 | 1 | + | + | chr10 | chr5 | 73501678 | 176618885 |
| CDK13 | POU6F2 | 1 | + | + | chr7 | chr7 | 39991451 | 39472676 |
| CDK2 | PAN2 | 1 | + | − | chr12 | chr12 | 56363360 | 56719238 |
| CELSR2 | KIAA1324 | 1 | + | + | chr1 | chr1 | 109808828 | 109714488 |
| CEP192 | PSMG2 | 1 | + | + | chr18 | chr18 | 13092526 | 12718516 |
| CGRRF1 | CDKN3 | 1 | + | + | chr14 | chr14 | 54976781 | 54866612 |
| CHAF1B | DOPEY2 | 1 | + | + | chr21 | chr21 | 37763966 | 37665618 |

TABLE 1-continued

Chimeras Unveiled by sMACHETE

| 5'-Gene (gene1) | 3'-Gene (gene2) | Number of Samples Found to Have Chimera | strand 1 | strand 2 | Junction Locus Data | | | |
|---|---|---|---|---|---|---|---|---|
| | | | | | chr1 | chr2 | pos1 | pos2 |
| CHD4 | FYTTD1 | 1 | − | + | chr12 | chr3 | 6710814 | 197501020 |
| CHD7 | TOX | 1 | + | − | chr8 | chr8 | 61655656 | 59852103 |
| CHI3L1 | PTPRZ1 | 1 | − | + | chr1 | chr7 | 203153704 | 121668606 |
| CHID1 | RRBP1 | 1 | − | − | chr11 | chr20 | 910775 | 17610606 |
| CHURC1 | GPX2 | 1 | + | − | chr14 | chr14 | 65390844 | 65406556 |
| CIRBP | WDR18 | 1 | + | + | chr19 | chr19 | 1269409 | 994019 |
| CLASP2 | STT3B | 1 | − | + | chr3 | chr3 | 33725851 | 31617888 |
| CLCN4 | WWC3 | 1 | + | + | chrX | chrX | 10126591 | 10084458 |
| CLEC16A | TXNDC11 | 1 | + | − | chr16 | chr16 | 11076848 | 11778101 |
| CLIP1 | NCOA3 | 1 | − | + | chr12 | chr20 | 122907068 | 46266392 |
| CLPB | ARMC4 | 1 | − | − | chr11 | chr10 | 72012847 | 28229734 |
| CNOT1 | PEPD | 1 | − | − | chr16 | chr19 | 58633140 | 33882385 |
| CNOT2 | DTX3 | 1 | + | + | chr12 | chr12 | 70672054 | 58002860 |
| CNOT2 | LYZ | 1 | + | + | chr12 | chr12 | 70672054 | 69743888 |
| CNOT2 | MBD4 | 1 | + | + | chr12 | chr3 | 70713144 | 129152979 |
| CNOT2 | TRMT10C | 1 | + | + | chr12 | chr3 | 70713144 | 101283614 |
| COG2 | PGAM5 | 1 | + | + | chr1 | chr12 | 230778424 | 133294025 |
| COG5 | DPP6 | 1 | − | + | chr7 | chr7 | 107052947 | 154519477 |
| COG5 | FOXP2 | 1 | − | + | chr7 | chr7 | 107167682 | 114329837 |
| COL15A1 | LINGO2 | 1 | + | − | chr9 | chr9 | 101706532 | 28947912 |
| COL3A1 | COL1A2 | 1 | + | + | chr2 | chr7 | 189871178 | 94055735 |
| COLEC11 | PINX1 | 1 | + | − | chr2 | chr8 | 3652060 | 10692285 |
| CPM | MON2 | 1 | − | + | chr12 | chr12 | 69326458 | 62926218 |
| CPSF6 | PRIM2 | 1 | + | + | chr12 | chr6 | 69656342 | 57372288 |
| CPSF6 | SSR1 | 1 | + | − | chr12 | chr6 | 69656342 | 7310262 |
| CPSF7 | SDHAF2 | 1 | − | + | chr11 | chr11 | 61196654 | 61213413 |
| CREB5 | KCNH2 | 1 | + | − | chr7 | chr7 | 28610155 | 150646137 |
| CREB5 | KCNH2 | 1 | + | − | chr7 | chr7 | 28610155 | 150647508 |
| CREBBP | KAT6A | 1 | − | − | chr16 | chr8 | 3929833 | 41792385 |
| CTDP1 | ZNF271 | 1 | + | + | chr18 | chr18 | 77473138 | 32885940 |
| CTDSPL | TMCC1 | 1 | + | − | chr3 | chr3 | 38012990 | 129390107 |
| CYTH3 | RALA | 1 | − | + | chr7 | chr7 | 6210461 | 39729981 |
| DBF4B | DYNC2H1 | 1 | + | + | chr17 | chr11 | 42786734 | 103036627 |
| DDX10 | AIPL1 | 1 | + | − | chr11 | chr17 | 108594189 | 6331826 |
| DENND1B | CCSER1 | 1 | − | + | chr1 | chr4 | 197741998 | 91736913 |
| DICER1 | UVRAG | 1 | − | + | chr14 | chr11 | 95623567 | 75826968 |
| DLD | HBP1 | 1 | + | + | chr7 | chr7 | 107533723 | 106836279 |
| DLG1 | EHHADH | 1 | − | − | chr3 | chr3 | 196863413 | 184966305 |
| DNAH17 | NCAN | 1 | − | + | chr17 | chr19 | 76503360 | 19327756 |
| DNM2 | TMED1 | 1 | + | + | chr19 | chr19 | 10930765 | 10943889 |
| DOK7 | TMEM129 | 1 | + | − | chr4 | chr4 | 3478269 | 1720353 |
| DOT1L | BTBD2 | 1 | + | − | chr19 | chr19 | 2223485 | 1997462 |
| DPF2 | POLA2 | 1 | + | + | chr11 | chr11 | 65113830 | 65049950 |
| DPM1 | GRID1 | 1 | − | − | chr20 | chr10 | 49571723 | 87675996 |
| DSTN | CCDC127 | 1 | + | − | chr20 | chr5 | 17550856 | 206073 |
| DTX3 | MARS | 1 | + | + | chr12 | chr12 | 58000301 | 57898008 |
| DYNC2H1 | YAP1 | 1 | + | + | chr11 | chr11 | 103153814 | 102033187 |
| DYNLRB1 | RALY | 1 | + | + | chr20 | chr20 | 33114148 | 32667716 |
| DYRK1A | MORC3 | 1 | + | + | chr21 | chr21 | 38739930 | 37705944 |
| EBF4 | TMC2 | 1 | + | + | chr20 | chr20 | 2674428 | 2621780 |
| ECE2 | DVL3 | 1 | + | + | chr3 | chr3 | 183967678 | 183881445 |
| EEF1D | KRT7 | 1 | − | + | chr8 | chr12 | 144663399 | 52642375 |
| EEF2K | UQCRC2 | 1 | + | + | chr16 | chr16 | 22218000 | 21991868 |
| EGFR | PPM1H | 1 | + | − | chr7 | chr12 | 55087058 | 63195940 |
| EIF2B1 | GLIPR1L2 | 1 | − | + | chr12 | chr12 | 124118092 | 75796797 |
| EIF3J | CTDSPL2 | 1 | + | + | chr15 | chr15 | 44829625 | 44816307 |
| EIF3K | RYR1 | 1 | + | + | chr19 | chr19 | 39125758 | 39077965 |
| ELMSAN1 | ACOT1 | 1 | − | + | chr14 | chr14 | 74226466 | 74008197 |
| EMC10 | MYBPC2 | 1 | + | + | chr19 | chr19 | 50979915 | 50967603 |
| EMC7 | CD27 | 1 | − | + | chr15 | chr12 | 34388096 | 6559339 |
| EMC9 | IRF9 | 1 | + | − | chr14 | chr14 | 24610098 | 24633087 |
| EML4 | NTRK3 | 1 | + | − | chr2 | chr15 | 42491871 | 88576276 |
| ENDOV | RNF213 | 1 | + | + | chr17 | chr17 | 78403631 | 78362412 |
| ENPP1 | SEC63 | 1 | + | − | chr6 | chr6 | 132207864 | 108246136 |
| ENTPD7 | IDE | 1 | − | + | chr10 | chr10 | 101439632 | 94250321 |
| EP300 | RBX1 | 1 | + | + | chr22 | chr22 | 41513825 | 41349559 |
| EPB41L1 | CNBD2 | 1 | + | − | chr20 | chr20 | 34700402 | 34618279 |
| EPC2 | MBD5 | 1 | + | + | chr2 | chr2 | 149447942 | 149099783 |
| EPG5 | RAB38 | 1 | − | − | chr18 | chr11 | 43467716 | 87847308 |
| EPS15 | TRABD2B | 1 | − | − | chr1 | chr1 | 51984871 | 48267291 |

TABLE 1-continued

Chimeras Unveiled by sMACHETE

| 5'-Gene (gene1) | 3'-Gene (gene2) | Number of Samples Found to Have Chimera | strand 1 | strand 2 | Junction Locus Data | | | |
|---|---|---|---|---|---|---|---|---|
| | | | | | chr1 | chr2 | pos1 | pos2 |
| ERG | PLEKHH1 | 1 | − | + | chr21 | chr14 | 39947586 | 68022542 |
| ERG | SON | 1 | − | + | chr21 | chr21 | 39947586 | 34918519 |
| ERGIC1 | KCNIP1 | 1 | + | + | chr5 | chr5 | 172261436 | 170145762 |
| ERGIC3 | GLS2 | 1 | + | − | chr20 | chr12 | 34145020 | 56872046 |
| ESD | FAM124A | 1 | − | + | chr13 | chr13 | 47367532 | 51825604 |
| ESR1 | DYNC1LI1 | 1 | + | − | chr6 | chr3 | 152332929 | 32571152 |
| ESRP2 | SLC7A6 | 1 | − | + | chr16 | chr16 | 68265081 | 68321649 |
| FAM222B | C16orf62 | 1 | − | + | chr17 | chr16 | 27169700 | 19637499 |
| FAM222B | C16orf62 | 1 | − | + | chr17 | chr16 | 27169700 | 19639016 |
| FAM35A | GLUD1 | 1 | + | − | chr10 | chr10 | 88856746 | 88811627 |
| FAM47E | TMEM184B | 1 | + | − | chr4 | chr22 | 77184996 | 38644025 |
| FAM83D | SF3B3 | 1 | + | + | chr20 | chr16 | 37570769 | 70597779 |
| FBN1 | URI1 | 1 | − | + | chr15 | chr19 | 48936803 | 30462100 |
| FBN1 | URI1 | 1 | − | + | chr15 | chr19 | 48936803 | 30476130 |
| FBRSL1 | SFSWAP | 1 | + | + | chr12 | chr12 | 133067447 | 132226610 |
| FBXL18 | WDR83OS | 1 | − | − | chr7 | chr19 | 5540119 | 12780047 |
| FBXL19 | RNF40 | 1 | + | + | chr16 | chr16 | 30941905 | 30785259 |
| FBXO8 | PALLD | 1 | − | + | chr4 | chr4 | 175204561 | 169589341 |
| FCHSD1 | NCKAP1L | 1 | − | + | chr5 | chr12 | 141029926 | 54936359 |
| FCHSD1 | NCKAP1L | 1 | − | + | chr5 | chr12 | 141030587 | 54936359 |
| FGD6 | PTPRR | 1 | − | − | chr12 | chr12 | 95483345 | 71033057 |
| FGFR2 | USP10 | 1 | − | + | chr10 | chr16 | 123353223 | 84792322 |
| FKBP8 | SLC1A6 | 1 | − | − | chr19 | chr19 | 18648411 | 15061202 |
| FLJ43663 | PRTG | 1 | − | − | chr7 | chr15 | 130737184 | 55976129 |
| FLNB | SLMAP | 1 | + | + | chr3 | chr3 | 58095897 | 57843460 |
| FLOT2 | SUPT6H | 1 | − | + | chr17 | chr17 | 27224544 | 27013357 |
| FN3K | HEXDC | 1 | + | + | chr17 | chr17 | 80693653 | 80397507 |
| FN3K | HEXDC | 1 | + | + | chr17 | chr17 | 80693653 | 80398873 |
| FOXN3 | CDKL1 | 1 | − | − | chr14 | chr14 | 89878278 | 50796899 |
| FRMD3 | BRD4 | 1 | − | − | chr9 | chr19 | 85987828 | 15365073 |
| FRMD4B | OXCT1 | 1 | − | − | chr3 | chr5 | 69265414 | 41801172 |
| FRMD4B | OXCT1 | 1 | − | − | chr3 | chr5 | 69267473 | 41801172 |
| FRMD4B | OXCT1 | 1 | − | − | chr3 | chr5 | 69271009 | 41801172 |
| FRMD6 | LINC00640 | 1 | + | + | chr14 | chr14 | 51956138 | 51800111 |
| FRS2 | ARHGEF25 | 1 | + | + | chr12 | chr12 | 69864310 | 58007047 |
| FRS2 | ARHGEF25 | 1 | + | + | chr12 | chr12 | 69864310 | 58007223 |
| FRS2 | DTX3 | 1 | + | + | chr12 | chr12 | 69864310 | 58002303 |
| GAK | TMEM175 | 1 | − | + | chr4 | chr4 | 925831 | 941497 |
| GALNT13 | SMYD1 | 1 | + | + | chr2 | chr2 | 154997018 | 88383835 |
| GID4 | LRRC48 | 1 | + | + | chr17 | chr17 | 17943216 | 17907677 |
| GIGYF2 | ECEL1 | 1 | + | − | chr2 | chr2 | 233562102 | 233345185 |
| GIGYF2 | ECEL1 | 1 | + | − | chr2 | chr2 | 233562102 | 233345523 |
| GIGYF2 | ECEL1 | 1 | + | − | chr2 | chr2 | 233562102 | 233345866 |
| GLE1 | ODF2 | 1 | + | + | chr9 | chr9 | 131267183 | 131254705 |
| GOLPH3 | SLC6A19 | 1 | − | + | chr5 | chr5 | 32173916 | 1219018 |
| GPATCH8 | MYO1D | 1 | − | − | chr17 | chr17 | 42580694 | 30821933 |
| GPR110 | TRERF1 | 1 | − | − | chr6 | chr6 | 46993590 | 42204149 |
| GPR137C | FERMT2 | 1 | + | − | chr14 | chr14 | 53020309 | 53331571 |
| GPSM2 | SRG7 | 1 | + | + | chr1 | chr1 | 109445856 | 109400780 |
| GRB2 | POMGNT1 | 1 | − | − | chr17 | chr1 | 73401570 | 46663543 |
| GTF2E2 | RBPMS | 1 | − | + | chr8 | chr8 | 30510950 | 30402011 |
| GTF2H3 | EIF2B1 | 1 | + | − | chr12 | chr12 | 124118419 | 124115080 |
| GTF2I | GTF2IRD1 | 1 | + | + | chr7 | chr7 | 74072394 | 73960074 |
| GTF2I | GTF2IRD1 | 1 | + | + | chr7 | chr7 | 74120764 | 74004180 |
| GTF2IRD1 | YWHAG | 1 | + | + | chr7 | chr7 | 73868506 | 75959550 |
| GTF3C2 | SNX17 | 1 | − | + | chr2 | chr2 | 27550904 | 27598373 |
| GTPBP2 | VEGFA | 1 | − | + | chr6 | chr6 | 43592247 | 43752278 |
| GTSE1 | ATXN10 | 1 | + | + | chr22 | chr22 | 46693376 | 46202839 |
| HARBI1 | PTPRS | 1 | − | − | chr11 | chr19 | 46637118 | 5246056 |
| HDAC1 | SERINC2 | 1 | + | + | chr1 | chr1 | 32768334 | 31883232 |
| HDGF | RRNAD1 | 1 | − | + | chr1 | chr1 | 156714800 | 156706424 |
| HIBADH | C7orf10 | 1 | − | − | chr7 | chr7 | 27668990 | 40723655 |
| HIBADH | C7orf10 | 1 | − | − | chr7 | chr7 | 27668990 | 40789033 |
| HIF1A | C14orf37 | 1 | + | − | chr14 | chr14 | 62162557 | 58606132 |
| HINT3 | NCOA7 | 1 | − | + | chr6 | chr6 | 126278324 | 126176166 |
| HIPK3 | TOLLIP | 1 | + | + | chr11 | chr11 | 33279435 | 1317024 |
| HIRA | NSMCE2 | 1 | − | + | chr22 | chr8 | 19418963 | 126369461 |
| HLCS | KIAA1755 | 1 | − | − | chr21 | chr20 | 38269160 | 36856642 |
| HLCS | LINC00478 | 1 | − | + | chr21 | chr21 | 38334336 | 17859810 |
| HMGA2 | ARFGAP2 | 1 | + | − | chr12 | chr11 | 66219161 | 47193884 |

TABLE 1-continued

Chimeras Unveiled by sMACHETE

| 5'-Gene (gene1) | 3'-Gene (gene2) | Number of Samples Found to Have Chimera | strand 1 | strand 2 | chr1 | chr2 | pos1 | pos2 |
|---|---|---|---|---|---|---|---|---|
| HNRNPUL1 | ACTN4 | 1 | + | + | chr19 | chr19 | 41787180 | 39191240 |
| HOMER3 | TRIP10 | 1 | − | + | chr19 | chr19 | 19042134 | 6749945 |
| HOOK2 | MAST1 | 1 | − | + | chr19 | chr19 | 12881746 | 12958662 |
| HOOK3 | TM2D2 | 1 | + | − | chr8 | chr8 | 42761401 | 38853212 |
| HOXC10 | WIBG | 1 | + | − | chr12 | chr12 | 54379794 | 56297264 |
| HPCAL1 | CDKL4 | 1 | + | − | chr2 | chr2 | 10443303 | 39417643 |
| HSP90AB1 | CAPN11 | 1 | + | + | chr6 | chr6 | 44214932 | 44134495 |
| HTT | LOC402160 | 1 | + | + | chr4 | chr4 | 3216938 | 2460450 |
| IFNGR2 | TMEM50B | 1 | + | − | chr21 | chr21 | 34799339 | 34805109 |
| IFT140 | TELO2 | 1 | − | + | chr16 | chr16 | 1568217 | 1549232 |
| IGSF8 | IFI6 | 1 | − | − | chr1 | chr1 | 160068199 | 27995857 |
| IKBKB | ANK1 | 1 | + | + | chr8 | chr8 | 42129723 | 41591587 |
| IL12RB2 | PDE4B | 1 | + | + | chr1 | chr1 | 67796493 | 66837996 |
| IL32 | TNFRSF12A | 1 | + | + | chr16 | chr16 | 3115827 | 3071556 |
| IMMP2L | DYNC1I1 | 1 | − | + | chr7 | chr7 | 110526649 | 95657487 |
| IMPA2 | GNAL | 1 | + | + | chr18 | chr18 | 12014372 | 11752852 |
| INADL | DYNC2H1 | 1 | + | + | chr1 | chr11 | 62483619 | 103151077 |
| INADL | NFIA | 1 | + | + | chr1 | chr1 | 62241006 | 61920975 |
| INO80 | THSD4 | 1 | − | + | chr15 | chr15 | 41313098 | 72020888 |
| INPP5A | LRRC27 | 1 | + | + | chr10 | chr10 | 134351675 | 134174961 |
| INTS1 | GET4 | 1 | − | + | chr7 | chr7 | 1510482 | 930565 |
| IPO11 | KIF2A | 1 | + | + | chr5 | chr5 | 61733244 | 61669514 |
| IPO8 | CDH13 | 1 | − | + | chr12 | chr16 | 30809618 | 83205127 |
| IQGAP1 | SEMA4B | 1 | + | + | chr15 | chr15 | 90934105 | 90760671 |
| IRAK2 | MTMR14 | 1 | + | + | chr3 | chr3 | 10261473 | 9703951 |
| ITCH | CBFA2T2 | 1 | + | + | chr20 | chr20 | 32981687 | 32232153 |
| ITGA3 | MIEN1 | 1 | + | − | chr17 | chr17 | 48134009 | 37886544 |
| ITGA9 | POPDC2 | 1 | + | − | chr3 | chr3 | 37560845 | 119361408 |
| ITPA | BCAS1 | 1 | + | + | chr20 | chr20 | 3190263 | 52612589 |
| ITPKC | SPTBN4 | 1 | + | + | chr19 | chr19 | 41231344 | 41071329 |
| ITPR1 | SETMAR | 1 | + | + | chr3 | chr3 | 4859926 | 4354582 |
| JAK1 | HSD11B1 | 1 | − | + | chr1 | chr1 | 65432016 | 209878262 |
| JAZF1 | CPT1C | 1 | − | + | chr7 | chr19 | 28220082 | 50211980 |
| JAZF1 | CPT1C | 1 | − | + | chr7 | chr19 | 28220082 | 50216229 |
| JKAMP | DAAM1 | 1 | + | + | chr14 | chr14 | 59953522 | 59806792 |
| KANSL1 | LAYN | 1 | − | + | chr17 | chr11 | 44127899 | 111414648 |
| KANSL1 | LAYN | 1 | − | + | chr17 | chr11 | 44127899 | 111425286 |
| KAT6A | CREBBP | 1 | − | − | chr8 | chr16 | 41794774 | 3901010 |
| KCNMA1 | RPS24 | 1 | − | + | chr10 | chr10 | 79163620 | 79795110 |
| KCTD3 | CENPF | 1 | + | + | chr1 | chr1 | 215760028 | 214836934 |
| KDM2B | KSR2 | 1 | − | − | chr12 | chr12 | 121986782 | 118298236 |
| KDM4B | SNTG1 | 1 | + | + | chr19 | chr8 | 5047680 | 51085121 |
| KDM4C | DMRT3 | 1 | + | + | chr9 | chr9 | 6814745 | 990041 |
| KIAA0101 | TRIP4 | 1 | − | + | chr15 | chr15 | 64673157 | 64698529 |
| KIAA0907 | CD276 | 1 | − | + | chr1 | chr15 | 155887290 | 74001989 |
| KIAA1199 | ZYX | 1 | + | + | chr15 | chr7 | 81224380 | 143078650 |
| KIAA1199 | ZYX | 1 | + | + | chr15 | chr7 | 81224380 | 143078653 |
| KIAA1199 | ZYX | 1 | + | + | chr15 | chr7 | 81224380 | 143085312 |
| KIAA1598 | YTHDF1 | 1 | − | − | chr10 | chr20 | 118764533 | 61828086 |
| KIAA1614 | F11R | 1 | + | + | chr1 | chr1 | 180897709 | 160970138 |
| KIF1B | UBE4B | 1 | + | + | chr1 | chr1 | 10292492 | 10238702 |
| KIF26B | C1orf101 | 1 | + | + | chr1 | chr1 | 245530669 | 244773542 |
| KIF5C | EPC2 | 1 | + | + | chr2 | chr2 | 149679796 | 149539213 |
| KLHL3 | C16orf45 | 1 | − | − | chr5 | chr16 | 137071322 | 15609162 |
| KPNA5 | RWDD1 | 1 | + | + | chr6 | chr6 | 117013319 | 116901458 |
| KRT7 | LINC00592 | 1 | + | + | chr12 | chr12 | 52632559 | 52617230 |
| LANCL2 | CPM | 1 | + | − | chr7 | chr12 | 55433922 | 69252851 |
| LAPTM4B | MTDH | 1 | + | + | chr8 | chr8 | 98788336 | 98736828 |
| LCOR | C10orf131 | 1 | + | + | chr10 | chr10 | 98592156 | 97681773 |
| LETM1 | WHSC1 | 1 | − | + | chr4 | chr4 | 1823908 | 1902353 |
| LIMK1 | GNAT3 | 1 | + | − | chr7 | chr7 | 73530288 | 80123963 |
| LIMK1 | SHFM1 | 1 | + | + | chr7 | chr7 | 73523366 | 96324203 |
| LINC00265 | RALA | 1 | + | + | chr7 | chr7 | 39773643 | 39745722 |
| LINC00665 | AXL | 1 | − | + | chr19 | chr19 | 36806859 | 41763398 |
| LINC00665 | CDH4 | 1 | − | + | chr19 | chr20 | 36821155 | 60318619 |
| LMNA | CCT3 | 1 | + | − | chr1 | chr1 | 156052975 | 156294880 |
| LOC100505549 | NARS | 1 | + | − | chr18 | chr18 | 55297750 | 55283207 |
| LOC100505633 | IFI16 | 1 | + | + | chr1 | chr1 | 159931195 | 159002314 |
| LOC100506713 | MED29 | 1 | − | + | chr17 | chr19 | 6915515 | 39883104 |
| LOC100506844 | SRRM4 | 1 | − | + | chr12 | chr12 | 58329253 | 119583186 |

TABLE 1-continued

Chimeras Unveiled by sMACHETE

| 5'-Gene (gene1) | 3'-Gene (gene2) | Number of Samples Found to Have Chimera | strand 1 | strand 2 | Junction Locus Data |||| 
|---|---|---|---|---|---|---|---|---|
| | | | | | chr1 | chr2 | pos1 | pos2 |
| LOC100506844 | SRRM4 | 1 | − | + | chr12 | chr12 | 58329253 | 119588822 |
| LOC344887 | ZNF639 | 1 | + | + | chr3 | chr3 | 185693145 | 179047406 |
| LOC728323 | THAP4 | 1 | + | − | chr2 | chr2 | 243030952 | 242545888 |
| LPP | CASR | 1 | + | + | chr3 | chr3 | 188202492 | 121972795 |
| LPP | CASR | 1 | + | + | chr3 | chr3 | 188202492 | 121980375 |
| LRIG1 | SLC25A26 | 1 | − | + | chr3 | chr3 | 66436405 | 66419902 |
| LRP1 | ETV6 | 1 | + | + | chr12 | chr12 | 57539273 | 12037379 |
| LRP1 | XPO5 | 1 | + | − | chr12 | chr6 | 57539273 | 43530083 |
| LRRC27 | PITPNC1 | 1 | + | + | chr10 | chr17 | 134169390 | 65528918 |
| LRRC37BP1 | DNM1L | 1 | + | + | chr17 | chr12 | 28934683 | 32895523 |
| LRRC69 | OTUD6B | 1 | + | + | chr8 | chr8 | 92145533 | 92083366 |
| LRRCC1 | ZC2HC1A | 1 | + | + | chr8 | chr8 | 86025334 | 79627456 |
| LRRK1 | ASB7 | 1 | + | + | chr15 | chr15 | 101569437 | 101188528 |
| LSR | FXYD3 | 1 | + | + | chr19 | chr19 | 35749967 | 35613822 |
| LUC7L3 | IKZF3 | 1 | + | − | chr17 | chr17 | 48797192 | 37949186 |
| MAML3 | LINC00616 | 1 | − | − | chr4 | chr4 | 141074014 | 139050664 |
| MAN1A2 | TTF2 | 1 | + | + | chr1 | chr1 | 117984947 | 117616283 |
| MAN1A2 | VANGL1 | 1 | + | + | chr1 | chr1 | 117984947 | 116224985 |
| MAP3K3 | DCAF7 | 1 | + | + | chr17 | chr17 | 61744420 | 61671565 |
| MAPK9 | UBL7 | 1 | − | − | chr5 | chr15 | 179718848 | 74738568 |
| MAPK9 | UBL7 | 1 | − | − | chr5 | chr15 | 179718848 | 74744719 |
| MAPK9 | UBL7 | 1 | − | − | chr5 | chr15 | 179718848 | 74749012 |
| 6-Mar | UVRAG | 1 | + | + | chr5 | chr11 | 10411649 | 75826968 |
| 9-Mar | CD2AP | 1 | + | + | chr12 | chr6 | 58152083 | 47512342 |
| MDM2 | EGFR | 1 | + | + | chr12 | chr7 | 69203072 | 55231426 |
| MDM2 | PPM1H | 1 | + | − | chr12 | chr12 | 69230529 | 63195940 |
| MDM2 | TSPAN31 | 1 | + | + | chr12 | chr12 | 69222711 | 58140372 |
| MED1 | TMPRSS9 | 1 | − | + | chr17 | chr19 | 37607291 | 2401973 |
| MED15 | COMT | 1 | + | + | chr22 | chr22 | 20891491 | 19948722 |
| MED23 | ANO2 | 1 | − | − | chr6 | chr12 | 131908849 | 5841796 |
| MEGF9 | LPPR1 | 1 | − | + | chr9 | chr9 | 123476036 | 103947732 |
| METTL21B | CYP27B1 | 1 | + | − | chr12 | chr12 | 58166911 | 58159980 |
| METTL21B | INHBE | 1 | + | + | chr12 | chr12 | 58166911 | 57849877 |
| MGRN1 | MSI2 | 1 | + | + | chr16 | chr17 | 4733933 | 55756910 |
| MIEN1 | WIPF2 | 1 | − | + | chr17 | chr17 | 37886447 | 38412643 |
| MKL2 | SHISA9 | 1 | + | + | chr16 | chr16 | 14173211 | 13297251 |
| MLL | ELL | 1 | + | − | chr11 | chr19 | 118355690 | 18569139 |
| MLL | MLLT10 | 1 | + | + | chr11 | chr10 | 118353210 | 21875223 |
| MLL | MLLT4 | 1 | + | + | chr11 | chr6 | 118353210 | 168265231 |
| MLL3 | CLIP2 | 1 | − | + | chr7 | chr7 | 151871216 | 73811404 |
| MLL3 | DNAH11 | 1 | − | + | chr7 | chr7 | 152007051 | 21856085 |
| MLLT10 | PICALM | 1 | + | − | chr10 | chr11 | 21906136 | 85670103 |
| MPG | NPRL3 | 1 | + | − | chr16 | chr16 | 129699 | 136869 |
| MRAP2 | CYB5R4 | 1 | + | + | chr6 | chr6 | 84772711 | 84665017 |
| MRPL21 | LRP5 | 1 | − | + | chr11 | chr11 | 68663983 | 68115315 |
| MSI2 | CCDC178 | 1 | + | − | chr17 | chr18 | 55339553 | 31020045 |
| MST1R | FXYD3 | 1 | − | + | chr3 | chr19 | 49935484 | 35613669 |
| MTA1 | INF2 | 1 | + | + | chr14 | chr14 | 105905076 | 105173247 |
| MTM1 | MAMLD1 | 1 | + | + | chrX | chrX | 149767150 | 149671544 |
| MTMR3 | NF2 | 1 | + | + | chr22 | chr22 | 30279348 | 30067815 |
| MX2 | FAM3B | 1 | + | + | chr21 | chr21 | 42752078 | 42716403 |
| MYH9 | EMID1 | 1 | − | + | chr22 | chr22 | 36744949 | 29610915 |
| MYL6 | KRT7 | 1 | + | + | chr12 | chr12 | 56554104 | 52642375 |
| MYO18B | UBE2R2 | 1 | + | + | chr22 | chr9 | 26228964 | 33911962 |
| MYO18B | UBE2R2 | 1 | + | + | chr22 | chr9 | 26228964 | 33917016 |
| MYO1D | TMIGD1 | 1 | − | − | chr17 | chr17 | 31203796 | 28656547 |
| MYO9B | TECR | 1 | + | + | chr19 | chr19 | 17186684 | 14673337 |
| NAA25 | WSCD2 | 1 | − | + | chr12 | chr12 | 112546520 | 108620767 |
| NAA60 | IL32 | 1 | + | + | chr16 | chr16 | 3498540 | 3115782 |
| NAA60 | IL32 | 1 | + | + | chr16 | chr16 | 3498540 | 3115785 |
| NAA60 | IL32 | 1 | + | + | chr16 | chr16 | 3508181 | 3115782 |
| NAB1 | MFSD6 | 1 | + | + | chr2 | chr2 | 191537878 | 191353383 |
| NARF | HEXDC | 1 | + | + | chr17 | chr17 | 80426772 | 80397507 |
| NAT8L | DBNDD1 | 1 | + | − | chr4 | chr16 | 2062889 | 90075838 |
| NCEH1 | BCL2L1 | 1 | − | − | chr3 | chr20 | 172428637 | 30253889 |
| NCF2 | SMG7 | 1 | − | + | chr1 | chr1 | 183529231 | 183510119 |
| NCK2 | MRPS9 | 1 | + | + | chr2 | chr2 | 106361595 | 105696441 |
| NCK2 | MRPS9 | 1 | + | + | chr2 | chr2 | 106361595 | 105705442 |
| NCOA4 | C10orf25 | 1 | + | − | chr10 | chr10 | 51565296 | 45495864 |
| NDRG1 | OC90 | 1 | − | − | chr8 | chr8 | 134292475 | 133037023 |

TABLE 1-continued

Chimeras Unveiled by sMACHETE

| 5'-Gene (gene1) | 3'-Gene (gene2) | Number of Samples Found to Have Chimera | strand 1 | strand 2 | chr1 | chr2 | pos1 | pos2 |
|---|---|---|---|---|---|---|---|---|
| NDUFAF5 | ESF1 | 1 | + | − | chr20 | chr20 | 13769298 | 13756916 |
| NDUFAF5 | ESF1 | 1 | + | − | chr20 | chr20 | 13775587 | 13756916 |
| NEDD9 | FAM178B | 1 | − | − | chr6 | chr2 | 11188451 | 97544230 |
| NF1 | ADAP2 | 1 | + | + | chr17 | chr17 | 29422387 | 29281496 |
| NFASC | LRRN2 | 1 | + | − | chr1 | chr1 | 204797910 | 204589346 |
| NFASC | SOX13 | 1 | + | + | chr1 | chr1 | 204797910 | 204082043 |
| NFASC | SOX13 | 1 | + | + | chr1 | chr1 | 204797910 | 204083449 |
| NFIC | IL4I1 | 1 | + | − | chr19 | chr19 | 3382241 | 50394364 |
| NFRKB | CRTAM | 1 | − | + | chr11 | chr11 | 129746616 | 122720776 |
| NOTCH3 | HOXD11 | 1 | − | + | chr19 | chr2 | 15308311 | 176973635 |
| NPAS3 | AKAP6 | 1 | + | + | chr14 | chr14 | 33684632 | 33147517 |
| NR2C2AP | MAP1S | 1 | − | + | chr19 | chr19 | 19313600 | 17835858 |
| NR3C2 | ARHGAP10 | 1 | − | + | chr4 | chr4 | 149035255 | 148993144 |
| NRF1 | STRIP2 | 1 | + | + | chr7 | chr7 | 129251665 | 129091454 |
| NSD1 | CDH23 | 1 | + | + | chr5 | chr10 | 176563031 | 73434869 |
| NUAK1 | C12orf65 | 1 | − | + | chr12 | chr12 | 106477642 | 123738194 |
| NUP107 | CYP27B1 | 1 | + | − | chr12 | chr12 | 69129124 | 58157959 |
| NUP107 | 9-Mar | 1 | + | + | chr12 | chr12 | 69121169 | 58151891 |
| NUPL2 | EPCAM | 1 | + | + | chr7 | chr2 | 23221825 | 47604153 |
| OCEL1 | MYO9B | 1 | + | + | chr19 | chr19 | 17338008 | 17312735 |
| OR51E2 | RRM1 | 1 | − | + | chr11 | chr11 | 4718883 | 4123223 |
| ORAI2 | SLC47A2 | 1 | + | − | chr7 | chr17 | 102079628 | 19584983 |
| OVGP1 | GNB2L1 | 1 | − | − | chr1 | chr5 | 111965549 | 180664042 |
| PACSIN2 | NUPL2 | 1 | − | + | chr22 | chr7 | 43308027 | 23224689 |
| PARD3B | WWOX | 1 | + | + | chr2 | chr16 | 205990461 | 79245505 |
| PARD6B | LOC284751 | 1 | + | + | chr20 | chr20 | 49354616 | 48914693 |
| PARD6B | LOC284751 | 1 | + | + | chr20 | chr20 | 49354616 | 48928342 |
| PARD6B | PTPN1 | 1 | + | + | chr20 | chr20 | 49348389 | 49177900 |
| PARD6B | PTPN1 | 1 | + | + | chr20 | chr20 | 49354616 | 49177900 |
| PARG | NCAM2 | 1 | − | + | chr10 | chr21 | 51040849 | 22906858 |
| PCGF3 | MYL5 | 1 | + | + | chr4 | chr4 | 724899 | 675682 |
| PCGF3 | PDE6B | 1 | + | + | chr4 | chr4 | 699759 | 647641 |
| PCMTD1 | MRPL15 | 1 | − | + | chr8 | chr8 | 52811490 | 55049071 |
| PCNXL3 | EHBP1L1 | 1 | + | + | chr11 | chr11 | 65401827 | 65346549 |
| PDE4D | FGF14 | 1 | − | − | chr5 | chr13 | 59783769 | 102379160 |
| PDE7A | KIAA1217 | 1 | − | + | chr8 | chr10 | 66753606 | 24721924 |
| PDE7A | TRIM55 | 1 | − | − | chr8 | chr8 | 66753606 | 67061880 |
| PDGFRA | SCFD2 | 1 | + | − | chr4 | chr4 | 55095582 | 54140168 |
| PEAK1 | TM9SF3 | 1 | − | − | chr15 | chr10 | 77712348 | 98292947 |
| PER3 | ASAP3 | 1 | + | + | chr1 | chr1 | 7848306 | 23782687 |
| PGM2L1 | C1orf61 | 1 | − | − | chr11 | chr1 | 74079537 | 156384545 |
| PHAX | ALDH7A1 | 1 | + | − | chr5 | chr5 | 125936750 | 125929096 |
| PHF20 | ADNP | 1 | + | + | chr20 | chr20 | 34389527 | 49511049 |
| PHF21A | CAMK1D | 1 | − | + | chr11 | chr10 | 46098305 | 12811672 |
| PHIP | MYO6 | 1 | − | + | chr6 | chr6 | 79770195 | 76527218 |
| PIAS4 | GLYATL2 | 1 | + | − | chr19 | chr11 | 4029034 | 58611997 |
| PIGF | CCDC40 | 1 | − | + | chr2 | chr17 | 46819614 | 78069062 |
| PIGG | SPINK2 | 1 | + | − | chr4 | chr4 | 502759 | 57676350 |
| PILRB | SLC22A20 | 1 | + | + | chr7 | chr11 | 99950893 | 65009461 |
| PIM3 | CRELD2 | 1 | + | + | chr22 | chr22 | 50355459 | 50320903 |
| PIP5K1C | TJP3 | 1 | − | + | chr19 | chr19 | 3700295 | 3731933 |
| PLCH1 | MYOM2 | 1 | − | + | chr3 | chr8 | 155421935 | 2088646 |
| PLXND1 | NEK11 | 1 | − | + | chr3 | chr3 | 129304795 | 131068401 |
| PLXND1 | NEK11 | 1 | − | + | chr3 | chr3 | 129308194 | 131068401 |
| PNPLA2 | IGF2 | 1 | + | + | chr11 | chr11 | 818958 | 2156759 |
| POLA1 | PDK3 | 1 | + | + | chrX | chrX | 24722586 | 24512859 |
| POLR2A | FBN3 | 1 | + | − | chr17 | chr19 | 7388176 | 8156474 |
| PPFIA1 | SLC39A11 | 1 | − | + | chr11 | chr17 | 70172924 | 71080985 |
| PPFIA1 | SLC39A11 | 1 | − | + | chr11 | chr17 | 70172924 | 71084914 |
| PPM1H | FAM19A2 | 1 | − | − | chr12 | chr12 | 63328272 | 62104198 |
| PPM1H | KIAA1467 | 1 | − | + | chr12 | chr12 | 63131282 | 13214509 |
| PPP1CB | PLB1 | 1 | + | + | chr2 | chr2 | 28975042 | 28808628 |
| PPP1CB | PLB1 | 1 | + | + | chr2 | chr2 | 29006844 | 28812542 |
| PPP1R12C | C19orf33 | 1 | − | + | chr19 | chr19 | 55623835 | 38795015 |
| PPP1R37 | CLASRP | 1 | + | + | chr19 | chr19 | 45596785 | 45570595 |
| PPP1R37 | MRPL38 | 1 | + | + | chr19 | chr17 | 45596785 | 73898235 |
| PPP2CA | CDH3 | 1 | − | + | chr5 | chr16 | 133561451 | 68710288 |
| PPP2R3A | RAB7A | 1 | + | + | chr3 | chr3 | 135789394 | 128514203 |
| PPP3R1 | SPATS2L | 1 | − | + | chr2 | chr2 | 68444224 | 201305372 |
| PPP6C | C11orf84 | 1 | − | + | chr9 | chr11 | 127933364 | 63594400 |

TABLE 1-continued

Chimeras Unveiled by sMACHETE

| 5'-Gene (gene1) | 3'-Gene (gene2) | Number of Samples Found to Have Chimera | strand 1 | strand 2 | chr1 | chr2 | pos1 | pos2 |
| --- | --- | --- | --- | --- | --- | --- | --- | --- |
| PPT1 | CAP1 | 1 | − | + | chr1 | chr1 | 40544232 | 40527407 |
| PPT1 | CAP1 | 1 | − | + | chr1 | chr1 | 40544232 | 40529899 |
| PRKAG2 | CCDC132 | 1 | − | + | chr7 | chr7 | 151573592 | 92970739 |
| PRPSAP2 | EEPD1 | 1 | + | + | chr17 | chr7 | 18775962 | 36320724 |
| PRUNE | SETDB1 | 1 | + | + | chr1 | chr1 | 150981147 | 150933039 |
| PSMB3 | CISD3 | 1 | + | + | chr17 | chr17 | 36918758 | 36887573 |
| PSMC4 | RFC3 | 1 | + | + | chr19 | chr13 | 40480735 | 34540224 |
| PSMD1 | DNER | 1 | + | − | chr2 | chr2 | 231945028 | 230377652 |
| PSORS1C1 | MUC22 | 1 | + | + | chr6 | chr6 | 31082668 | 31002449 |
| PTK2 | PPP2R5E | 1 | − | − | chr8 | chr14 | 141900642 | 63920603 |
| PTPN9 | ASH1L | 1 | − | − | chr15 | chr1 | 75871055 | 155324421 |
| PTPRG | BRD8 | 1 | + | − | chr3 | chr5 | 61734656 | 137481567 |
| PWWP2A | IQGAP2 | 1 | − | + | chr5 | chr5 | 159545812 | 75858221 |
| PXDNL | MSI2 | 1 | − | + | chr8 | chr17 | 52721741 | 55729460 |
| PXK | RPP14 | 1 | + | + | chr3 | chr3 | 58318817 | 58296036 |
| R3HDM2 | XRCC6BP1 | 1 | − | + | chr12 | chr12 | 57660514 | 58339411 |
| RAB21 | FRS2 | 1 | + | + | chr12 | chr12 | 72167802 | 69955960 |
| RAB3D | SMARCA4 | 1 | − | + | chr19 | chr19 | 11446123 | 11091453 |
| RAB3IP | ERBB3 | 1 | + | + | chr12 | chr12 | 70150443 | 56477535 |
| RAB7A | KBTBD12 | 1 | + | + | chr3 | chr3 | 128445202 | 127648976 |
| RABGGTB | ACADM | 1 | + | + | chr1 | chr1 | 76255041 | 76205665 |
| RAD51B | MPP5 | 1 | + | + | chr14 | chr14 | 68353921 | 67770239 |
| RAF1 | GXYLT2 | 1 | − | + | chr3 | chr3 | 12705312 | 72957518 |
| RAP1GAP2 | TEKT1 | 1 | + | − | chr17 | chr17 | 2703844 | 6719281 |
| RAP1GAP2 | TEKT1 | 1 | + | − | chr17 | chr17 | 2703844 | 6722677 |
| RARA | CDC6 | 1 | + | + | chr17 | chr17 | 38465538 | 38445660 |
| RBCK1 | MYO18A | 1 | + | − | chr20 | chr17 | 389423 | 27401932 |
| RBM47 | LIMCH1 | 1 | − | + | chr4 | chr4 | 40631413 | 41640949 |
| RBM5 | RBM6 | 1 | + | + | chr3 | chr3 | 50148203 | 50112634 |
| REC8 | RNF31 | 1 | + | + | chr14 | chr14 | 24649112 | 24629448 |
| RERE | MFSD2A | 1 | − | + | chr1 | chr1 | 8482787 | 40424373 |
| RERE | SLC45A1 | 1 | − | + | chr1 | chr1 | 8601273 | 8395497 |
| RGL1 | LAMC2 | 1 | + | + | chr1 | chr1 | 183891470 | 183194743 |
| RHOG | STIM1 | 1 | − | + | chr11 | chr11 | 3862124 | 3988782 |
| RIC8B | RFX4 | 1 | + | + | chr12 | chr12 | 107219598 | 107075771 |
| RIMS4 | AKAP10 | 1 | − | − | chr20 | chr17 | 43438816 | 19871774 |
| RIPK1 | NQO2 | 1 | + | + | chr6 | chr6 | 3089891 | 3006702 |
| RNF115 | HFE2 | 1 | + | + | chr1 | chr1 | 145663367 | 145415279 |
| RNF40 | C16orf93 | 1 | + | − | chr16 | chr16 | 30774880 | 30768975 |
| RPS6KC1 | FLVCR1 | 1 | + | + | chr1 | chr1 | 213224851 | 213068328 |
| RPS6KC1 | FLVCR1 | 1 | + | + | chr1 | chr1 | 213224851 | 213068558 |
| RPS6KC1 | LYST | 1 | + | − | chr1 | chr1 | 213303232 | 235840919 |
| RPTOR | GAA | 1 | + | + | chr17 | chr17 | 78811797 | 78078354 |
| RPUSD3 | OGG1 | 1 | − | + | chr3 | chr3 | 9883667 | 9792629 |
| RREB1 | EEF1E1 | 1 | + | − | chr6 | chr6 | 7108293 | 8097700 |
| RUNX1 | MECOM | 1 | − | − | chr21 | chr3 | 36206707 | 169099312 |
| RUNX1T1 | RUNX1 | 1 | − | − | chr8 | chr21 | 93074774 | 36231875 |
| SCAF1 | TRAPPC6A | 1 | + | + | chr19 | chr19 | 50150087 | 45668228 |
| SCAF1 | TRAPPC6A | 1 | + | + | chr19 | chr19 | 50150087 | 45668452 |
| SCAI | TOX3 | 1 | − | − | chr9 | chr16 | 127904912 | 52484458 |
| SCARB1 | SFSWAP | 1 | − | + | chr12 | chr12 | 125348141 | 132209950 |
| SDK2 | RAB37 | 1 | − | + | chr17 | chr17 | 71375316 | 72725395 |
| SEC61G | EGFR | 1 | − | + | chr7 | chr7 | 54825188 | 55224226 |
| SEH1L | IMPA2 | 1 | + | + | chr18 | chr18 | 12951904 | 11999053 |
| SEPN1 | TMEM59 | 1 | + | − | chr1 | chr1 | 26139283 | 54506510 |
| SERINC5 | FLJ41200 | 1 | − | − | chr5 | chr9 | 79462206 | 13416544 |
| SET | GLE1 | 1 | + | + | chr9 | chr9 | 131447492 | 131284947 |
| SETD1B | KDM2B | 1 | + | − | chr12 | chr12 | 122248741 | 122012498 |
| SETD2 | CCRL2 | 1 | − | − | chr3 | chr3 | 47139445 | 46449559 |
| SFMBT1 | GNL3 | 1 | − | + | chr3 | chr3 | 53079832 | 52720785 |
| SGPL1 | ADAMTS14 | 1 | + | + | chr10 | chr10 | 72576636 | 72492010 |
| SH2B3 | FBXO21 | 1 | + | − | chr12 | chr12 | 111844081 | 117584082 |
| SH3GL1 | ANKRD24 | 1 | − | + | chr19 | chr19 | 4400321 | 4219588 |
| SHB | LINGO2 | 1 | − | − | chr9 | chr9 | 38016008 | 27950704 |
| SIPA1L3 | ETHE1 | 1 | + | − | chr19 | chr19 | 38655546 | 44015718 |
| SKAP1 | PSMD11 | 1 | − | + | chr17 | chr17 | 46423267 | 30773963 |
| SKIL | GPR160 | 1 | + | + | chr3 | chr3 | 170079217 | 169797562 |
| SKIV2L2 | U5P28 | 1 | + | − | chr5 | chr11 | 54662703 | 113679976 |
| SLC16A10 | NME7 | 1 | + | − | chr6 | chr1 | 111498868 | 169102055 |
| SLC22A15 | ANO1 | 1 | + | + | chr1 | chr11 | 116580009 | 69995816 |

TABLE 1-continued

Chimeras Unveiled by sMACHETE

| 5'-Gene (gene1) | 3'-Gene (gene2) | Number of Samples Found to Have Chimera | strand 1 | strand 2 | chr1 | chr2 | pos1 | pos2 |
|---|---|---|---|---|---|---|---|---|
| SLC22A3 | PVT1 | 1 | + | + | chr6 | chr8 | 160769880 | 129108764 |
| SLC22A4 | PDLIM4 | 1 | + | + | chr5 | chr5 | 131630702 | 131598302 |
| SLC2A8 | GARNL3 | 1 | + | + | chr9 | chr9 | 130167270 | 130151183 |
| SLC30A4 | PDE2A | 1 | − | − | chr15 | chr11 | 45803336 | 72342183 |
| SLC30A7 | RTCA | 1 | + | + | chr1 | chr1 | 101387397 | 100750784 |
| SLC35E3 | OS9 | 1 | + | + | chr12 | chr12 | 69145970 | 58109543 |
| SLC37A1 | ABCG1 | 1 | + | + | chr21 | chr21 | 43945967 | 43702384 |
| SLC39A6 | TBX15 | 1 | − | − | chr18 | chr1 | 33709077 | 119441748 |
| SLC39A9 | BCL2L13 | 1 | + | + | chr14 | chr22 | 69908983 | 18138428 |
| SLC4A1AP | GPN1 | 1 | + | + | chr2 | chr2 | 27892254 | 27870703 |
| SLFN5 | TBC1D15 | 1 | + | + | chr17 | chr12 | 33570162 | 72307606 |
| SLPI | EYA2 | 1 | − | + | chr20 | chr20 | 43881643 | 45801355 |
| SLX4IP | PLCB1 | 1 | + | + | chr20 | chr20 | 10582467 | 8862269 |
| SMAD3 | SMAD6 | 1 | + | + | chr15 | chr15 | 67358698 | 67073335 |
| SMARCA4 | CARM1 | 1 | + | + | chr19 | chr19 | 11071850 | 11015627 |
| SMARCA4 | CARM1 | 1 | + | + | chr19 | chr19 | 11071850 | 11022860 |
| SMARCA4 | DNM2 | 1 | + | + | chr19 | chr19 | 11136184 | 10930656 |
| SMARCA4 | DNM2 | 1 | + | + | chr19 | chr19 | 11138626 | 10887794 |
| SMCHD1 | NDC80 | 1 | + | + | chr18 | chr18 | 2732490 | 2599018 |
| SMS | CNKSR2 | 1 | + | + | chrX | chrX | 21958991 | 21670424 |
| SNRNP200 | CIAO1 | 1 | − | + | chr2 | chr2 | 96948939 | 96935006 |
| SNX27 | CDKN3 | 1 | + | + | chr1 | chr14 | 151584988 | 54882617 |
| SOCS7 | PLXDC1 | 1 | + | − | chr17 | chr17 | 36533668 | 37265644 |
| SORBS2 | OS9 | 1 | − | + | chr4 | chr12 | 186578578 | 58109543 |
| SORL1 | CEP164 | 1 | + | + | chr11 | chr11 | 121367758 | 117251330 |
| SORL1 | CNTN5 | 1 | + | + | chr11 | chr11 | 121393698 | 99690275 |
| SORL1 | TBCEL | 1 | + | + | chr11 | chr11 | 121348952 | 120957487 |
| SP3 | PRCP | 1 | − | − | chr2 | chr11 | 174819601 | 82564320 |
| SPAG17 | RABGAP1L | 1 | − | + | chr1 | chr1 | 118693166 | 174926594 |
| SPEN | PLEKHM2 | 1 | + | + | chr1 | chr1 | 16203173 | 16060292 |
| SPRED1 | TMCO5A | 1 | + | + | chr15 | chr15 | 38545418 | 38228515 |
| SPRED2 | G2E3 | 1 | − | + | chr2 | chr14 | 65659096 | 31050282 |
| SPTLC2 | PID1 | 1 | − | − | chr14 | chr2 | 78063529 | 230020680 |
| SREBF1 | LRRC48 | 1 | − | + | chr17 | chr17 | 17740041 | 17877166 |
| SRM | SMEK1 | 1 | − | − | chr1 | chr14 | 11118857 | 91957146 |
| SRP68 | AP1M2 | 1 | − | − | chr17 | chr19 | 74046509 | 10694746 |
| SRP68 | URM1 | 1 | − | + | chr17 | chr9 | 74039910 | 131150095 |
| SRRT | PPP1R17 | 1 | + | + | chr7 | chr7 | 100479862 | 31732020 |
| SSBP2 | SERINC5 | 1 | − | − | chr5 | chr5 | 80762793 | 79407525 |
| SSH2 | ANO1 | 1 | − | + | chr17 | chr11 | 28256956 | 69957813 |
| SSH2 | ANO1 | 1 | − | + | chr17 | chr11 | 28256956 | 69962564 |
| ST3GAL3 | KDM4A | 1 | + | + | chr1 | chr1 | 44202051 | 44118808 |
| ST3GAL4 | FAM118B | 1 | + | + | chr11 | chr11 | 126279306 | 126124200 |
| ST7 | CAV1 | 1 | + | + | chr7 | chr7 | 116593745 | 116199000 |
| STARD7 | HS1BP3 | 1 | − | − | chr2 | chr2 | 96852955 | 20824652 |
| STAU2 | PAWR | 1 | − | − | chr8 | chr12 | 74659018 | 80014987 |
| STAU2 | PAWR | 1 | − | − | chr8 | chr12 | 74659622 | 80014987 |
| STK3 | POLR2K | 1 | − | + | chr8 | chr8 | 99837743 | 101163575 |
| STRBP | SLC35D2 | 1 | − | − | chr9 | chr9 | 126030715 | 99130587 |
| STX8 | RTN1 | 1 | − | − | chr17 | chr14 | 9281869 | 60074210 |
| SUDS3 | CDK4 | 1 | + | − | chr12 | chr12 | 118829087 | 58144548 |
| SULF1 | RPS29 | 1 | + | − | chr8 | chr14 | 70501376 | 50044571 |
| SULF1 | RPS29 | 1 | + | − | chr8 | chr14 | 70501376 | 50052767 |
| SUMF1 | CNTN4 | 1 | − | + | chr3 | chr3 | 4458812 | 3030029 |
| SYMPK | CRYL1 | 1 | − | − | chr19 | chr13 | 46352008 | 20987526 |
| SYNGAP1 | COL11A2 | 1 | + | − | chr6 | chr6 | 33393680 | 33133983 |
| SYNJ2BP | TRPC4AP | 1 | − | − | chr14 | chr20 | 70883617 | 33609159 |
| TAF12 | ATAD3C | 1 | − | + | chr1 | chr1 | 28969504 | 1403764 |
| TARS2 | RPRD2 | 1 | + | + | chr1 | chr1 | 150464965 | 150443037 |
| TAX1BP1 | JAZF1 | 1 | + | − | chr7 | chr7 | 27797752 | 28031600 |
| TBC1D15 | SLC16A7 | 1 | + | + | chr12 | chr12 | 72266783 | 60165000 |
| TBCD | FOXK2 | 1 | + | + | chr17 | chr17 | 80714091 | 80544939 |
| TBK1 | HGSNAT | 1 | + | + | chr12 | chr8 | 64845967 | 43033217 |
| TBL1XR1 | MIPEP | 1 | − | − | chr3 | chr13 | 176914909 | 24304584 |
| TBL1XR1 | MIPEP | 1 | − | − | chr3 | chr13 | 176914909 | 24330757 |
| TBL3 | NDUFB10 | 1 | + | + | chr16 | chr16 | 2025711 | 2011498 |
| TCF25 | C16orf55 | 1 | + | + | chr16 | chr16 | 89940267 | 89735694 |
| TCF25 | C16orf55 | 1 | + | + | chr16 | chr16 | 89940267 | 89735696 |
| TCOF1 | CD74 | 1 | + | − | chr5 | chr5 | 149755117 | 149785884 |
| TCP1 | ENO1 | 1 | − | − | chr6 | chr1 | 160208775 | 8926560 |

TABLE 1-continued

Chimeras Unveiled by sMACHETE

| 5'-Gene (gene1) | 3'-Gene (gene2) | Number of Samples Found to Have Chimera | strand 1 | strand 2 | Junction Locus Data | | | |
|---|---|---|---|---|---|---|---|---|
| | | | | | chr1 | chr2 | pos1 | pos2 |
| TESK2 | GNA12 | 1 | − | − | chr1 | chr7 | 45851584 | 2834777 |
| TFEB | ADK | 1 | − | + | chr6 | chr10 | 41654832 | 76074425 |
| TG | THADA | 1 | + | − | chr8 | chr2 | 133984986 | 43520352 |
| THRAP3 | CAPZB | 1 | + | − | chr1 | chr1 | 36690106 | 19705147 |
| THRAP3 | MAP7D1 | 1 | + | + | chr1 | chr1 | 36690106 | 36641800 |
| THSD4 | LRRC49 | 1 | + | + | chr15 | chr15 | 71507738 | 71256124 |
| TIMM44 | DAND5 | 1 | − | + | chr19 | chr19 | 8008492 | 13084203 |
| TIMM50 | SUPT5H | 1 | + | + | chr19 | chr19 | 39977135 | 39966721 |
| TJP2 | FXN | 1 | + | + | chr9 | chr9 | 71766687 | 71714817 |
| TM6SF2 | NCAN | 1 | − | + | chr19 | chr19 | 19383930 | 19327756 |
| TM9SF3 | RPP30 | 1 | − | + | chr10 | chr10 | 98346491 | 92655637 |
| TM9SF4 | COMMD7 | 1 | + | − | chr20 | chr20 | 30749168 | 31315949 |
| TM9SF4 | HM13 | 1 | + | + | chr20 | chr20 | 30697558 | 30136832 |
| TMEM135 | MIPEP | 1 | + | − | chr11 | chr13 | 86749228 | 24304584 |
| TMEM170B | SMIM13 | 1 | + | + | chr6 | chr6 | 11538607 | 11134636 |
| TMEM179B | SCGB1D1 | 1 | + | + | chr11 | chr11 | 62554999 | 61959528 |
| TMEM19 | TSPAN8 | 1 | + | − | chr12 | chr12 | 72083484 | 71551567 |
| TMEM8B | NPR2 | 1 | + | + | chr9 | chr9 | 35846992 | 35802500 |
| TMEM97 | BLMH | 1 | + | − | chr17 | chr17 | 26646391 | 28593972 |
| TMEM97 | BLMH | 1 | + | + | chr17 | chr17 | 26646391 | 28601215 |
| TNRC6A | PRKCB | 1 | + | + | chr16 | chr16 | 24741621 | 24192111 |
| TP53 | DNAH2 | 1 | − | + | chr17 | chr17 | 7590695 | 7727152 |
| TP53 | DNAH2 | 1 | − | + | chr17 | chr17 | 7590695 | 7727439 |
| TP53 | DNAH2 | 1 | − | + | chr17 | chr17 | 7590695 | 7733618 |
| TPX2 | BCL2L1 | 1 | + | − | chr20 | chr20 | 30330450 | 30253889 |
| TPX2 | COX4I2 | 1 | + | + | chr20 | chr20 | 30327424 | 30232571 |
| TPX2 | COX4I2 | 1 | + | + | chr20 | chr20 | 30330450 | 30227736 |
| TPX2 | COX4I2 | 1 | + | + | chr20 | chr20 | 30347982 | 30227736 |
| TRAPPC10 | GRID1 | 1 | + | − | chr21 | chr10 | 45432441 | 87628937 |
| TRAPPC10 | RRP1 | 1 | + | + | chr21 | chr21 | 45432441 | 45211231 |
| TRMT1 | C19orf53 | 1 | − | + | chr19 | chr19 | 13226093 | 13888866 |
| TRMU | UPK3A | 1 | + | + | chr22 | chr22 | 46733841 | 45689062 |
| TRPM2 | AGPAT3 | 1 | + | + | chr21 | chr21 | 45846619 | 45379515 |
| TRPS1 | TBC1D9B | 1 | − | − | chr8 | chr5 | 116599228 | 179321614 |
| TSFM | GLI1 | 1 | + | + | chr12 | chr12 | 58180945 | 57858456 |
| TSFM | INHBE | 1 | + | + | chr12 | chr12 | 58186856 | 57849877 |
| TSFM | KDM2B | 1 | + | + | chr12 | chr12 | 58186856 | 121987543 |
| TTC39C | CABLES1 | 1 | + | + | chr18 | chr18 | 21595002 | 20837191 |
| TTC7B | PPP1R21 | 1 | − | + | chr14 | chr2 | 91142867 | 48734408 |
| TTLL11 | VWCE | 1 | − | − | chr9 | chr11 | 124801551 | 61050377 |
| TTLL5 | JDP2 | 1 | + | + | chr14 | chr14 | 76135865 | 75935993 |
| TUBD1 | VMP1 | 1 | − | + | chr17 | chr17 | 57941025 | 57814814 |
| TUBD1 | VMP1 | 1 | − | + | chr17 | chr17 | 57941025 | 57816198 |
| TUBD1 | VMP1 | 1 | − | + | chr17 | chr17 | 57941025 | 57842332 |
| TXNDC15 | ARPC2 | 1 | + | + | chr5 | chr2 | 134210220 | 219103387 |
| TXNL1 | GRP | 1 | − | + | chr18 | chr18 | 54278224 | 56892724 |
| UBA2 | PDCD2L | 1 | + | + | chr19 | chr19 | 34929671 | 34916895 |
| UBAP2 | C15orf41 | 1 | − | + | chr15 | chr15 | 33923184 | 37100525 |
| UBAP2 | NCF4 | 1 | − | + | chr9 | chr22 | 33986758 | 37271695 |
| UBE2G2 | ABCG1 | 1 | − | + | chr21 | chr21 | 46207835 | 43704670 |
| UBE2Q1 | MAEL | 1 | − | + | chr1 | chr1 | 154525212 | 166974313 |
| UBE2Q1 | MAEL | 1 | − | + | chr1 | chr1 | 154525508 | 166974313 |
| UBE2V2 | MCM4 | 1 | + | + | chr8 | chr8 | 48921030 | 48879925 |
| UBE2V2 | MCM4 | 1 | + | + | chr8 | chr8 | 48921030 | 48882358 |
| UBE4B | PIK3CD | 1 | + | + | chr1 | chr1 | 10093752 | 9751525 |
| UBE4B | PIK3CD | 1 | + | + | chr1 | chr1 | 10093752 | 9770482 |
| UBL3 | RPN2 | 1 | − | + | chr13 | chr20 | 30423649 | 35852281 |
| UBL7 | MAPK9 | 1 | − | − | chr15 | chr5 | 74751025 | 179707608 |
| UBP1 | RSRC1 | 1 | − | + | chr3 | chr3 | 33458250 | 158254881 |
| UBXN7 | RPL39L | 1 | − | − | chr3 | chr3 | 196159198 | 186845850 |
| UNC5A | TTC38 | 1 | + | + | chr5 | chr22 | 176237821 | 46681138 |
| USP1 | INADL | 1 | + | + | chr1 | chr1 | 62907970 | 62613956 |
| USP18 | BAG6 | 1 | + | − | chr22 | chr6 | 18640587 | 31607003 |
| USP53 | TMEM192 | 1 | + | + | chr4 | chr4 | 120181808 | 166009754 |
| USP6NL | AHCY | 1 | − | − | chr10 | chr20 | 11639630 | 32883391 |
| UTRN | LINC00271 | 1 | + | + | chr6 | chr6 | 144761607 | 135963331 |
| VAV3 | ZHX2 | 1 | − | + | chr1 | chr8 | 108138834 | 123875716 |
| VPS13C | ENKD1 | 1 | − | − | chr15 | chr16 | 62221700 | 67697459 |
| VPS13C | ENKD1 | 1 | − | − | chr15 | chr16 | 62221700 | 67697723 |
| VPS13C | ENKD1 | 1 | − | − | chr15 | chr16 | 62221700 | 67697965 |

TABLE 1-continued

Chimeras Unveiled by sMACHETE

| 5'-Gene (gene1) | 3'-Gene (gene2) | Number of Samples Found to Have Chimera | strand 1 | strand 2 | chr1 | chr2 | pos1 | pos2 |
|---|---|---|---|---|---|---|---|---|
| VSTM4 | SCIMP | 1 | − | − | chr10 | chr17 | 50272748 | 5118293 |
| VTCN1 | DNM2 | 1 | − | + | chr1 | chr19 | 117753446 | 10883155 |
| VWC2 | RAB20 | 1 | + | − | chr7 | chr13 | 49815727 | 111176544 |
| WBP1L | SUFU | 1 | + | + | chr10 | chr10 | 104503900 | 104375025 |
| WBSCR17 | AUTS2 | 1 | + | + | chr7 | chr7 | 70598026 | 70163555 |
| WHSC1L1 | SNX20 | 1 | − | − | chr8 | chr16 | 38239317 | 50711446 |
| WRB | ERG | 1 | + | − | chr21 | chr21 | 40752412 | 39817544 |
| WWOX | C15orf41 | 1 | + | + | chr16 | chr15 | 78198186 | 37100525 |
| WWP2 | SNTB2 | 1 | + | + | chr16 | chr16 | 69833198 | 69317951 |
| XKR9 | LACTB2 | 1 | + | − | chr8 | chr8 | 71619388 | 71574132 |
| YEATS2 | SEC62 | 1 | + | + | chr3 | chr3 | 183442319 | 169710382 |
| YEATS4 | MARS | 1 | + | + | chr12 | chr12 | 69764755 | 57905481 |
| YEATS4 | PTPRR | 1 | + | − | chr12 | chr12 | 69764755 | 71056385 |
| YEATS4 | XRCC6BP1 | 1 | + | + | chr12 | chr12 | 69764755 | 58339411 |
| YEATS4 | XRCC6BP1 | 1 | + | + | chr12 | chr12 | 69764755 | 58340778 |
| YEATS4 | XRCC6BP1 | 1 | + | + | chr12 | chr12 | 69764755 | 58345541 |
| ZBTB20 | CPM | 1 | − | − | chr3 | chr12 | 114219199 | 69260828 |
| ZBTB20 | MTL5 | 1 | − | − | chr3 | chr11 | 114219199 | 68475968 |
| ZBTB20 | RERE | 1 | − | − | chr3 | chr1 | 114619151 | 8674745 |
| ZBTB7A | TNK1 | 1 | − | + | chr19 | chr17 | 4053969 | 7286155 |
| ZBTB7C | RAB12 | 1 | − | + | chr18 | chr18 | 45663378 | 8624936 |
| ZC3H3 | TRAPPC9 | 1 | − | − | chr8 | chr8 | 144618427 | 141461482 |
| ZC3H7B | RBX1 | 1 | + | + | chr22 | chr22 | 41752812 | 41368480 |
| ZDHHC5 | SMTNL1 | 1 | + | + | chr11 | chr11 | 57435659 | 57313354 |
| ZEB2 | CXCR4 | 1 | − | − | chr2 | chr2 | 145274845 | 136873482 |
| ZFC3H1 | MON2 | 1 | − | + | chr12 | chr12 | 72050665 | 62972225 |
| ZFC3H1 | MON2 | 1 | − | + | chr12 | chr12 | 72050665 | 62974077 |
| ZFP36 | PAF1 | 1 | + | − | chr19 | chr19 | 39897568 | 39880801 |
| ZFPM2 | CHMP4C | 1 | + | + | chr8 | chr8 | 106331209 | 82665299 |
| ZHX2 | VAV3 | 1 | + | − | chr8 | chr1 | 123875778 | 108185377 |
| ZMIZ1 | C10orf107 | 1 | + | + | chr10 | chr10 | 80921890 | 63445799 |
| ZMPSTE24 | CAP1 | 1 | + | + | chr1 | chr1 | 40737707 | 40535362 |
| ZMYND8 | ENTHD1 | 1 | − | − | chr20 | chr22 | 45915973 | 40258012 |
| ZNF18 | TASP1 | 1 | − | − | chr17 | chr20 | 11887430 | 13398168 |
| ZNF234 | CEACAM20 | 1 | + | − | chr19 | chr19 | 44654658 | 45029277 |
| ZNF260 | HECW1 | 1 | − | + | chr19 | chr7 | 37016057 | 43436413 |
| ZNF276 | JPH3 | 1 | + | − | chr16 | chr16 | 89790117 | 87730186 |
| ZNF326 | LRRC8D | 1 | + | + | chr1 | chr1 | 90463713 | 90398626 |
| ZNF43 | ZNF514 | 1 | − | − | chr19 | chr2 | 22028194 | 95818514 |
| ZNF518A | CC2D2B | 1 | + | + | chr19 | chr10 | 97889749 | 97769582 |
| ZNF532 | GMPR | 1 | + | + | chr18 | chr6 | 56621031 | 16247073 |
| ZNF532 | MALT1 | 1 | + | + | chr18 | chr18 | 56532811 | 56390280 |
| ZNF544 | AP2A1 | 1 | + | + | chr19 | chr19 | 58758160 | 50285014 |
| ZNF544 | ZNF274 | 1 | + | + | chr19 | chr19 | 58741828 | 58718087 |
| ZNF550 | CXCL17 | 1 | − | − | chr19 | chr19 | 58067599 | 42938008 |
| ZNF567 | GADD45GIP1 | 1 | + | − | chr19 | chr19 | 37180399 | 13065340 |
| ZNF610 | RALA | 1 | + | + | chr19 | chr7 | 52839759 | 39745722 |
| ZNF772 | ERCC2 | 1 | − | − | chr19 | chr19 | 57988002 | 45860801 |
| ZNF783 | ZNF398 | 1 | + | + | chr7 | chr7 | 148964313 | 148873560 |
| ZNF805 | ETFB | 1 | + | − | chr19 | chr19 | 57752289 | 51857562 |

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A method for unveiling chimeric biomolecule sequences using a computing system, comprising:
   obtaining, using a computing system, a plurality of discordant biomolecule sequence read pairs each having a genetic distance between each read greater than a defined threshold, wherein a discordant read pair signifies the possibility of a fusion junction of a chimeric biomolecule;
   obtaining, using the computing sequence, a plurality of unaligned biomolecule reads that did not align to a reference sequence index as determined by an alignment score, each unaligned read having a paired read;
   classifying, using the computing system, each read pair having an unaligned read as 'consistent' if able to align to a fusion junction sequence in a fusion index and 'inconsistent' if only one read is able to align to a fusion junction sequence in the fusion index, wherein the fusion index comprises a plurality of discordant read pairs;
   classifying, using the computing system, each read pair having an unaligned read as 'artifactual' if able to align to an indel sequence in an indel index, wherein the indel index comprises a set of indel sequences for each fusion junction sequence of the fusion index;
   fitting, using the computing system, a generalized linear model (GLM) for each read, including the 'consistent', 'inconsistent' and 'artifactual' read pairs, to estimate each read's probability that its alignment to a fusion junction sequence was due to an artifact, wherein each read's probability is predicted by alignment score, mapping quality, and the amount of junction overlap;
   generating, using the computing system, a cumulative probability score for each fusion junction sequence by aggregating each read's estimated probability;
   assigning, using the computing system, a junction score to each fusion junction by comparing the cumulative probability score for each fusion junction to a null junction score distribution;
   assigning, using the computing system, an empirical p value for each fusion junction by its junction score to an empirical p value null, wherein the empirical p value reflects the likelihood that the fusion junction is an artifact; and
   producing, using the computing system, a report of at least one fusion junction with its assigned empirical p value.

2. The method of claim 1, further comprising
   obtaining, using the computing system, biomolecule sequence data having a plurality of paired sequence reads;
   aligning, using a computing system, each sequence read of the plurality of read pairs to at least one reference sequence index;
   wherein each read is classified as 'aligned' or 'unaligned'; and
   wherein a read pair have two aligned reads having a genetic distance between each read; and
   classifying, using the computing system, the plurality of read pairs as discordant when the genetic distance between each read of a read pair is greater than the defined threshold, wherein a discordant read pair signifies the possibility of a fusion junction of a chimeric biomolecule.

3. The method of claim 2, where in the at least one reference sequence index includes an index comprising genomic DNA sequences.

4. The method of claim 2, wherein the at least one reference sequence index includes an index comprising exon-exon junction sequences.

5. The method of claim 2, wherein the biomolecule data is trimmed and processed.

6. The method of claim 2, wherein the biomolecule sequence data comprises paired-end sequencing data.

7. The method of claim 2, wherein the biomolecule sequence data comprises split-read sequencing data.

8. The method of claim 2, wherein the biomolecule sequence data is derived de novo, derived from a public or private database, or generated in silico.

9. The method of claim 2, wherein the biomolecule sequence data comprises DNA from at least a partial genome.

10. The method of claim 2, wherein the biomolecule sequence data comprises RNA from at least a partial transcriptome.

11. The method of claim 1 further comprising identifying and removing fusion junctions that are homologous to known splicing events.

12. The method of claim 11, wherein the known splicing events are derived from a publically available reference genome having junction indices.

13. The method of claim 1 further comprising identifying and removing, using the computing system, fusion junctions that are homologous to cryptic splicing events.

14. The method of claim 13, wherein the cryptic splicing events are removed when the 5' and 3' ends of each fusion are within a defined genetic distance.

15. The method of claim 14, wherein the defined genetic distance is selected from the group consisting of 10 kilobases (kb), 25 kb, 50 kb, and 100 kb.

16. The method of claim 1, wherein the defined threshold is selected from the group consisting of, 25 kb, 50 kb, 100 kb and 200 kb.

17. The method of claim 1, wherein the alignment score is calculated by Bowtie2.

18. The method of claim 1 further comprising building, using the computing system, the fusion index comprising the plurality of fusion junction sequences derived from the plurality of discordant read pairs;
 wherein each of the plurality of fusion junction sequences are an exon-exon boundary of two discordant exons identified by the discordant read pairs; and
 wherein each of the plurality of fusion junction sequences signifies a candidate chimeric biomolecule.

19. The method of claim 1 further comprising building, using the computing system, the indel index comprising the set of indel sequences for each fusion junction sequence of the fusion index; wherein each set of indel sequences comprises a plurality of 5' junction sequences having at least one insertion at the junction breakpoint, a plurality of 3' junction sequences having at least one insertion at the junction breakpoint, a plurality of 5' junction sequences having at least one deletion at the junction breakpoint, and a plurality 3' junction sequences having at least one insertion at the junction breakpoint.

20. The method of claim 1, wherein the GLM is fitted using the command:
 x=glm(is.pos~overlap+lenAdjScore+qual+lenAdjScoreR2+qualR2,
  data=readPredictions,
  family=binomial(link="logit"),
  weights=readPredictions[,cur_weight])
where is.pos is 1 for "consistent" reads and 0 for "inconsisten" reads, overlap is a minimum number of nucleotides that flank each side of the junction breakpoint, qualR2 are mapping qualities, and lenAdjScoreR2 is an adjusted alignment score.

21. The method of claim 1, wherein the null junction score is constructed for each value of the number of reads aligning to the fusion by randomly sampling from the empirical distribution of probability that a read is an artifact for all reads in the obtained sequencing reads.

22. The method of claim 1, wherein the null junction score is constructed for each value of the number of reads aligning to the fusion junction using the Hoeffding combinatorial central limit theorem.

23. The method of claim 1, wherein the empirical p value for each fusion junction is estimated by referring its junction to an empirical distribution of junction scores of mappable fusion junctions.

24. The method of claim 1, wherein the report includes the junction score of the at least one fusion junction.

25. The method of claim 1 further comprising:
 generating, using the computing system, at least one bloom filter query incorporating at least one fusion junction; and
 applying, using the computing system, the at least one bloom filter query to a hierarchical bloom filter tree data structure.

26. The method of claim 25 further comprising constructing, using the computing system, the hierarchical bloom filter tree data structure.

27. The method of claim 25, wherein the biomolecule sequence data is derived from a large database.

28. The method of claim 27, wherein the large database is The Cancer Genome Atlas (TCGA).

29. The method of claim 1, wherein the report is used to prioritize a candidate chimeric biomolecule for further development of one of research tools, diagnostics, or medicaments.

30. The method of claim 1, wherein the report is used to select a candidate chimeric biomolecule to be used as a template to create a synthetic nucleic acid polymer comprising the sequence of the candidate chimeric biomolecule.

31. The method of claim 1, wherein the report is used to select a candidate chimeric biomolecule to be used as a template to create a synthetic nucleic acid polymer comprising the complementary sequence of the candidate chimeric biomolecule.

32. The method of claim 1, wherein the report is used to select a candidate chimeric biomolecule to be used as a template to create an expression vector to express the candidate chimeric biomolecule in a suitable expression system.

33. The method of claim 1, wherein the report is used to select a candidate chimeric biomolecule to develop a biomarker to detect the candidate chimeric biomolecule.

34. The method of claim 33, wherein the biomarker is used to diagnose a biological sample.

35. The method of claim 1, wherein the report is used to select a candidate chimeric biomolecule to develop a drug screening platform utilizing to genetically modified cells that incorporate the candidate chimeric biomolecule.

36. The method of claim 1, wherein the report is used to select a candidate chimeric biomolecule to develop an antigen-binding molecule with high specificity, preference and affinity for the candidate chimeric biomolecule.

37. The method of claim 36, wherein the antigen-binding molecule is a polyclonal antibody.

38. The method of claim 36, wherein the antigen-binding molecule is a monoclonal antibody.

39. A method to query a hierarchical bloom tree data structure utilizing candidate chimeric biomolecule sequences using a computing system, comprising:
   obtaining, using the computing system, a hierarchical bloom filter tree data structure incorporating a number of compressed bloom filters;
wherein the bloom filters are organized within the bloom tree data structure in a hierarchical manner beginning with a root bloom filter, continuing with a plurality of intermediate bloom filters, and ending with a plurality of leaf bloom filters;
   wherein each leaf includes an experimental set of sequence data;
   wherein each intermediate bloom filter and the root bloom filter is a parent bloom filter associated with a binary node of the hierarchical bloom filter tree data structure such that each parent bloom filter has two downstream child bloom filters; and
   wherein each bloom filter includes a set of k-mers such that each parent bloom filter incorporates the subset of k-mers of each of its children bloom filters and the root bloom filter incorporates the entire collection of k-mers;
   obtaining, using the computing system, at least one biomolecule sequence query that includes at least one candidate chimeric biomolecule sequence;
   breaking, using the computing system, each of the at least one biomolecule sequence queries into a set of k-mers;
   applying, using the computing system, the at least one biomolecule sequence query to the hierarchical bloom filter tree data structure starting with the root bloom filter; and
   wherein the k-mers of the at least one biomolecule sequence query are queried at each parent node by determining whether the k-mers of the at least one biomolecule sequence query are present in the parent node associated bloom filter;
   wherein a positive match between the k-mers of the at least one biomolecule sequence query and the k-mers of the parent node associated bloom filter results in a query of the two downstream child bloom filters; and
   wherein no match between the k-mers of the at least one biomolecule sequence query and the k-mers of the parent node associated bloom filter results in pruning the two downstream children bloom filters and their progeny;
   detecting, using the computing system, the at least one candidate chimeric biomolecule sequence in at least one experimental set of sequence data, wherein a positive match between the k-mers of the at least one biomolecule sequence query and the k-mers of a particular leaf provides that the at least one candidate chimeric biomolecule sequence of the associated with the at least one biomolecule sequence query exists within the experimental set of sequence data associated with the particular leaf; and
   producing, using the computing system, a report indicating the detection of the at least one candidate chimeric biomolecule sequence in the at least one experimental set of sequence data.

40. The method of claim 39, wherein each bloom filter comprises a bit vector having a length and a set of hash functions that map the k-mers to bits in the bit vector.

41. The method of claim 39, wherein the k-mers are a length selected from 17, 18, 19, 20, 21, 22, 23, 24, or 25 nucleotides.

42. The method of claim 39, wherein at least one experimental set of sequence data is derived from a sequencing experiment on a neoplasm.

43. The method of claim 42, wherein the sequencing experiment on the neoplasm is derived from The Cancer Genome Atlas (TCGA).

44. The method of claim 39, wherein the positive match between the k-mers of the at least one biomolecule sequence query and the k-mers of the parent node associated bloom filter is determined by a k-mer threshold.

45. The method of claim 44, wherein the k-mer threshold is uniform for all nodes in the hierarchical bloom filter tree data structure.

46. The method of claim 39, wherein the hierarchical bloom filter tree data structure is obtained by constructing, using the computing system, the hierarchical bloom filter tree data structure.

47. The method of claim 39, wherein at least one candidate chimeric biomolecule sequence is unveiled by:
   obtaining, using the computing system, a plurality of discordant biomolecule sequence read pairs each having a genetic distance between each read greater than a defined threshold, wherein a discordant read pair signifies the possibility of a fusion junction of a chimeric biomolecule;
   obtaining, using the computing system, a plurality of unaligned biomolecule reads that did not align to a reference sequence index as determined by an alignment score, each unaligned read having a paired read;
   classifying, using the computing system, each read pair having an unaligned read as 'consistent' if able to align to a fusion junction sequence in a fusion index and 'inconsistent' if only one read is able to align to a fusion junction sequence in the fusion index, wherein the fusion index comprises a plurality of discordant read pairs;
   classifying, using the computing system, each read pair having an unaligned read as 'artifactual' if able to align to an indel sequence in an indel index, wherein the indel index comprises a set of indel sequences for each fusion junction sequence of the fusion index;
   fitting, using the computing system, a generalized linear model (GLM) for each read, including the 'consistent', 'inconsistent' and 'artifactual' read pairs, to estimate each read's probability that its alignment to a fusion junction sequence was due to an artifact, wherein each read's probability is predicted by alignment score, mapping quality, and the amount of junction overlap;
   generating, using the computing system, a cumulative probability score for each fusion junction sequence by aggregating each read's estimated probability;
   assigning, using the computing system, a junction score to each fusion junction by comparing the cumulative probability score for each fusion junction to a null junction score distribution;
   assigning, using the computing system, an empirical p value for each fusion junction by its junction score to an empirical p value null, wherein the empirical p value reflects the likelihood that the fusion junction is an artifact; and
   producing, using the computing system, a report of at least one fusion junction with its assigned empirical p value.

48. A method for constructing and utilizing a hierarchical bloom tree data structure using a computing system, comprising:

obtaining, using the computing system, a plurality of experimental biomolecule sequence data sets having a plurality of sequence reads;

breaking, using the computing system, each of the plurality of experimental biomolecule sequence data sets into k-mers;

assigning, using the computing system, the k-mers of each of the plurality of experimental biomolecule sequence data sets into leaf bloom filters;

constructing and layering, using the computing system, parental bloom filters to create the hierarchical bloom tree data structure having a root node, a plurality of intermediate nodes, and a plurality of leafs;

wherein the bloom filters are organized within the bloom tree data structure in a hierarchical manner beginning with a root bloom filter, continuing with a plurality of intermediate bloom filters, and ending with a plurality of leaf bloom filters;

wherein each leaf includes an experimental set of sequence data;

wherein each intermediate bloom filter and the root bloom filter is a parent bloom filter associated with a binary node of the hierarchical bloom filter tree data structure such that each parent bloom filter has two downstream child bloom filters; and wherein each bloom filter includes a set of k-mers such that each parent bloom filter incorporates the subset of k-mers of each of its children bloom filters and the root bloom filter incorporates the entire collection of k-mers;

obtaining, using the computing system, at least one biomolecule sequence query that includes at least one candidate chimeric biomolecule sequence;

breaking, using the computing system, each of the at least one biomolecule sequence queries into a set of k-mers; and applying, using the computing system, the at least one biomolecule sequence query to the hierarchical bloom filter tree data structure starting with the root bloom filter; and wherein the k-mers of the at least one biomolecule sequence query are queried at each parent node by determining whether the k-mers of the at least one biomolecule sequence query are present in the parent node associated bloom filter;

wherein a positive match between the k-mers of the at least one biomolecule sequence query and the k-mers of the parent node associated bloom filter results in a query of the two downstream child bloom filters; and wherein no match between the k-mers of the at least one biomolecule sequence query and the k-mers of the parent node associated bloom filter results in pruning the two downstream children bloom filters and their progeny.

49. The method of claim 48, wherein each bloom filter comprises a bit vector having a length and a set of hash functions that map the k-mers to bits in the bit vector.

50. The method of claim 48, wherein the k-mers are a length selected from 17, 18, 19, 20, 21, 22, 23, 24, or 25 nucleotides.

51. The method of claim 48, wherein at least one of the plurality of experimental sets of sequence data is derived from a sequencing experiment on a neoplasm.

52. The method of claim 51, wherein the sequencing experiment on the neoplasm is derived from The Cancer Genome Atlas (TCGA).

53. The method of claim 48, wherein the hierarchical bloom tree data structure is used to detect a candidate chimeric biomolecule sequence the plurality of experimental sets of sequence data.

* * * * *